(12) United States Patent
Burns et al.

(10) Patent No.: US 7,754,188 B2
(45) Date of Patent: Jul. 13, 2010

(54) RADIOLABELED CANNABINOID-1 RECEPTOR MODULATORS

(75) Inventors: H. Donald Burns, Harleysville, PA (US); Alex M. Chen, Cranford, NJ (US); Raymond E. Gibson, Holland, PA (US); Mark T. Goulet, Westfield, NJ (US); William K. Hagmann, Westfield, PA (US); Terence G. Hamill, Lansdale, PA (US); James P. Jewell, Jersey City, NJ (US); Linus S. Lin, Westfield, NJ (US); Ping Liu, Westfield, NJ (US); Andrey V. Peresypkin, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1231 days.

(21) Appl. No.: 10/559,228

(22) PCT Filed: Jun. 25, 2004

(86) PCT No.: PCT/US2004/020233

§ 371 (c)(1),
(2), (4) Date: Dec. 6, 2005

(87) PCT Pub. No.: WO2005/009479

PCT Pub. Date: Feb. 3, 2005

(65) Prior Publication Data

US 2006/0115425 A1 Jun. 1, 2006

Related U.S. Application Data

(60) Provisional application No. 60/483,679, filed on Jun. 30, 2003.

(51) Int. Cl.
*A61K 51/00* (2006.01)
*A61M 36/14* (2006.01)
(52) U.S. Cl. .................... 424/1.65; 424/1.89
(58) Field of Classification Search .............. 424/1.89
See application file for complete search history.

(56) References Cited

U.S. PATENT DOCUMENTS

| 5,698,539 | A | 12/1997 | Ziemer et al. |
| 6,028,084 | A | 2/2000 | Barth et al. |
| 6,555,682 | B1 | 4/2003 | Kannan et al. |
| 6,559,033 | B1 | 5/2003 | Hu et al. |
| 6,972,295 | B2 | 12/2005 | Hagmann et al. |

FOREIGN PATENT DOCUMENTS

| WO | WO 99/31064 | 6/1999 |
| WO | WO 03/031394 | 4/2003 |
| WO | WO 2004/058145 | 7/2004 |

OTHER PUBLICATIONS

Katoch-Rouse et al., J. Med. Chem., vol. 46 (2003), pp. 642-645, "Synthesis, structure-activity relationship, and evaluation of SR141716 analogues: . . . ".
Mathews et al., Nuclear Med. & Biol., vol. 29 (2002), pp. 671-677, "Carbon-11 labeled radioligands for imaging brain cannabinoid receptors".
Mathews et al., Nuclear Med. & Biol., vol. 27 (2000), pp. 757-762, "Biodistribution of [18F] SR144385 and [18F] SR147963: . . . ".
Gifford et al., Chem. and Physics of Lipids, vol. 121 (2002), pp. 65-72, "In vivo imaging of the rain cannabinoid receptor".
Mathews et al., J. of Labelled Compounds and Radiopharm., vol. 42 (1999), pp. 589-596, "Synthesis of [18F] SR144385: . . . ".
Gatley et al., J. of Neurochem., vol. 70 (1998), pp. 417-423, "Imaging the brain marijuana receptor: . . . ".
Goya et al., Exp. Opin. Ther. Patents, vol. 10 (2000), pp. 1529-1538, "Recent advances in cannabinoid receptor agonists and antagonists".
Piomelli et al., TiPS, vol. 21 (2000), pp. 218-224, "The endocannabinoid system as a target for therapeutic drugs".
Barth, Exp. Opin. Ther. Patent, Vo. 8 (1998), pp. 301-313, "Cannabinoid receptor agonists and antagonists".
Kumar et al., Bioorgan. & Med. Chem. Letters, vol. 14 (2004), pp. 2393-2396, "Synthesis of [O-methyl-11C]1-(2-chlorophenyl)-5-(4-methoxyphenyl)-4-methyl-1H-pyrazole-3-carboxylic acid . . . ".
Berding et al., Biol. Psychiatry, vol. 55 (2004), pp. 904-915, "[123]AM281 Single-photon emission computed tomography imaging of cnetral cannabinoid CB1 receptors before and after delta9-tetrahydrocannabinool . . . ".
Lan et al., J. of Labelled Compounds and Radiopharm., vol. 38 (1996), pp. 875-881, "Preparation of iodine-123 labeled AM251: . . . ".
Katoch-Rouse et al., J.of Labelled Compounds and Radiopharm., vol. 46 (2003), pp. 93-98, "Synthesis of N-(piperidin-1-yl)-5-(4-methoxyphenyl)-1-(2-chlorophenyl)-4[18F]fluoro-1H-pyrazole-3-carboxamide . . . ".
Willis et al, J. of Labelled Compounds and Radiopharm., vol. 46 (2003), pp. 799-804, "Regioselective F-18 radiolabeling of AM694, a CB1 cannabinoid receptor ligand".
Li et al., Nuclear Med. & Biol., vol. 32 (2005), pp. 361-366, "Candidate PET radioligands for cannabinoid CB1 receptors: [18F]AM5144 and related pyrazole compounds".

(Continued)

*Primary Examiner*—Michael G Hartley
*Assistant Examiner*—Melissa Perreira
(74) *Attorney, Agent, or Firm*—Baerbel R. Brown; Catherine D. Fitch; John C. Todaro

(57) ABSTRACT

The present invention relates to particular radiolabeled Cannabinoid-1 (CB1) receptor modulators, and methods of using these modulators for labeling and diagnostic imaging of Cannabinoid-1 receptors in mammals, particularly humans. In addition, intermediates useful for the synthesis of the radiolabeled Cannabinoid-1 receptor modulators are also disclosed, as well as the processes for synthesizing the radiolabeled Cannabinoid-1 receptor modulators. Still further, formulations of the radiolabeled Cannabinoid-1 receptor compounds are described.

11 Claims, 2 Drawing Sheets

OTHER PUBLICATIONS

Deng et al., J. Med. Chem., vol. 48 (2005), pp. 6386-6392, "Potent cannabinergic indole analogues as radioiodinatable brain imaging agents for the CB1 cannabinoid receptor".

Xiang et al., Ann. Reports in Med. Chem., vol. 34 (1999), pp. 199-208, "Chapt. 20. Pharmacology of cannabinoid receptor agonists and antagonists".

Mason et al., Ann. Reports in Med. Chem., vol. 40 (2005), pp. 49-61, "Positron emission tomography agents for central nervous system drug development applications".

Lindsey et al., Handbook of Exp. Pharmacol., vol. 168 (2005), pp. 425-443, "Imaging of the Brain Cannabinoid System".

US 7,754,188 B2

RADIOLABELED CANNABINOID-1 RECEPTOR MODULATORS

CROSS-REFERENCE TO RELATED APPLICATIONS

This application is a U.S. National Phase application under 35 U.S.C. §371 of PCT Application No. PCT/US2004/020233, filed Jun. 25, 2004, which claims priority under 35 U.S.C. §119 from U.S. Provisional Application No. 60/483,679, filed Jun. 30, 2003.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lifes of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and in most hospitals worldwide. The most widely used of these are $^{99m}Tc$, $^{201}Tl$ and $^{123}I$.

In the two decades, one of the most active areas of nuclear medicine research has been the development of receptor imaging radiotracers. These tracers bind with high affinity and specificity to selective receptors and neuroreceptors. Successful examples include radiotracers for imaging the following receptor systems: estrogen, muscarinic, dopamine D1 and D2, opiate, neuropeptide-Y, and neurokinin-1.

The natural ligands for the cannabinoid receptors are termed endogenous cannabinoids (endocannabinoids) and include arachidonoyl ethanolamide (anandamide), 2-aminoethyl arachidonate (virodhamine), 2-arachidonoyl glycerol, and 2-arachidonoyl glyceryl ether (noladin ether). Each is an agonist with activities similar to $\Delta^9$-tetrahydrocannabinol, including sedation, hypothermia, intestinal immobility, antinociception, analgesia, catalepsy, anti-emesis, and appetite stimulation. There are two known receptor subtypes for cannabinoids, designated CB1 and CB2. The CB1 receptor subtype is widely distributed throughout the mammalian nervous system (especially brain), and certain peripheral tissues (including the pituitary gland, immune cells, reproductive tissues, gastrointestinal tissues, superior cervical ganglion, heart, lung, urinary bladder, and adrenal gland). The CB2 receptor subtype is present mainly in immune cells (especially B-cells and natural killer cells). A common role for both cannabinoid receptor subtypes is the modulation of the neuronal release of chemical messengers, including acetylcholine, noradrenaline, dopamine, serotonin, γ-aminobutyric acid, glutamate, and aspartate. The receptors for cannabinoids are members of the superfamily of G protein-coupled receptors. This superfamily is an extremely diverse group of receptors in terms of activating ligands and biological functions.

As noted in the review by Gifford A N, et al., (In Vivo Imaging of the Brain Cannabinoid Receptor, Chemistry and Physics of Lipids, 2002, 121 (1-2), 65-72), "Although rodent studies have indicated that in vivo imaging of CB1 receptors is feasible, at the present time this receptor has still to be successfully imaged in a human PET study." (Id., p. 65.). CB1 receptor radioligands for imaging brain CB1 receptors have been made, but in humans have been limited either by poor signal-to noise ratios, low brain uptake and/or rapid clearance. Other attempts are detailed in the following: Lan R, et al., Preparation of Iodine-123 Labeled AM251: A Potential SPECT Radioligand for the Brain Cannabinoid CB1 Receptor, J Labelled Cmpd Radiopharm, 1996, 38(10), 875-881. ([$^{123}I$]-labeling of N-(piperidin-1-yl)-5-(4-iodophenyl)-1-(2,4-dichlorophenyl)-4-methyl-1H-pyrazole-3-carboxamide, an analog of SR131716A (rimomabant)); Gatley S J, et al., Imaging the Brain Marijuana Receptor: Development of a Radioligand that Binds to Cannabinoid CB1 Receptors In Vivo, J Neurochemistry, 1998, 70(1), 417-423. ([$^{123}I$]AM281 studies in mice and baboons); Mathews W B, et al., Synthesis of [$^{18}F$]SR144385: A Selective Radioligand for Positron Emission Tomographic Studies of Brain Cannabinoid Receptors. J Labelled Cmpd Radiopharm, 1999, 42, 589-596; Mathews W B, et al., Biodistribution of [$^{18}F$]SR144385 and [$^{18}F$]SR147963: Selective Radioligands for Positron Emission Tomographic Studies of Brain Cannabinoid Receptors. Nuc Med Biol, 2000, 27, 757-762. (synthesis of two pyrazole PET ligands and the results of PET experiments with these ligands in mice); Mathews W B, et al., Carbon-11 Labelled Radioligands for Imaging Brain Cannabinoid Receptors, Nuc Med Biol, 2002, 29, 671-677 (synthesis of [$^{11}C$] SR149080 and [$^{11}C$]SR149568 two 4-methoxy analogs of rimombabant, and in vivo evaluation in mice); Katoch-Rouse R, Horti A G. Synthesis of N-(piperidin-1-yl)-5-(4-methoxypheny)-1-(2-chlorophenyl)-4-[18F]fluoro-1H-pyrazole-3-carboxamide by nucleophilic [18F] fluorination: a PET Radiotracer for Studying CB1 Cannabinoid Receptors, J Labelled Cmpd Radiopharm, 2003, 46, 93-98 (synthesis); Katoch-Rouse, R, et al., Synthesis, Structure-Activity Relationship and Evaluation of SR141716 Analogues: Development of Central Cannabinoid Receptor Ligands with Lower Lipophilicity, J. Med. Chem., 2003, 46, 642-645; Willis P G, et al., Regioselective F-18 Radiolabeling of AM694, A CB1 Cannabinoid Receptor Ligand, J Labelled Cmpd Radiopharm, 2003, 46, 799-804. (synthesis of [1-(5-[18F]fluoropentyl)-1H-indol-3-yl]-(2-iodophenyl)methanone); Kumar et al., Synthesis of [O-methyl-$^{11}C$]1-2-chlorophenyl)-5-(4-methoxyphenyl)-4-methyl-1H-pyrazole-3-carboxylic acid piperidin-1-ylamide: a potential PET ligand for CB1 receptors, Bioorganic & Medicinal Chemistry Letters, 2004, 14, 2393-2396; and Berding et al., [$^{123}I$]AM281 Single-Photon Emission Computed Tomography Imagining of Central Cannabinoid $CB_1$ Receptors Before and After delta$^9$-Tetrahydrocannabinal Therapy and Whole-Body Scanning for assessment of Radiation Dose in Tourette Patients, Biol Psychiatry, 2004, 55, 904-915.

Excessive exposure to Δ⁹-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem, A. Doherty, Ed.; Academic Press, NY 1999, Vol. 34, 199-208; Exp. Opin. Ther. Patents 2000, 10, 1529-1538; Trends in Pharma. Sci. 2000, 21, 218-224).

Cannabinoid receptor modulating compounds are disclosed in U.S. Pat. Nos. 4,973,587, 5,013,837, 5,081,122, and 5,112,820, 5,292,736 5,532,237, 5,624,941, 6,028,084, and 6,509,367, 6,355,631, 6,479,479 and in PCT Publications WO96/33159, WO97/29079, WO98/31227, WO 98/33765, WO98/37061, WO98/41519, WO98/43635 and WO98/43636, WO99/02499, WO00/10967, and WO00/10968, WO 01/09120, WO 01/70700, WO 01/96330, WO 01/58869, WO 01/64632, WO 01/64633, WO 01/64634, WO 02/076949, WO 03/066007, WO 03/007887, WO 03/02017, WO 03/026647, WO 03/026648, WO 03/027069, WO 03/027076, WO 03/027114, WO 03/037332 and WO 03/040107, and EP-658546.

Schultz, E. M, et al. *J. Med Chem.* 1967, 10, 717 and Pines, S. H. et al. *J. Med. Chem.* 1967, 10, 725 disclose maleamic acids affecting plasma cholesterol and penicillin excretion.

PET (Positron Emission Tomography) radiotracers and imaging technology may provide a powerful method for clinical evaluation and dose selection of cannabinoid-1 receptor agonists, inverse agonists, and antagonists. Using a fluorine-18 or carbon-11 labeled radiotracer that provides a cannabinoid-1 receptor-specific image in the brain and other tissues, the dose required to saturate cannabinoid-1 receptors can be determined by the blockade of the PET radiotracer image in humans. The rationale for this approach is as follows: efficacy of a cannabinoid-1 receptor modulator is a consequence of the extent of receptor inhibition, which in turn is a function of the degree of drug-receptor occupancy.

It is, therefore, an object of this invention to develop radiolabeled cannabinoid-1 receptor modulator that would be useful not only in traditional exploratory and diagnostic imaging applications, but would also be useful in assays, both in vitro and in vivo, for labeling the cannabinoid-1 receptor and for competing with unlabeled cannabinoid-1 receptor antagonists, inverse agonists, and agonists. It is a further object of this invention to develop novel assays which comprise such radiolabeled compounds. It is yet a further object of the present invention to develop intermediates for the synthesis of radiolabled cannabinoid-1 modulators.

SUMMARY OF THE INVENTION

Figure 1:
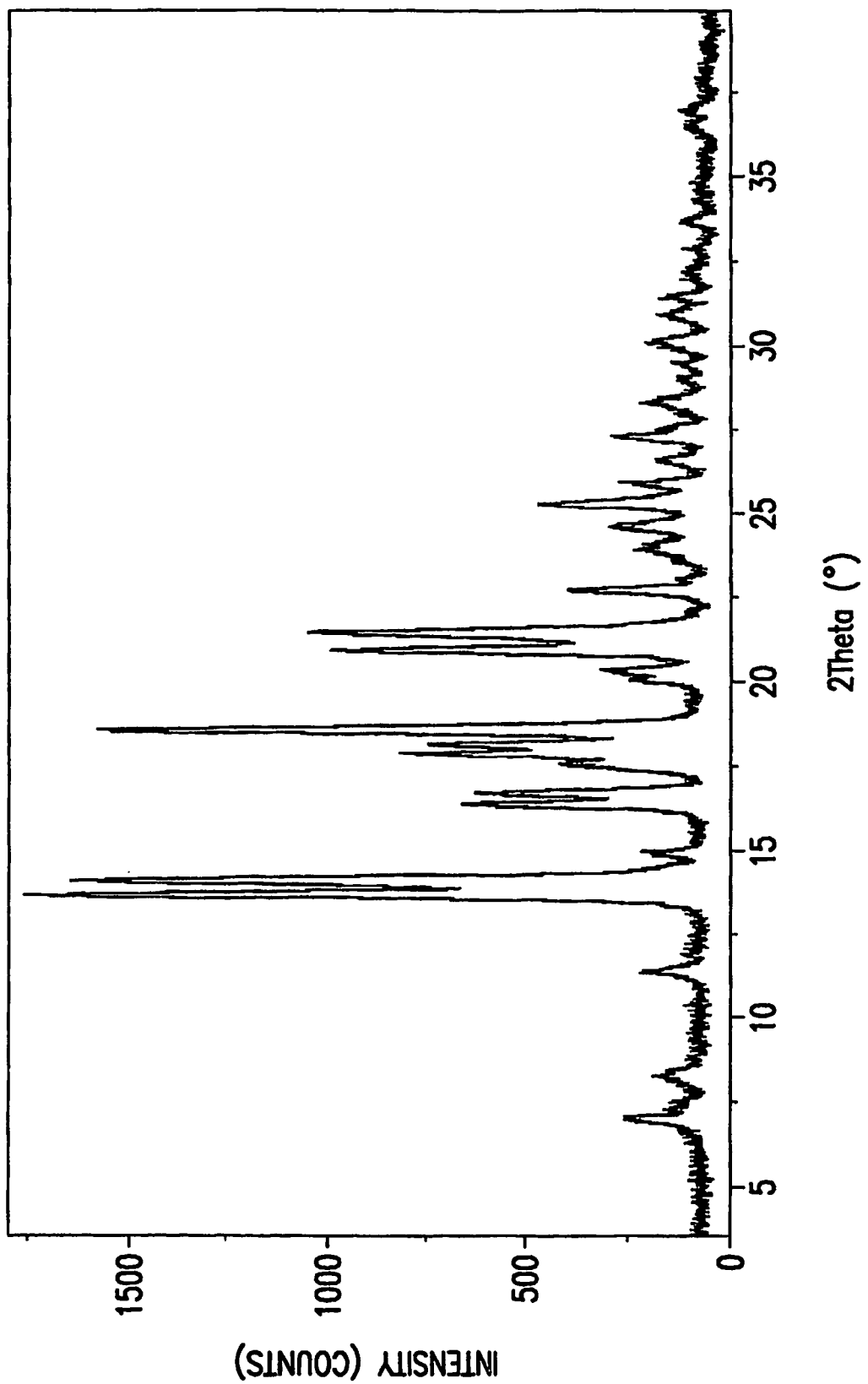
FIG. 1 represents the X-ray powder diffraction pattern (XRPD) of (N-[2-(3-Cyanophenyl)-3-(4-hydroxyphenyl)-1-methylpropyl]-2-(5-methyl-2-pyridyloxy)-2-methylpropanamide). The X axis represents 2-theta in degrees the Y axis represents Intensity in counts.

The present invention is directed to certain radiolabeled cannabinoid-1 receptor modulators. The present invention is further concerned with methods for the use of such radiolabeled cannabinoid-1 receptor modulators for the labeling and diagnostic imaging of cannabinoid-1 receptors in mammals. Still further, the present invention is directed to intermediates useful for the synthesis of radiolabeled cannabinoid 1 modulators. The invention is also concerned with pharmaceutical formulations comprising one of the compounds as an active ingredient. The invention is further concerned with processes for preparing the compounds of this invention.

DETAILED DESCRIPTION OF THE INVENTION

The present invention is directed to certain radiolabeled cannabinoid-1 receptor modulators. In particular, the present invention is directed to compounds of the formula I:

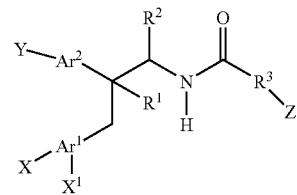

wherein:
$Ar^1$ and $Ar^2$ are phenyl or pyridyl,
wherein phenyl and pyridyl are optionally substituted with one to three substituents independently selected from $R^b$;
$R^1$ is selected from:
   (1) hydrogen,
   (2) hydroxyl,
   (3) fluoro,
   (4) cyano, and
   (5) $C_{1-4}$alkyl;
$R^2$ is selected from
   (1) hydrogen, and
   (2) $C_{1-4}$alkyl,
$R^3$ is selected from
   (1) $C_{1-10}$alkyl,
   (2) $C_{2-10}$alkenyl,
   (3) $C_{3-10}$cycloalkyl,
   (4) $C_{3-10}$cycloalkyl-$C_{1-4}$alkyl,
   (5) cycloheteroalkyl,
   (6) cycloheteroalkyl-$C_{1-4}$alkyl,
   (7) aryl,
   (8) aryl-$C_{1-4}$alkyl,
   (9) diaryl-$C_{1-4}$alkyl,
   (10) aryl-$C_{1-4}$alkenyl,
   (11) heteroaryl,
   (12) heteroaryl-$C_{1-4}$alkyl,
   (13) —$OR^d$, and
   (14) —$NR^cR^d$;

wherein alkyl, and alkenyl are optionally substituted with one to three substituents independently selected from $R^a$, and cycloalkyl, cycloheteroalkyl, aryl and heteroaryl are optionally substituted with one to three substituents independently selected from $R^b$;
each $R_a$ is independently selected from:
(1) —$OR^d$,
(2) —$NR^cS(O)_mR^d$,
(3) halogen,
(4) —$SR^d$,
(5) —$S(O)_mNR^cR^d$,
(6) —$NR^cR^d$,
(7) —$C(O)R^d$,
(8) —$CO_2R^d$,
(9) —CN,
(10) —$C(O)NR^cR^d$,
(11) —$NR^cC(O)R^d$,
(12) —$NR^cC(O)OR^d$,
(13) —$NR^cC(O)NR^cR^d$,
(14) —$CF_3$,
(15) —$OCF_3$, and
(16) cycloheteroalkyl;
each $R^b$ is independently selected from:
(1) $R^a$,
(2) $C_{1-10}$alkyl,
(3) aryl,
(4) aryl$C_{1-4}$alkyl,
(5) heteroaryl, and
(6) heteroaryl$C_{1-4}$alkyl,
$R^c$ and $R^d$ are independently selected from:
(1) hydrogen,
(2) $C_{1-10}$alkyl,
(3) $C_{2-10}$alkenyl,
(4) cycloalkyl,
(5) cycloalkyl-$C_{1-10}$alkyl;
(6) cycloheteroalkyl,
(7) cycloheteroalkyl-$C_{1-10}$alkyl;
(8) aryl,
(9) heteroaryl,
(10) aryl-$C_{1-10}$alkyl, and
(11) heteroaryl-$C_{1-10}$alkyl, or
$R^c$ and $R^d$ together with the atom(s) to which they are attached form a heterocyclic ring of 4 to 7 members containing 0-2 additional heteroatoms independently selected from oxygen, sulfur and N—Re, each $R^c$ and $R^d$ may be unsubstituted or substituted with one to three substituents selected from $R^f$;
each $R^e$ is independently selected from
(1) hydrogen,
(2) $C_{1-10}$alkyl, and
(3) —$C(O)R^g$;
each $R^f$ is independently selected from:
(1) halogen,
(2) $C_{1-10}$alkyl,
(3) —O—$C_{1-4}$alkyl,
(4) —S—$C_{1-4}$Alkyl,
(5) —$S(O)_mC_{1-4}$alkyl,
(6) —CN,
(7) —$CF_3$, and
(8) —$OCF_3$; and
m is selected from 1 and 2;
$R^g$ is selected from:
(1) hydrogen,
(2) $C_{1-10}$alkyl,
(3) $C_{2-10}$alkenyl,
(4) cycloalkyl,
(5) cycloalkyl-$C_{1-10}$alkyl;
(6) cycloheteroalkyl,
(7) cycloheteroalkyl-$C_{1-10}$alkyl;
(8) aryl,
(9) heteroaryl,
(10) aryl-$C_{1-10}$alkyl, and
(11) heteroaryl-$C_{1-10}$alkyl, or
$X^1$ is hydrogen or the radionuclide $^3H$;
one of X, Y, and Z is selected from:
(1) a radionuclide selected from the group consisting of: $^3H$, 11C, $^{18}F$, $^{125}I$, $^{82}Br$, $^{123}I$, $^{131}I$, $^{75}Br$, $^{15}O$, $^{13}N$, $^{211}At$ and $^{77}Br$,
(2) —CN,
(3) —$C_{1-4}$alkyl
(4) —O—$C_{1-4}$alkyl,
wherein alkyl and cyano contain one $^{11}C$ radionuclide or allyl is substituted with one to three $^{18}F$ atoms, and alkyl is unsubstituted or substituted with one or two fluoro substituents, and the other two of X, Y, and Z are each hydrogen;

and pharmaceutically acceptable salts thereof.

In one embodiment of the present invention, $Ar^1$ is selected from phenyl unsubstiuted or subsituted with one or two substituents selected from $R^b$. In one class of this embodiment, $Ar^1$ is phenyl, unsubstituted or substituted with halogen, ethoxy, methoxy, and hydroxy. In one subclass of this class, $Ar^1$ is selected from phenyl, 4-chlorophenyl, 4-fluorophenyl, 4-ethyoxyphenyl, 4-methoxyphenyl, 4-hydroxyphenyl.

In one embodiment of the present invention, $Ar^2$ is phenyl, unsubstituted or substituted with one or two substituents selected from $R^b$. In one class of this embodiment, $Ar^2$ is phenyl, unsubstituted or substituted with one or two substituents selected from halogen and cyano. In one class of this embodiment, $Ar^2$ is phenyl, substituted with one or two substituents selected from cyano, fluoro and bromo. In one subclass, $Ar^2$ is selected from 3-cyanophenyl, 3-fluoro-5-bromophenyl, 3-cyano-5-fluorophenyl, and 3-cyano-5-bromophenyl.

In one embodiment of the present invention, $R^1$ is selected from hydrogen, hydroxy, fluoro, cyano and methyl. In a class of this embodiment, $R^1$ is selected from hydrogen, hydroxyl, fluoro, and methyl. In a subclass of this class, $R^1$ is selected from hydrogen, fluoro, and hydroxyl. In another subclass of this class, $R^1$ is selected from hydrogen and fluoro. In yet another subclass, $R^1$ is hydrogen.

In one embodiment of the present invention, $R^2$ is selected from: hydrogen, methyl, ethyl, and isopropyl.

In one class of this embodiment, $R^2$ is selected from hydrogen, methyl and ethyl.

In one subclass of this class, $R^2$ is methyl.

In another embodiment of the present invention, $R^3$ is selected from:
(1) $C_{1-10}$alkyl,
(2) $C_{2-10}$alkenyl,
(3) $C_{3-10}$cycloalkyl-$C_{1-4}$alkyl,
(4) cycloheteroalkyl-$C_{1-4}$alkyl,
(5) aryl-$C_{1-4}$alkyl,
(6) diaryl-$C_{1-4}$alkyl,
(7) aryl-$C_{1-4}$alkenyl,
(8) heteroaryl-$C_{1-4}$alkyl,
(9) —$OR^d$, and
(10) —$NR^cR^d$, wherein each alkyl or alkenyl is optionally substituted with one or two substituents independently selected from $R^a$, and each cycloalkyl, cycloheteroalkyl, aryl and heteroaryl is each optionally substituted with on to three substituents independently selected from $R^b$.

In one class of this embodiment of the present invention, $R^3$ is selected from:
(1) $C_{1-8}$alkyl,
(2) $C_{2-8}$alkenyl,
(3) $C_{3-10}$cycloalkyl,
(4) cycloheteroalkyl-$C_{1-4}$alkyl,
(5) aryl-$C_{1-4}$alkyl,
(6) diaryl-$C_{1-4}$alkyl,
(7) aryl-$C_{1-4}$alkenyl,
(8) heteroaryl-$C_{1-4}$alkyl,
(9) —$OR^d$, and
(10) —$NR^cR^d$, wherein each alkyl or alkenyl is optionally substituted with one or two substituents independently selected from $R^a$, and each cycloalkyl, cycloheteroalkyl, aryl and heteroaryl is each optionally substituted with on to three substituents independently selected from $R^b$.

In a subclass of this embodiment of the present invention, $R^3$ is selected from:
(1) $C_{1-8}$alkyl,
(2) $C_{2-8}$alkenyl,
(3) cycloheteroalkyl-$C_{1-4}$alkyl,
(4) aryl-$C_{1-4}$alkyl,
(5) diaryl-$C_{1-4}$alkyl,
(6) aryl-$C_{1-4}$alkenyl,
(7) heteroaryl-$C_{1-4}$alkyl,
(8) —$OR^d$, and
(9) —$NR^cR^d$, wherein each alkyl or alkenyl is optionally substituted with one or two substituents independently selected from $R^a$, and each cycloalkyl, cycloheteroalkyl, aryl and heteroaryl is each optionally substituted with on to three substituents independently selected from $R^b$.

In another subclass of this embodiment of the present invention, $R^3$ is selected from:
(1) $C_{1-8}$alkyl,
(2) $C_{2-8}$alkenyl,
(3) $C_{3-10}$cycloalkyl,
(4) cycloheteroalkyl-$C_{1-4}$alkyl,
(5) aryl-$C_{1-4}$alkyl,
(6) diaryl-$C_{1-4}$alkyl,
(7) aryl-$C_{1-4}$alkenyl,
(8) heteroaryl-$C_{1-4}$alkyl,
(9) —$OR^d$, and
(10) —$NR^cR^d$, wherein each alkyl or alkenyl is optionally substituted with one or two substituents independently selected from $R^a$, and each cycloalkyl, cycloheteroalkyl, aryl and heteroaryl is each optionally substituted with one to three substituents independently selected from $R^b$ and wherein cycloheteroalkyl is selected from pyrrolidinyl, morpholinyl, piperazinyl, and piperidinyl; aryl is selected from phenyl and naphthyl; and heteroaryl is selected from pyridyl, pyrazolyl, triazolyl, pyrimidyl, isoxazolyl, indolyl and thiazolyl.

In an additional subclass of this embodiment of the present invention, $R^3$ is selected from:
(1) $C_{1-8}$alkyl,
(2) $C_{2-8}$alkenyl,
(3) cycloheteroalkyl-$C_{1-4}$alkyl,
(4) aryl-$C_{1-4}$alkyl,
(5) diaryl-$C_{1-4}$alkyl,
(6) aryl-$C_{1-4}$alkenyl,
(7) heteroaryl-$C_{1-4}$alkyl,
(8) —$OR^d$, and
(9) —$NR^cR^d$, wherein each alkyl or alkenyl is optionally substituted with one or two substituents independently selected from $R^a$, and each cycloalkyl, cycloheteroalkyl, aryl and heteroaryl is each optionally substituted with one to three substituents independently selected from $R^b$ and wherein cycloheteroalkyl is selected from pyrrolidinyl, morpholinyl, piperazinyl, and piperidinyl; aryl is selected from phenyl and naphthyl; and heteroaryl is selected from pyridyl, pyrazolyl, triazolyl, pyrimidyl, isoxazolyl, indolyl and thiazolyl.

In still another subclass, $R^3$ is selected from: isopropyl, isobutyl, t-butyl, pentyl, benzyl, α-hydroxy-benzyl, α-methoxy-benzyl, α-ethyl-benzyl, α-ethyl-cyclobutyl, α-propyl-cyclobutyl, α-butyl-cyclobutyl, α-ethyl-cyclopentyl, α-propyl-cyclopentyl, α-butyl-cyclopentyl, α-hydroxy-diphenyl-methyl, 3-(aminosulfonyl)-propyl, 5-(t-butyloxycarbonylamino)-pentyl, anilino, anilino-methyl, t-butoxy, phenoxy, benzyloxy, 1-naphthyl-methyl, phenyl-ethyl, 3-phenyl-propyl, 3,3-diphenyl-propyl, 2-phenyl-ethylene, 1-phenyl-propyl, methoxymethyl, 3-benzoyl-propyl, 7-benzoyl-heptyl, 2-t-butoxy-ethyl, phenoxy-methyl, 1-(phenoxy)-ethyl, 2-(phenoxy)-isopropyl, 2-(pyridyloxy)-isopropyl, 2-(pyrimidinyloxy)-isopropyl, 2-(pyridaziny-loxy)-isopropyl, cyclopropyl-methyl, cyclopentyl-methyl, 2-(cyclohexyloxy)-isopropyl, (1-indanone)-3-methyl, (2-thiazolyl)-S-methyl, (2-benzothiazolyl)-S-methyl, (2-benzoxazolyl)-S-methyl, benztriazolyl-methyl, 2benzothiazolyl)-ethyl, isoxazolyl-methyl, thiazolyl-methyl, triazolyl-methyl, 2-(triazolyl)-ethyl, pyrazolyl-methyl, 2-(pyrazolyl)-ethyl, and (3-(1-oxo-isoindolyl))-methyl; wherein each alkyl or alkenyl is optionally substituted with one or two substituents independently selected from $R^a$, and each cycloalkyl, cycloheteroalkyl, aryl and heteroaryl is each optionally substituted with on to three substituents independently selected from $R^b$.

In yet another subclass of this class of the invention, $R^3$ is $C_{1-8}$alkyl substituted with —$OR^d$.

In still another subclass, $R^3$ is:

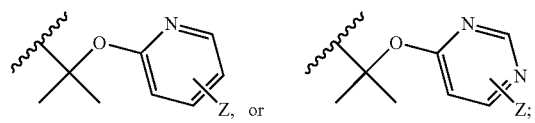

unsubstituted or substituted on the heteroaryl ring with an $R^b$ substituent.

In one embodiment of the present invention, each $R_a$ is independently selected from: —$OR^d$, —$NHS(O)_mR^d$, halogen, —$SR^d$, —$S(O)_mNHR^d$, —$NR^cR^d$, —$C(O)R^d$, —$CO_2R^d$, —$CN$, —$C(O)NHR^d$, —$NHC(O)R^d$, -$NHC(O)OR^d$, —$NHC(O)NHR^d$, —$CF_3$, —$OCF_3$, and cycloheteroalkyl.

In one class of this embodiment of the present invention, each $R_a$ is independently selected from: —$OR^d$, —$NHS(O)_2R^d$, halogen, —$SR^d$, —$S(O)_2NH_2$, —$NHR^d$, —$N(CH_2CH_3)R^d$, —$C(O)R^d$, —$CO_2H$, —$CN$, —$C(O)NHR^d$, —$NHC(O)R^d$, —$NHC(O)OR^d$, —$NHC(O)NHR^d$, —$CF_3$, —$OCF_3$, and cycloheteroalkyl.

In another embodiment of the present invention, each $R_a$ is independently selected from: —$OR^d$, —$NR^cS(O)_mR^d$, halogen, $S(O)_mR^d$, —$S(O)_mNR^cR^d$, —$NR^cR^d$, —$C(O)R^d$, —$CO_2R^d$, —$CN$, —$C(O)NR^cR^d$, —$NR^cC(O)R^d$, —$NR^cC(O)OR^d$, —$NR^cC(O)NR^cR^d$, —$CF_3$, —$OCF_3$, and cycloheteroalkyl.

In one embodiment of the present invention, each $R^b$ is independently selected from: —$OR^d$, —$NHS(O)_m R^d$, halogen, —$SR^d$, —$S(O)_m NHR^d$, —$NHR^d$, —$C(O)R^d$, —$CO_2R^d$, —CN, —$C(O)NR^cR^d$, —$NHC(O)R^d$, —$NHC(O)OR^d$, —$NHC(O)NR^cR^d$, —$CF_3$, —$OCF_3$, cycloheteroalkyl, $C_{1-10}$alkyl, aryl, aryl$C_{1-4}$alkyl, heteroaryl, and heteroaryl $C_{1-4}$alkyl.

In one class of this embodiment, each $R^b$ is independently selected from: —$OR^d$, halogen, —CN, —$CF_3$, —$OCF_3$, cycloheteroalkyl, $C_{1-4}$alkyl, phenyl, benzyl, and heteroaryl.

In one class of this embodiment, each $R^b$ is independently selected from: —$OR^d$, halogen, —CN, —$CF_3$, and methyl.

In one embodiment of the present invention, each $R^c$ is independently selected from: hydrogen, and $C_{1-4}$alkyl, and each $R^d$ is independently selected from: hydrogen, $C_{1-4}$alkyl, $C_{2-6}$ alkenyl, cycloalkyl, cycloalkyl-$C_{1-4}$alkyl, cycloheteroalkyl, cycloheteroalkyl-$C_{1-4}$ alkyl, phenyl, heteroaryl, phenyl-$C_{1-4}$alkyl, and heteroaryl-$C_{1-4}$alkyl, or $R^c$ and $R^d$ together with the atom(s) to which they are attached form a heterocyclic ring of 4 to 7 members containing 0-2 additional heteroatoms independently selected from oxygen, sulfur and N—Re, each $R^c$ and $R^d$ may be unsubstituted or substituted with one to three substituents selected from $R^f$.

In one class of this embodiment of the present invention, each $R^c$ is independently selected from: hydrogen, and $C_{1-4}$alkyl, and each $R^d$ is independently selected from: hydrogen, $C_{1-5}$alkyl, —$CH_2CH=CH_2$, cyclohexyl, cyclopentyl, cyclopropyl, cyclobutylmethyl, cyclopentylmethyl, cyclohexylmethyl, pyrrolidinyl, phenyl, thiazolyl, pyridyl, benzothiazolyl, benzoxazolyl, triazolyl, benzyl, and pyridyl-methyl-, or $R^c$ and $R^d$ together with the atom(s) to which they are attached form a piperidinyl ring, each $R^c$ and $R^d$ may be unsubstituted or substituted with one to three substituents selected from $R^f$.

In one embodiment of the present invention, each $R^e$ is independently selected from: hydrogen, $C_{1-6}$alkyl, and —$C(O)R^g$.

In one class of this embodiment, each $R^e$ is independently selected from: hydrogen, $C_{1-4}$alkyl, and —$C(O)C_{1-4}$allyl.

In one subclass of this class, each $R^e$ is hydrogen, methyl or methylcarbonyl.

In another subclass of this class, each $R^e$ is methyl.

In one embodiment of the present invention, each $R^f$ is independently selected from: halogen, $C_{1-10}$alkyl, —O—$C_{1-4}$alkyl, —S—$C_{1-4}$alkyl, —CN, —$CF_3$, and —$OCF_3$.

In one class of this embodiment, each $R^f$ is independently selected from: halogen, $C_{1-4}$alkyl, —O—$C_{1-4}$alkyl, —S—$C_{1-4}$alkyl, —$S(O)_2C_{1-4}$alkyl, —CN, —$CF_3$, and —$OCF_3$.

In one subclass of this class, each $R^f$ is independently selected from: halogen, methyl, methoxy, methylthio-, —$SO_2CH_3$, —CN, —$CF_3$, and —$OCF_3$.

In another subclass, each $R^f$ is independently selected from: halogen, $C_{1-3}$alkyl, —$SO_2CH_3$, —CN, and —$CF3$.

In one embodiment of the present invention, m is selected from 1 and 2. In one class of this embodiment, m is 2.

In one embodiment of the present invention, $R^g$ is selected from: hydrogen, $C_{1-10}$alkyl, $C_{2-10}$ alkenyl, cycloalkyl, cycloalkyl-$C_{1-10}$alkyl, cycloheteroalkyl, cycloheteroalkyl-$C_{1-10}$alkyl, aryl, heteroaryl, aryl-$C_{1-10}$alkyl, and heteroaryl-$C_{1-10}$alkyl.

In one class of this embodiment, $R^g$ is selected from: hydrogen, $C_{1-4}$alkyl, $C_{2-6}$ alkenyl, cycloalkyl, cycloalkyl-$C_{1-4}$alkyl, cycloheteroalkyl, cycloheteroalkyl-$C_{1-4}$ alkyl, phenyl, heteroaryl, phenyl-$C_{1-4}$alkyl, and heteroaryl-$C_{1-4}$alkyl.

In one subclass of this class, $R^g$ is selected from: hydrogen, $C_{1-5}$alkyl, $CH_2CH=CH_2$, cyclohexyl, cyclopentyl, cyclopropyl, cyclobutylmethyl, cyclopentylmethyl, cyclohexylmethyl, pyrrolidinyl, phenyl, thiazolyl, pyridyl, benzothiazolyl, benzoxazolyl, triazolyl, benzyl, and pyridyl-methyl-.

In another subclass, $R^g$ is selected from:
(1) hydrogen,
(2) $C_{1-4}$alkyl, and
(3) —$C(O)C_{1-4}$alkyl.

In one embodiment of the present invention, $X^1$ is hydrogen; X and Y are hydrogen and Z is selected from:
(1) a radionuclide selected from the group consisting of $^3H$, $^{11}C$, $^{18}F$, $^{125}I$, $^{82}Br$, $^{123}I$, $^{131}I$, $^{75}Br$, $^{15}O$, $^{13}N$, $^{211}At$ and $^{77}Br$,
(2) —CN,
(3) —$C_{1-4}$alkyl,
(4) —O—$C_{1-4}$alkyl, wherein alkyl and cyano contain one $^{11}C$ radionuclide or alkyl is substituted with one to three $^{18}F$ atoms, and alkyl is unsubstituted or substituted with one or two fluoro substituents.

In one class of this embodiment, $X^1$ is hydrogen, X and Y are hydrogen, and Z is selected from:
(1) a radionuclide selected from the group consisting of: $^3H$, $^{18}F$, $^{125}I$, $^{82}Br$, $^{123}I$, $^{131}I$, $^{75}Br$, and $^{77}Br$,
(2) —CN,
(3) —$C_{1-4}$alkyl,
(4) —O—$C_{1-4}$alkyl, wherein alkyl and cyano contain one $^{11}C$ radionuclide or alkyl is substituted with one to three $^{18}F$ atoms, and alkyl is unsubstituted or substituted with one or two fluoro substituents.

In one subclass of this class, $X^1$ is hydrogen, X and Y are hydrogen, and Z is selected from:
(1) $^3H$,
(2) $^{18}F$,
(3) cyano, wherein the carbon is $^{11}C$,
(4) $CH_3$, wherein the carbon is $^{11}C$, and
(5) —$CF_2$—$^{18}F$.

In another subclass of this class, $X^1$ is hydrogen, X and Y are hydrogen, and Z is $CF_2$—$^{18}F$.

In another embodiment of the present invention, $X^1$ is hydrogen;

X and Z are hydrogen and Y is selected from:
(1) a radionuclide selected from the group consisting of: $^3H$, $^{11}C$, $^{18}F$, $^{125}I$, $^{82}Br$, $^{123}I$, $^{131}I$, $^{75}Br$, $^{15}O$, $^{13}N$, $^{211}At$ and $^{77}Br$,
(2) —CN,
(3) —$C_{1-4}$alkyl,
(4) —O—$C_{1-4}$alkyl, wherein alkyl and cyano contain one $^{11}C$ radionuclide or alkyl is substituted with one to three $^{18}F$ atoms, and alkyl is unsubstituted or substituted with one or two fluoro substituents.

In class of this embodiment, $X^1$ is hydrogen, X and Z are hydrogen and Y is selected from:
(1) a radionuclide selected from the group consisting of: $^3H$, $^{18}F$, $^{125}I$, $^{82}Br$, $^{123}I$, $^{131}I$, $^{75}Br$, and $^{77}Br$,
(2) —CN,
(3) —$C_{1-4}$alkyl,
(4) —O—$C_{1-4}$alkyl, wherein alkyl and cyano contain one $^{11}$C radionuclide or alkyl is substituted with one to three $^{18}$F atoms, and alkyl is unsubstituted or substituted with one or two fluoro substituents.

In one subclass of this class, $X^1$ is hydrogen, X and Z are hydrogen and Y is selected from:
(1) $^{18}$F,
(2) $CH_3$, wherein the carbon is $^{11}$C,
(3) —O—$^{11}CH_3$,
(4) —$OCH_2$—$^{18}$F,
(5) —OC—$(^2H)_2$—$^{18}$F,
(6) —$OCH_2CH_2$—$^{18}$F; and
(7) cyano wherein the carbon is $^{11}$C.

In another subclass of this class, $X^1$ is hydrogen, X and Z are hydrogen, and Y is selected from:
(1) the radionuclide $^{18}$F, and
(2) cyano wherein the carbon is $^{11}$C.

In yet another embodiment of the present invention, $X^1$ is hydrogen and Y and Z are hydrogen, and X is selected from:
(1) a radionuclide selected from the group consisting of: $^3$H, $^{11}$C, $^{18}$F, $^{125}$I, $^{82}$Br, $^{123}$I, $^{131}$I, $^{75}$Br, $^{15}$O, $^{13}$N, $^{211}$At and $^{77}$Br,
(2) —CN,
(3) —$C_{1-4}$alkyl
(4) —O—$C_{1-4}$alkyl, wherein alkyl and cyano contain one $^{11}$C radionuclide or alkyl is substituted with one to three $^{18}$F atoms, and alkyl is unsubstituted or substituted with one or two fluoro substituents.

In a class of this embodiment, $X^1$ is hydrogen and Y and Z are hydrogen, and X is selected from:
(1) a radionuclide selected from the group consisting of: $^3$H, $^{18}$F, $^{125}$I, $^{82}$Br, $^{123}$I, $^{131}$I, $^{75}$Br, and $^{77}$Br,
(2) —CN,
(3) —$C_{1-4}$alkyl
(4) —O—$C_{1-4}$alkyl, wherein alkyl and cyano contain one $^{11}$C radionuclide or alkyl is substituted with one to three $^{18}$F atoms, and alkyl is unsubstituted or substituted with one or two fluoro substituents.

In a subclass of this class, $X^1$ is hydrogen, Y and Z are hydrogen, and X is selected from:
(1) $^3$H,
(2) $^{18}$F,
(3) cyano, wherein the carbon is $^{11}$C,
(4) —$CH_2$—$^{18}$F,
(5) —O—$^{11}CH_3$,
(6) —$OCH_2$—$^{18}$F,
(7) —OC—$(^2H)_2$—$^{18}$F, and
(8) —$OCH_2CH_2$—$^{18}$F.

In yet another subclass of this class, $X^1$ is hydrogen and Y and Z are hydrogen, and X is —$OCH_2CH_2$—$^{18}$F.

In another embodiment of the present invention, $X^1$ is the radionuclide $^3$H and Y and Z are hydrogen and X is selected from:
(1) a radionuclide selected from the group consisting of $^3$H, $^{11}$C, $^{18}$F, $^{125}$I, $^{82}$Br, $^{123}$I, $^{131}$I, $^{75}$Br, $^{15}$O, $^{13}$N, $^{211}$At and $^{77}$Br,
(2) —CN,
(3) —$C_{1-4}$alkyl
(4) —O—$C_{1-4}$alkyl, wherein alkyl and cyano contain one $^{11}$C radionuclide or alkyl is substituted with one to three $^{18}$F atoms, and alkyl is unsubstituted or substituted with one or two fluoro substituents.

In one class of this embodiment, $X^1$ is the radionuclide $^3$H, Y and Z are hydrogen and X is the radionuclide $^3$H.

In an embodiment of the present invention $Ar^1$ is phenyl, $Ar^2$ is phenyl, $R^1$ is hydrogen, $R^2$ is $C_{1-2}$alkyl, $R^3$ is $C_{1-3}$alkyl-O—$R^d$, $X^1$ is hydrogen, X is —O—$^{11}CH_3$, $^{13}$O—$CH_2$—$^{18}$F, and —O—$CH_2CH_2$—$^{18}$F, Y is hydrogen, and Z is hydrogen.

In yet another embodiment the present invention is directed to the compounds N-{[2-(3-cyanophenyl)-3-[4-([$^{18}$F]-2-fluoroethoxy)phenyl]-1-methylpropyl}-2-(5-trifluoromethyl-2-pyridyloxy)-2-methylpropanamide, which may be depicted as:

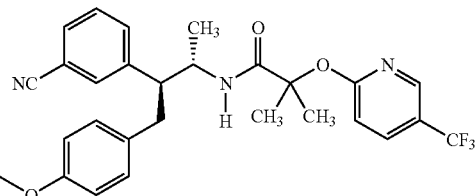

and N-{[2-(3cyanophenyl)-3-[4-([$^{18}$F]-2-fluoroethoxy)phenyl]-1-methylpropyl}-2-(5-methyl-2-pyridyloxy)-2-methylpropanamide, which may be depicted as:

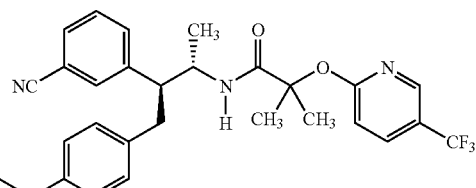

In yet another embodiment, the present invention is directed to the use of the compounds N-{2-(3-cyanophenyl)-3-[(4-ethoxy)phenyl]-1-methylpropyl}-2-(5-trifluoromethyl-2-pyridyloxy)-2-methylpropanamide, which may be depicted as:

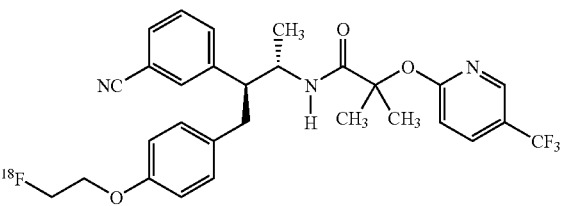

and N-{2-(3-cyanophenyl)-3-[(4-ethoxy)phenyl]-1-methylpropyl}-2-(5-methyl-2-pyridyloxy)-2-methylpropanamide, which may be depicted as:

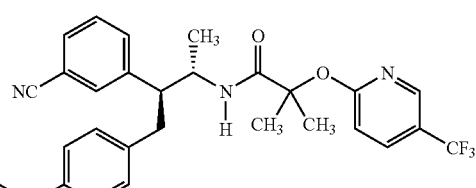

as starting materials for the synthesis of particular compounds of the present invention.

"Alkyl", as well as other groups having the prefix "alk", such as alkoxy, alkanoyl, means carbon chains which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono or bicyclic carbocyclic rings, each having from 3 to 10 carbon atoms. Examples of cycloalkyl include cyclopropyl, cyclobutyl, cyclopentyl, cyclohexyl, cycloheptyl, clooxtyl, tetrahydronaphthyl, decahydronaphthyl, and the like.

"Aryl" means mono- or bicyclic aromatic rings containing only carbon atoms. Examples of aryl include phenyl, naphthyl, and the like.

"Heteroaryl" means a aromatic ring containing at least one heteroatom selected from N, O and S, containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, and the like. The heteroaryl ring may be substituted on one or more carbon atoms. In one embodiment of the present invention, heteroaryl is pyridyl, and pyrimidyl. In one class of this embodiment, heteroaryl is pyridyl.

"Cycloheteroalkyl" means saturated rings containing at least one heteroatom selected from N, S and O, each of said ring having from 3 to 10 atoms in which the point of attachment may be carbon or nitrogen. Examples of "cycloheteroalkyl" include pyrrolidinyl, piperidinyl, piperazinyl, imidazolidinyl, pyranyl, tetrahydrofuranyl, morpholinyl, dioxanyl, oxanyl, azetidinyl, perhydroazepinyl, tetrahydrofuranyl, 1-thia-4-aza-cyclohexane(thiomorpholinyl), hexahydrothienopyridinyl, thienopyridinyl, azacycloheptyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

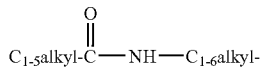

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

The present invention is also directed to a method for labeling cannabinoid-1 receptors in a mammal which comprises administering to a mammal in need of such labeling an effective amount of the radiolabeled compound of the present invention.

The present invention is also directed to a method for diagnostic imaging of cannabinoid-1 receptors in a mammal which comprises administering to a mammal in need of such diagnostic imaging an effective amount of the radiolabeled compound of the present invention.

The present invention is also directed to a method for diagnostic imaging of tissues bearing cannabinoid-1 receptors in a mammal which comprises administering to a mammal in need of such diagnostic imaging an effective amount of the radiolabeled compound of the present invention.

The present invention is also directed to a method for the diagnostic imaging of endocannabinoid binding sites in tissues of a mammalian species which comprises administering to the mammalian species in need of such diagnostic imaging an effective amount of the radiolabeled compound of the present invention.

The present invention is also directed to a method for diagnostic imaging of the brain in a mammal which comprises administering to a mammal in need of such diagnostic imaging an effective amount of the radiolabeled compound of the present invention.

The present invention is further directed to a method for the detection or quantification of cannabinoid-1 receptors in mammalian tissue which comprises administering to a mammal in which such quantification is desired an effective amount of the radiolabeled compound of the present invention.

In a preferred embodiment of the methods of the present invention, the mammal is a human.

The present invention is further directed to a process for the preparation N-{[2-(3-cyanophenyl)-3-[4-([$^{18}$F]-2-fluoroethoxy)phenyl]-1-methylpropyl}-2-(5-trifluoromethyl-2-pyridyloxy)-2-methylpropanamide, and N-{[2-(3-cyanophenyl)-3-[4-([$^{18}$F]-2-fluoroethoxy)phenyl]-1-methylpropyl}-2-(5-methyl-2-pyridyloxy)-2-methylpropanamide, comprising: contacting N-[2-(3-cyanophenyl)-3-(4-hydroxyphenyl)-1-methylpropyl]-2-(5-trifluoromethyl-2-pyridyloxy)-2-methylpropanamide and N-[2-(3-cyanophenyl)-3-(4-hydroxyphenyl)-1-methylpropyl]-2-(5-methyl-2-pyridyloxy)-2-methylpropanamide with an alkylating agent selected from [$^{18}$F]fluoroethyl bromide and [$^{18}$F]fluoroethyl tosylate in the presence of a weak base, such as cesium carbonate, in an inert solvent, such as dimethylformamide, at a temperature between room temperature and solvent reflux temperature, preferably about 100° C.

Suitable radionuclides that may be incorporated in the instant compounds include $^3$H (also written as T), $^{11}$C, $^{18}$F, $^{125}$I, $^{82}$Br, $^{123}$I, $^{131}$I, $^{75}$Br, $^{15}$O, $^{13}$N, $^{211}$At or $^{77}$Br. The radionuclide that is incorporated in the instant radiolabeled compounds will depend on the specific analytical or pharmaceutical application of that radiolabeled compound. Thus, for in vitro labeling of cannabinoid-1 receptors and competition assays, compounds that incorporate $^3$H, $^{125}$I or $^{82}$Br will generally be most useful. For diagnostic imaging agents, compounds that incorporate a radionuclide selected from $^{11}$C, $^{18}$F, $^{123}$I, $^{131}$I, $^{75}$Br, $^{76}$Br or $^{77}$Br are preferred. In certain applications incorporation of a chelating radionuclide such as Tc$^{99m}$ may also be useful. In the present invention, $^{18}$F is particularly preferred over $^{11}$C because with the longer half-life of $^{18}$F, imaging can be carried out long enough to allow a more specific signal to develop and improved conditions for receptor quantification studies.

Compounds that bind to receptors may elicit different responses. An agonist will elicit a response similar to the natural ligand, especially in terms of cell signalling and responses. These, in turn, will elicit a response in the organism being treated. An antagonist will bind to the receptor, thereby blocking the action of its ligand or other agonist, but will not elicit a response or cause and further changes in the target cell type. An inverse agonist will bind to a receptor, block agonist binding, and will elicit a response in the opposite direction of that elicited by the natural or endogenous ligand. In the case of the cannabinoind-1 receptor, its agonists cause a decrease in cyclic AMP formation and a decrease in calcium mobilization and chemical messenger release. A CB-1 receptor inverse agonist causes increased cyclic AMP activity and an increase in cellular signalling. The term receptor "modulator" is meant to include all ligands of a particular receptor regardless of the functional consequences of its binding and includes agonists, inverse agonists, and antagonists.

Radiolabeled cannabinoid-1 receptor modulators, when labeled with the appropriate radionuclide, are potentially useful for diagnostic imaging, basic research, and radiotherapeutic applications. Specific examples of possible diagnostic imaging and radiotherapeutic applications, include determining the location, the relative activity and/or the abundance of cannabinoid-1 receptors, radioimmunoassay of cannabinoid-1 receptor antagonists, agonists, and inverse agonists, and autoradiography to determine the distribution of cannabinoid-1 receptors in a mammal or an organ or tissue sample thereof.

In particular, the instant radiolabeled cannabinoid-1 receptor antagonists when labeled with the positron emitting radionuclide, F-18, are useful for positron emission tomographic (PET) imaging of cannabinoid-1 receptors in the brain of living humans and experimental animals. This radiolabeled cannabinoid-1 receptor antagonists may be used as research tools to study the interaction of unlabeled cannabinoid-1 antagonist with cannabinoid-1 receptors in vivo via competition between the labeled drug and the radiolabeled compound for binding to the receptor. This type of study is useful for determining the relationship between cannabinoid-1 receptor occupancy and dose of unlabeled cannabinoid-1 receptor modulator, as well as for studying the duration of blockade of the receptor by various doses of the unlabeled cannabinoid-1 receptor modulators. As a clinical tool, the radiolabeled cannabinoid-1 receptor modulators may be used to help define a clinically efficacious dose of a cannabinoid-1 receptor modulator. In animal experiments, the radiolabeled cannabinoid-1 receptor antagonists can be used to provide information that is useful for choosing between potential drug candidates for selection for clinical development. The radiolabeled cannabinoid-1 receptor modulators may also be used to study the regional distribution and concentration of cannabinoid-1 receptors in the living human brain, as well as the brain of living experimental animals and in tissue samples. The radiolabeled cannabinoid-1 receptor modulators may also be used to study disease or pharmacologically related changes in cannabinoid-1 receptor concentrations.

For example, positron emission tomography (PET) tracer such as the present radiolabeled cannabinoid-1 receptor modulators which can be used with currently available PET technology to obtain the following information: relationship between level of receptor occupancy by candidate cannabinoid-1 modulators and clinical efficacy in patients; dose selection for clinical trials of cannabinoid-1 modulators prior to initiation of long term clinical studies; comparative potencies of structurally novel cannabinoid-1 antagonists, agonists, or inverse agonists; investigating the influence of cannabinoid-1 modulators on ill vivo receptor affinity and density during the treatment of clinical targets with cannabinoid-1 receptor modulators and other agents; changes in the density and distribution of cannabinoid-1 receptors during e.g. psychiatric diseases or behaviorial disorders in their active stages, during effective and ineffective treatment and during remission; and changes in cannabinoid-1 receptor expression and distribution in CNS disorders (e.g. schizophrenia, cognitive dysfunctions, addictive behaviors, and eating disorders).

For the use of the instant compounds as exploratory or diagnostic imaging agents the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous.

Radiotracers labeled with short-lived, positron emitting radionuclides are almost always administered via intravenous injection within less than one hour of their synthesis. This is necessary because of the short half-life of the radionuclides involved (20 and 110 minutes for C-11 and F-18 respectively).

The terms "administration of" and or "administering a" compound should be understood to mean providing a compound of the invention or a prodrug of a compound of the invention to the individual to be imaged.

Any suitable route of administration may be employed for providing a mammal, especially a human, with an effective dosage of a compound of the present invention. For example, oral, rectal, topical, parenteral, ocular, pulmonary, nasal, and the like may be employed. For imaging, injection is preferred.

The pharmaceutical compositions of the present invention comprise a compound of Formula I as an active ingredient or a pharmaceutically acceptable salt thereof, and may also contain a pharmaceutically acceptable carrier. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the half life of the compound and the type of imaging. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed.

Among the suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The following are examples of representative pharmaceutical dosage forms for the compounds of Formula I:

| Injectable Suspension (I.M.) | mg/mL | Injectable Solution (I.V.) | concentration |
|---|---|---|---|
| Compound of Formula I | 10 | Compound of Formula I | 0.01 mg/mL |
| Methylcellulose | 5.0 | Tween 80 | 5 mg/mL |
| Tween 80 | 0.5 | Ethanol | 5 uL/mL |
| Benzyl alcohol | 9.0 | 0.9% saline | QS |
| Benzalkonium chloride | 1.0 | | |

Water for injection to a total volume of 1 mL.

The pharmaceutical compositions of this invention may be used in the form of a pharmaceutical preparation, for example, in solid, semisolid or liquid form, which contains one or more of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

A minimum dosage level for an unlabeled cannabinoid-1 receptor modulator to be evaluated for dosage selection is about 1 mg per day, preferably about 5 mg per day and especially about 10 mg per day. A maximum dosage level for the cannabinoid-1 receptor modulator is about 1500 mg per day, preferably about 1000 mg per day and especially about 500 mg per day.

When a radiolabeled cannabinoid-1 receptor modulator according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce emissions in the range of from about 1-10 mCi.

In one exemplary application, administration occurs in an amount of radiolabeled compound of between about 0.005 μg/kg of body weight to about 50 μg/kg of body weight per day, preferably of between 0.02 μg/kg of body weight to about 3 μg/kg of body weight. A particular analytical dosage that comprises the instant composition includes from about 0.5 μg to about 100 μg of a labeled cannabinoid-1 receptor modulator. Preferably, the dosage comprises from about 1 μg to about 50 μg of a radiolabeled cannabinoid-1 receptor modulator.

The following illustrative procedure may be utilized when performing PET imaging studies on patients in the clinic. The subject undergoes a baseline scan as described below, after which, the subject is premedicated with unlabeled cannabinoid-1 receptor modulator (at doses 300, 100, or 30 mg/day) for 2 weeks prior to the day of the follow-up PET experiment and is fasted for at least 12 hours allowing water intake ad libitum. A 20 G two inch venous catheter is inserted into the contralateral ulnar vein for radiotracer administration.

The subject is positioned in the PET camera and a tracer dose of [$^{15}$O]H$_2$O administered via i.v. catheter. The image thus obtained is used to insure that the patient is positioned correctly to include the brain or other areas of interest. Subsequently the [$^{18}$F] cannabinoid-1 receptor modulator (<20 mCi) is administered via i.v. catheter. Within ten minutes of the injection of radiotracer and at the end of the imaging session, 1 mL blood samples are obtained for determining the plasma concentration of the clinical candidate.

For determining the distribution of radiotracer, regions of interest (ROIs) are drawn on the reconstructed image including, e.g. the brain and the central nervous system. These regions are used to generate time activity curves obtained in the absence of receptor antagonist or in the presence of the clinical candidate to be evaluated at the various doses examined. Data are expressed as radioactivity per unit time per unit volume (nCi/cc/mCi injected dose). Inhibition curves are generated from the data obtained in a region of interest obtained starting at 70 minutes post-injection of radiotracer The ID$_{50}$ values are obtained by curve fitting the dose-rate/inhibition curves with equation i:

$$B = A_0 - A_0 * I/(ID_{50} + I) + NS \qquad (i)$$

where B is the %-Dose/g of radiotracer in tissues for each dose of clinical candidate, $A_0$ is the specifically bound radiotracer in a tissue in the absence of a cannabinoid-1 receptor modulator, I is the injected dose of modulator, ID$_{50}$ is the dose of compound which inhibits 50% of specific radiotracer binding to a cannabinoid receptor, and NS is the amount of non-specifically bond radiotracer.

microPET Camera Imaging

Two rats are anesthetized (ketamine/ace-promazine), positioned in the camera, and their tail veins canulated for ease of injection. One rat is preinjected with an unlabeled cannabinoid-1 receptor modulator 30 min. prior to injection of radiotracer to demonstrate non-specific binding. 150 uCi/rat of an $^{18}$F labeled cannabinoid-1 receptor modulator is injected via its tail vein, and the catheters flushed with several mLs of normal saline. Acquisition of images is started as the radiotracer was injected. Sixty, one minute images are acquired and the rats are subsequently euthanized with sodium pentobarbital. Regions of interest (ROIs) are drawn on the a summed image which includes the brain, then used to analyze the count rates in subsequent images. ROIs are defined to remain fairly clear during the course of the study, and are assumed to be representative of the entire organ. Count-rates are converted to %-dose/ROI by dividing the count-rate in the ROI by that of the whole rat, which is then multiplied by 100.

PET Imaging in Rhesus Monkey:

A fasted Rhesus monkey (7-11 kg) is anesthetized with ketamine I.M. (10 mpk) and the monkey is placed in the PET camera bed. I.V. catheters are inserted into the saphenous and cephalic veins. Subsequent anesthesia is maintained with Propofol using an induction dose is 5 mg/kg I.V followed by an infusion at 0.4 mg/kg/min for the duration of the study. Following the initial induction with Propofol, the animal is intubated and placed on ventilated medical grade compressed air at approximately 100 cc/breath, and 23 respirations per minute. A temperature probe, pulse oximeter, and end tidal CO$_2$ monitor are connected. Body temperature is maintained by placing the animal on a K-module heating pad and placing another pad on top and the animal is positioned inside the camera gantry supine, head first. An aliquot of PET ligand is injected IV with emission imaging begining at the time of injection and continuing for 2-3 hours.

One-half mL samples of blood are taken for metabolite correction and determination of radioactivity in plasma and whole blood at 0, 5, 15, 30, 60, 90, 120, 150, and 180 minutes. After 2 hours, a bolus of unlabeled CB1R modulator under study is given over 5 minutes, followed by an infusion of additional unlabeled CB1R modulator for 2 hours. Stock solution=0.8 mg/mL in 15% ETOH, 40% PEG400, 45% water. One mL plasma samples are taken for plasma drug concentration determinations at 0, 15, 30, 60, 90, 120, 150 and 180 minutes. One hour later, an aliquot of PET ligand is injected IV and emission imaging begins at the time of injection and continues for 2 hours. Occupancy is determined by comparing tracer binding in various regions of the brain after dosing with the CB-1R inverse agonist, to tracer binding in the same regions of the brain prior to dosing with the CB1 antagonist.

PET Imaging in Dogs

Female beagle dogs weighing 7.7-14.6 kg (11.0±2.3 kg) are fasted for at least 12 hours allowing water intake ad libitum. A 20 G two inch venous catheter is placed into the right front leg ulnar vein through which anesthesia is introduced by sodium pentobarbital 25-30 mg/kg in 3-4 mL and maintained with additional pentobarbital at an average dose of 3 mg/kg/hr. Another catheter is inserted into the contralateral ulnar vein for radiotracer administration.

Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring (Spacelabs™, model 90603A). EKG, heart rate, and core temperature are monitored continuously. In particular, EKG is observed for ST segment changes and arrhythmias.

The animal is positioned in the PET camera and a tracer dose of [$^{15}$O]H$_2$O administered via i.v. catheter. The image thus obtained is used to insure that the dog is positioned correctly to include the brain and other areas of interest. Subsequently [$^{18}$F]-cannabinoid-1 receptor modulator (<20 mCi) is administered via i.v. catheter. Following the acquisition of the total radiotracer image, an infusion is begun of the unlabeled cannabinoid-1 receptor modulator at one of three dose rates (0.1, 1 or 3 mpk/day). After infusion for 2.5 hrs, [$^{18}$F]-cannabinoid-1 receptor modulator is again injected via the catheter. Images are again acquired for up to 90 min. In one imaging session, a dose of 10 mpk another cannabinoid-1 receptor modulator is infused over 5 minutes. This dose has been determined to completely block radiotracer binding and thus is used to determine the maximum receptor-specific signal obtained with the PET radiotracer. At the conclusion of the study, animals are recovered and returned to animal housing.

For uninhibited distribution of radiotracer, regions of interest (ROIs) are drawn on the reconstructed image including the brain. These regions are used to generate time activity curves obtained in the absence of test compound or in the presence of test compound at the various infusion doses examined. Data are expressed as radioactivity per unit time per unit volume (nCi/cc/mCi injected dose). Inhibition curves are generated from the data obtained in a region of interest obtained starting at 70 min. post-injection of radiotracer. By this time, clearance of non-specific binding will have reached steady state. The ID$_{50}$ are obtained by curve fitting the dose-rate/inhibition curves with equation i, hereinabove.

Abbreviations used in the following Schemes and Examples: Ac: acyl; aq or aq.: aqueous; API-ES: atmospheric pressure ionization-electrospray (mass spectrum term); BOC or boc: tert-butoxycarbonyl;brine: saturated sodium chloride solution; Bu: butyl; DBU: 1,8-diazabicyclo[5.4.0]undec-7-ene; DEAD: diethyl azodicarboxylate; DIBAL-H: diisobutyl aluminum hydride; DMAP: 4-dimethylaminopyridine; DMF: dimethylformamide; DMSO: dimethylsulfoxide; DSC: differential scanning calorimetry; EDC: 1-ethyl-3-(3,3-dimethylaminopropyl)-carbodiimide hydrochloride; Et: ethyl; EtOAc: ethyl acetate; g or gm: gram; h or hr: hours; Hex: hexane; HOAc: acetic acid; HOBT: 1-hydroxybenzotriazole; HPLC: high pressure liquid chromatography; HPLC/MS: high pressure liquid chromatography/mass spectroscopy;in vacuo: rotoevaporation; IPAC or IPAc: isopropyl acetate; iPr: isopropyl; KHMDS: potassium hexamethyldisilazide; LC: Liquid chromatography; LC-MS or LCMS: liquid chromatography-mass spectrum; LDA: lithium diisopropyl amide; LHMDS: Lithium Hexamethyl Disilylamide-LiN(SiMe$_3$)$_2$; M: molar; Me: methyl; mg: milligram; MHz: megahertz; min: minutes; mL: milliliter; mmol: millimole; MPLC: medium pressure liquid chromatography; MS or ms: mass spectrum; Ms: mesyl (methane sulfonyl); N: normal; NaHMDS: sodium hexamethyldisilazide; N/A: Not applicable; NMR: nuclear magnetic resonance; PCy$_3$: tricyclohexylphosophine; Pd$_2$(dba)$_3$: tris(dibenzylideneacetone)dipalladium; Ph: phenyl; psi: pounds per square inch; PyBOP: (benzotriazol-1-yloxy)tripyrrolidinophosphonium hexafluorophosphate; rt or RT: room temperature; R$_t$: retention time; TFA: trifluoroacetic acid; TB: tetrahydrofuran; TLC: thin layer chromatography; uL, ul, μL or μl: microliter; UV: ultraviolet; XRPD: X-ray powder diffraction pattern.

Cannabinoid-1 receptor modulator which incorporate a radionuclide may be prepared by first synthesizing an unlabeled compound that optionally incorporates a iodo or bromo moiety and then exchanging a hydrogen or halogen moiety with an appropriate radionuclide using techniques well known in the art. Alternately, a radiolabeled cannabinoid-1 receptor modulator may be prepared by alkylation with a radiolabeled alkylating agent. Syntheses of labeled and unlabeled cannabinoid-1 receptor modulators are described below.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, a tert-butoxycarbonyl group may be reomoved by hydrogen chloride gas in a solvent such as ethyl acetae or dioxane; benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures.

Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

In some cases the order of carrying out the following reaction schemes may be varied to facilitate the reaction or to avoid unwanted reaction products.

Compounds of the present invention may be prepared by procedures illustrated in the accompanying schemes.

Scheme 1.

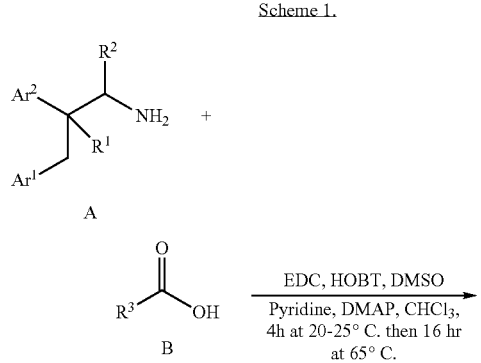

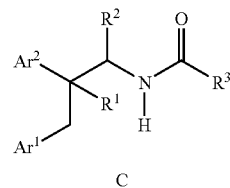

In Scheme 1, an appropriately substituted amine A is reacted with a carboxylic acid B under standard amide bond forming conditions to afford the arylamide C.

In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

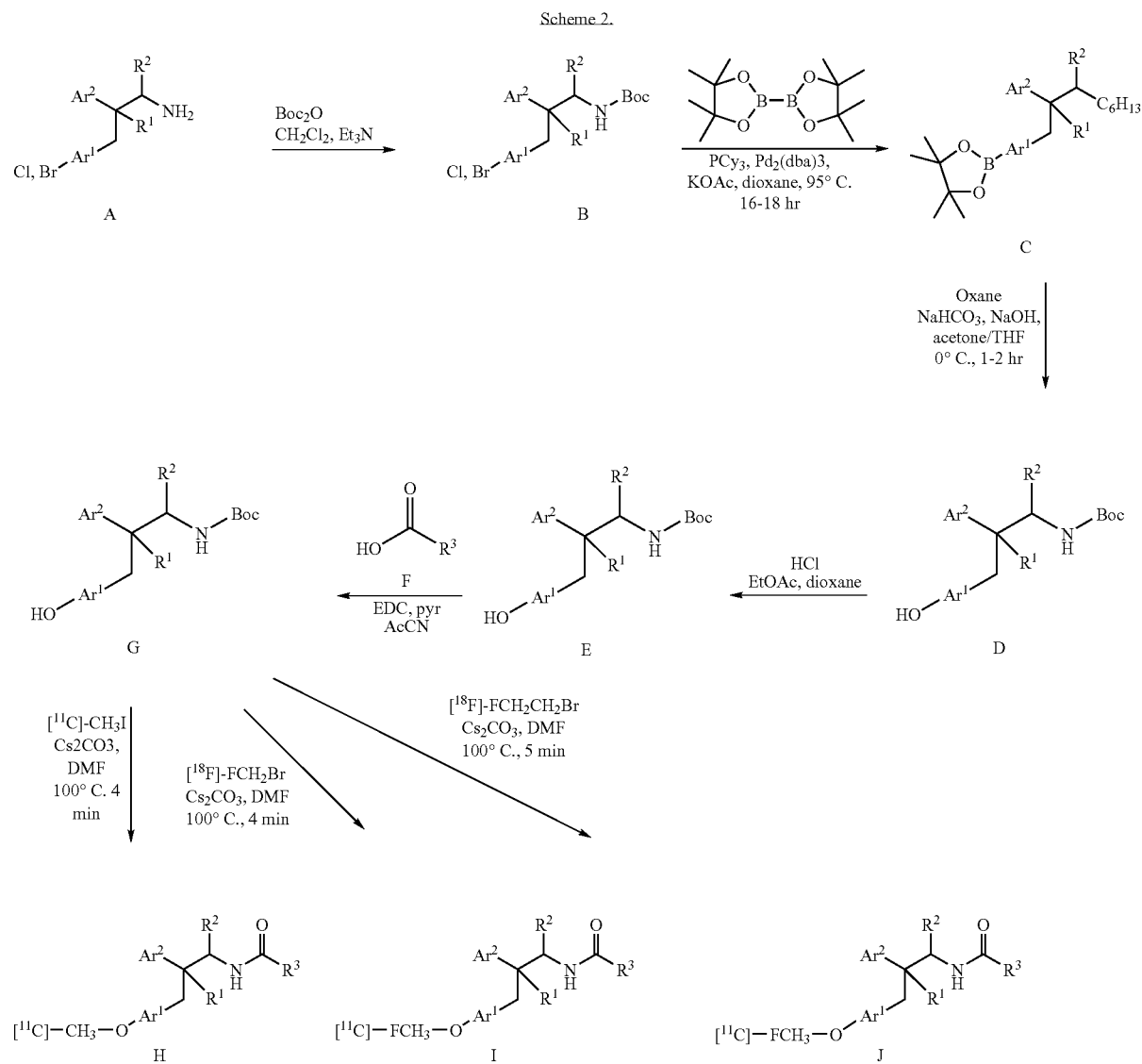

In Scheme 2, a halo-substituted aryl amine A is treated with an appropriate amine protecting reagent (eg., Boc anhydride) to afford N-Boc-amine B. The halide in B is reacted in the presence of a suitable palladium catalyst, phosphine, and base with bis(pinacolato)diboron to afford aryl-boronate C. The boronate C is oxidized with a persulfate reagent (Oxone) in acetone to yield phenol D. The N-Boc group in D is removed in the presence of acid to yield amine E which is coupled with acid F to afford phenolic amide G. The phenol in G is alkylated in the presence of base with an appropriate radionucleide-containing reagent, such as [$^{11}$C]-methyl iodide, [$^{18}$F]-fluoromethylbromide, or [18F]-fluoroethylbromide, to afford ethers H, I, or J, respectively.

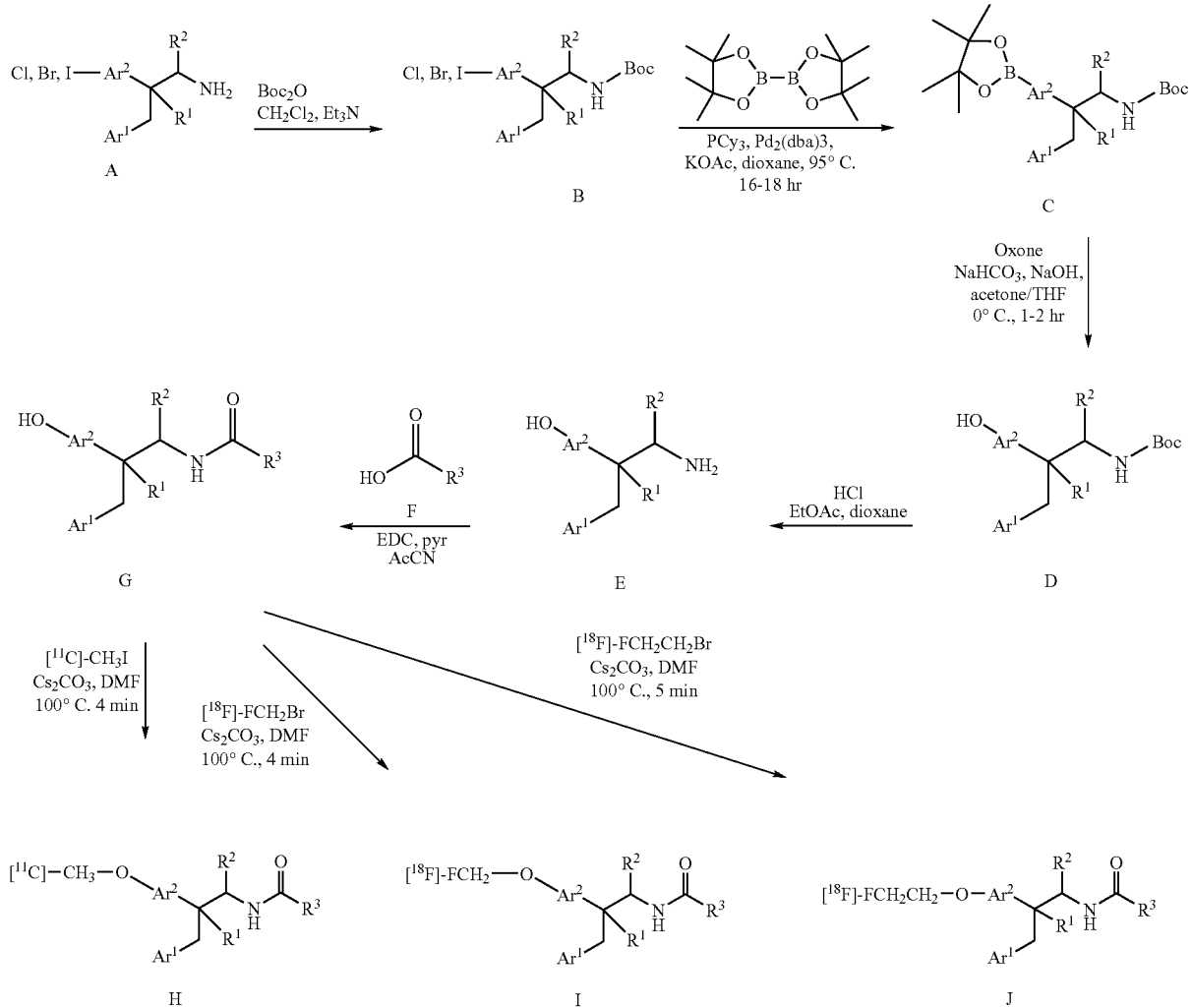

Likewise, in Scheme 3, a halo-substituted aryl amine A is treated with an appropriate amine protecting reagent (eg., Boc anhydride) to afford N-Boc-amine B. The halide in B is reacted in the presence of a suitable palladium catalyst, phosphine, and base with bis(pinacolato)diboron to afford aryl-boronate C. The boronate C is oxidized with a persulfate reagent (Oxone) in acetone to yield phenol D. The N-Boc group in D is removed in the presence of acid to yield amine E which is coupled with acid F to afford phenolic amide G. The phenol in G is alkylated in the presence of base with an appropriate radionucleide-containing reagent, such as [$^{11}$C]-methyl iodide, [$^{18}$F]-fluoromethylbromide, or [$^{18}$F]-fluoroethylbromide, to afford ethers H, I, or J, respectively.

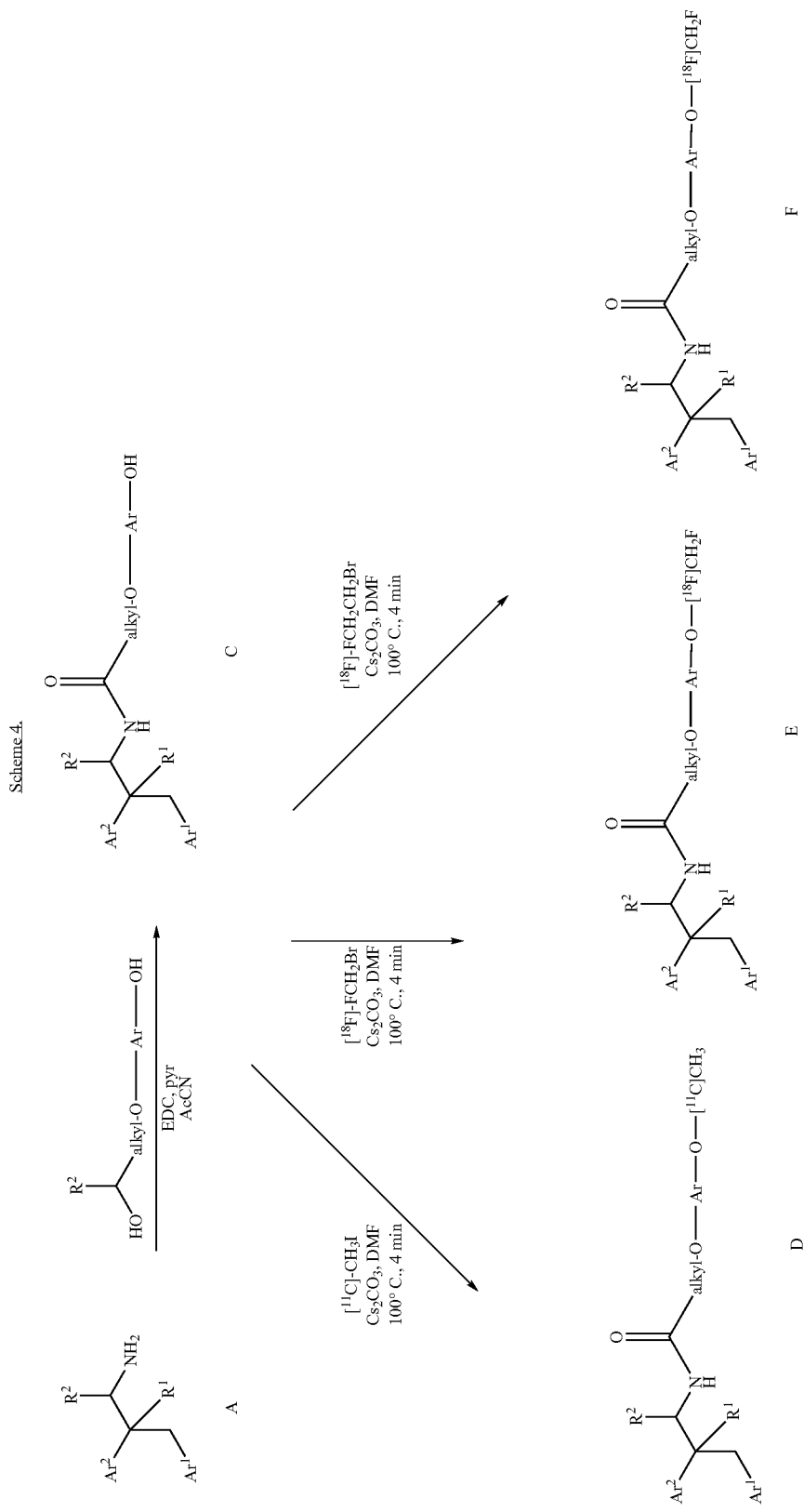

Alternatively, as shown in Scheme 4, amine A is acylated with an aromatic carboxylic acid B that contains a hydroxyl group to form amide C. The aromatic alcohol in C is alkylated in the presence of base with an appropriate radionucleide-containing reagent, such as [$^{11}$C]-methyl iodide, [$^{18}$F]-fluoromethylbromide, or [$^{18}$F]-fluoroethylbromide, to afford ethers D, E, or F, respectively.

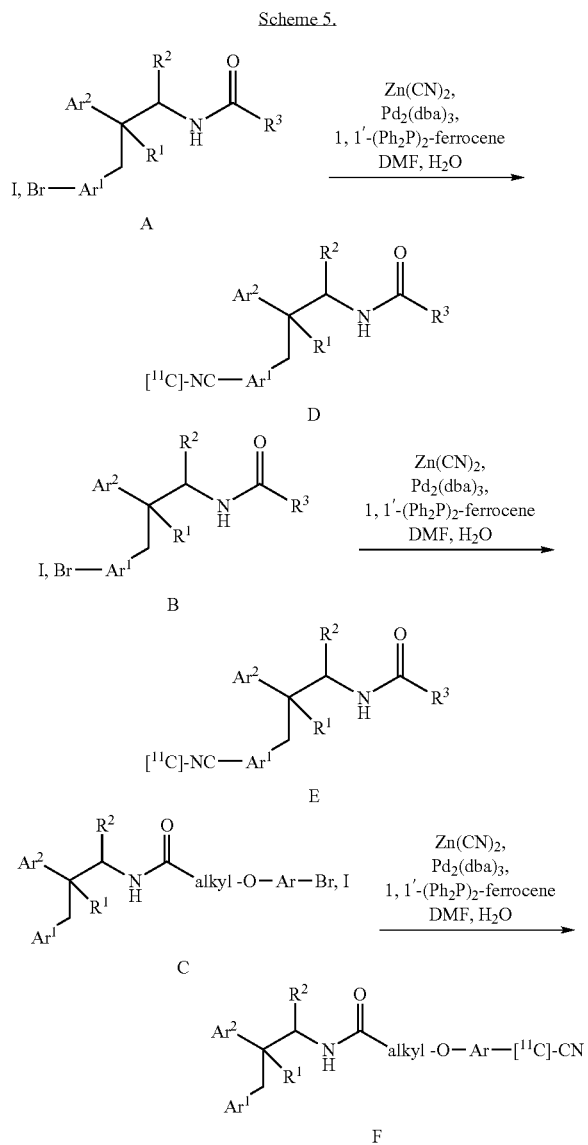

As outlined in Scheme 5, halogen-containing amides A, B, or C are treated with [$^{11}$C]-cyanide, tris(dibenzylidene acetone)dipalladium chloroform complex, 1,1'-bis(diphenylphosphino)ferrocene in aqueous DMF to afford the [$^{11}$C]-arylnitriles D, E, or F, respectively.

The following examples are provided for the purpose of further illustration only and are not intended to be limitations on the disclosed invention.

General Procedures.

The LC/MS analyses were performed using a MICROMASS ZMD mass spectrometer coupled to an AGILENT 1100 Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in CDCl$_3$ or CD$_3$OD as indicated and chemical shifts are reported as δ using the solvent peak as reference and coupling constants are reported in hertz (Hz).

REFERENCE EXAMPLE 1

[$^{18}$F]fluorobromomethane and [$^{18}$F]fluorobromomethane-d$_2$

Step A Radionuclide Production ([$^{18}$F]fluoride)

$^{18}$F$^-$ was obtained via the nuclear reaction $^{18}$O(p,n)$^{18}$F. This was achieved by bombarding a silver target containing $^{18}$O enriched water with accelerated protons (11 MeV). A Cyclotron (Siemens RDS 111 cyclotron) and systems for the production of primary labelled precursor are used for the radionuclide production. The [$^{18}$F]F$^-$ was placed on an anion exchange resin for transportation to the radiochemistry laboratories.

Step B Removal of Water from $^{18}$F$^-$

The [$^{18}$F]F$^-$ resin was eluted with 1.5 mL of a solution of 80:20 MeCN:potassium oxalate (aq). The potassium oxalate solution was made by combining 0.05 mL of (200 mg K$_2$C$_2$O$_4$/3 mg K$_2$CO$_3$/5 mL H$_2$O)+0.25 mL H$_2$O+1.2 mL MeCN. This aqueous [$^{18}$F]F$^-$ solution was treated with 0.2 mL Kryptofix222 (36 mg/mL MeCN). The solvent was removed under vacuum/heat/argon flow and the [$^{18}$F]-KF was further dried by 3 azeotropic distillations with acetonitrile (around 3×0.7 ml) at 95-115° C. This drying process may also be done using microwave heating under argon flow.

Step C Synthesis of [$^{18}$F]fluorobromomethane or [$^{18}$F]fluorobromomethane-d$_2$ The labelling precursor [$^{18}$F]FCH$_2$Br (or [$^{18}$F]FCD$_2$Br) was synthesized from dibromomethane or dibromomethane-d$_2$ via a nucleophilic substitution reaction, using a phase transfer catalyst (Kryptofix-2.2.2). The residue obtained after removal of the target water was treated with a solution of CH$_2$Br$_2$ (or CD$_2$Br$_2$) (0.05 mL) in MeCN (1 mL) and the reaction was heated to 95° C. An argon stream was used to distill the [$^{18}$F]FCH$_2$Br (or [$^{18}$F]FCD$_2$Br) into a vessel containing the precursor to be alkylated.

REFERENCE EXAMPLE 2

2-[$^{18}$F]fluorobromoethane

The residue obtained after drying of the [$^{18}$F]-KF was treated with a solution of bromoethyltriflate (5 μL) in 1,2-dichlorobenzene (0.7 mL) and heated at 115° C. under an argon stream. The [$^{18}$F]FCH$_2$CH$_2$Br produced was distilled out of the reaction apparatus into the solution containing the precursor to be alkylated.

REFERENCE EXAMPLE 3

[$^{11}$C]iodomethane

[$^{11}$C]CO$_2$ was produced using a Siemens RDS-111 cyclotron. An N-14 gas target containing 5% oxygen is irradiated with an 11 MeV proton beam generating [$^{11}$C]CO$_2$. The [$^{11}$C]CO$_2$ was trapped at room temperature inside ⅛" o.d. copper tubing packed with carbosphere, isolated from the atmosphere by switching a four-port, two-way valve, and set inside a lead container. The [$^{11}$C]CO$_2$ was transported to the radiochemistry laboratory and converted to [$^{11}$C]MeI using a GE Medical Systems PETtrace MeI Microlab.

REFERENCE EXAMPLE 4

N-(1S, 2S)-[3-(4-Chlorophenyl)-2-(3-cyanophenyl)-1-methylpropyl]amine hydrochloride Step A 3-(4-Chlorophenyl)-2-(3-bromophenyl)propanoic acid, (S)-methylbenzylamine Salt To a solution of 3-bromophenylacetic acid (3.3 kg, 15 mol) and p-chlorobenzyl chloride (2.6 kg, 16 mol) in 6.5 L of THF at −28° C. was added lithium bis(trimethylsilyl)amide (1 M in tetrahydrofuran, 31 L, 31 mol). The reaction mixture was aged at 0° C. for 2 h, and was then quenched with 2.5 N HCl (18 L). The organic layer was washed with water (8 L), concentrated on a rotary evaporator, and the residue was diluted with 10 L of toluene. (S)-methylbenzylamine was then added, and the precipitate was collected by filtration and dried under a nitrogen current for 12 h to give the salt of the racemic acid. Recrystallization from methanol provided the title compound.

Step B 4-(4-Chlorophenyl)-3-(3-bromophenyl)-2-butanone

To 3-(4-chlorophenyl)-2-(3-bromophenyl)propanoic acid, (S)-methylbenzylamine salt (2.2 kg, 4.7 mol) in toluene (39 L) and water (38 L) was added 5 N HCl (1.5 L). After stirring for 30 min, the organic layer was separated and concentrated to 20 L, and was added N,N-dimethylformamide (16 ml) and oxalyl chloride (0.49 L, 5.6 mol) over 1 h. After stirring for 30 min, the resulting crude acyl chloride was slowly transferred into a mixture of water (13 L), potassium carbonate (2.6 kg, 19 mol) and N-methoxy-N-methylamine hydrochloride (0.69 kg, 7.1 mol). After stirring for 30 min, the reaction was diluted with water (12 L), and the organic layer was separated, dried over sodium sulfate and concentrated to an oil, which was used without further purification. To the oil thus obtained in toluene (16 L) and tetrahydrofuran (5 L) at 10° C. was added methylmagnesium chloride (3 M in tetrahydrofuran, 2.0 L, 6.0 mol) over 1 h. After stirring for 30 min, the reaction was quenched by addition of 47 L of 20% aqueous ammonium chloride until the pH reached 7.5. The organic layer was separated, washed with water (16 L), dried over sodium sulfate and concentrated to give the title compound as an oil. $^1$H NMR (500 MHz, CD$_3$OD): δ 7.40 (d, 1H), 7.36 (s, 1H), 7.28-7.10 (m, 4H), 7.04 (d, 2H), 4.06 (dd, 1H), 3.28 (dd, 1H), 2.84 (dd, 1H), 2.03 (s, 3H).

Step C 4-(4-Chlorophenyl)-3-(3-bromophenyl)-2-butanol

To a solution of 4-(4-chlorophenyl)-3-(3-bromophenyl)-2-butanone (1.55 kg, 4.6 mol) in tetrahydrofuran (8.4 L) at −60° C. was added L-selectride (1.0 M in tetrahydrofuran, 5.3 L, 5.3 mol), and the reaction mixture was allowed to slowly warm up to room temperature overnight. The mixture was cooled back to 0° C., and was quenched by slow addition of acetone, aqueous sodium hydroxide (2.5 N, 8.5 L, 21 mol) and 30% hydrogen peroxide (2.1 L, 21 mol). After stirig at room temperature for 13 h, the reaction mixture was diluted with toluene (30 L). The organic layer was separated, washed with water (2×12 L), and concentrated to give the title compound as an oil. $^1$H NMR (500 MHz, CD$_3$OD): δ 7.40 (s, 1H), 7.30 (d, 1H), 7.28-7.10 (m, 4H), 7.04 (d, 2H), 3.98 (m, 1H), 3.12 (dd, 1H), 2.90 (dd, 1H), 2.80 (m, 1H), 1.08 (d, 3H).

Step D 4-(4-Chlorophenyl)-3-(3-cyanophenyl)-2-butanol

To a solution of 4-(4-chlorophenyl)-3-(3-bromophenyl)-2-butanol (1.5 kg, 4.6 mol) in dimethylformamide/water (volume ratio 99:1, 15 L total) was added zinc cyanide (0.39 kg, 3.3 mol), 1,1'-bis(diphenylphosphino)ferrocene (115 g, 0.21 mol) and tris(dibenzylideneacetone)dipalladium (76 g, 0.08 mol). The reaction mixture was stirred and degassed at room temperature for 1 h, and heated at 115° C. for 6 h before cooling to room temperature. Tributylphosphine (46 mL, 0.17 mol) was then added. After stirring for 1 h, the reaction was quenched with aqueous ammonia (1.56 L). After stirring for 1 h, the mixture was filtered through solka floc, and the cake was washed with isopropyl acetate. The filtrate was washed with water (5 L), and the aqueous layer was extracted with isopropyl acetate (4 L). The organic layers were combined, washed with water (10 L×2) and concentrated to give the title compound, which was used for the ensuing reaction after azeotroping with toluene.

Step E 4-(4-Chlorophenyl)-3-(3-cyanophenyl)-2-methylsulfonyloxybutane

To a solution of 4-(4-chlorophenyl)-3-(3-cyanophenyl)-2-butanol (1.0 kg, 3.5 mol) in toluene (10 L) at 0° C. was added triethylamine (684 mL, 4.9 mol) and methanesulfonyl chloride (353 mL, 4.6 mol). After stirring for 5 min, the reaction mixture was filtered, and the precipitate was washed with toluene (8 L). The filtrate was washed with sodium bicarbonate (6 L, 50% saturated aqueous solution) and water (3 L), and concentrated to give the title compound.

Step F 4-(4-Chlorophenyl)-3-(3-cyanophenyl)-2-azidobutane

To a solution of 4-(4-chlorophenyl)-3-(3-cyanophenyl)-2-methylsulfonyloxybutane (1.1 kg, 2.9 mol) in N,N-dimethylformamide (4.1 L) was added sodium azide (378 g, 5.8 mol), and the reaction was heated at 70° C. for 7 h. After cooling to room temperature, the reaction mixture was diluted with isopropyl acetate (11 L) and was washed with sodium bicarbonate (50% saturated aqueous solution) and water (5.5 L). The organic layer was separated and treated with Darco KB (254 g) overnight. The mixture was filtered over solka floc, washed with toluene and concentrated. The residue was diluted with toluene (1 L) and was loaded onto a silica gel pad, which was eluted with 90:10 hexane/ethyl acetate to give the title compound.

Step G N-(1S, 2S)-[3-(4-Chlorophenyl)-2-(3-cyanophenyl)-1-methylpropyl]amine

To a solution of 4-(4-chlorophenyl)-3-(3-cyanophenyl)-2-azidobutane (650 g, 2.1 mol) in isopropyl acetate (3.3 L) was added Lindlar's catalyst (130 g), and the mixture was hydrogenated at 40 psi at 45° C. for 24 h and at room temperature for anther 48 h. The reaction mixture was filtered over solka floc, and the cake was washed thoroughly with isopropyl acetate. The filtrate was partially concentrated to approximately 6 L, and was added hydrogen chloride in isopropyl acetate (5-6 N) while maintaining the reaction temperature at 18-25° C. After aging overnight, the precipitate was collected by filtration and washed twice with isopropyl acetate (1 L×2). The precipitate was suspended in isopropyl acetate (5.8 L) and was added aqueous potassium carbonate (1 M, 3.5 L). After stirring for 20 min, the organic layer was separated and concentrated to an oil, which was purified by preparative HPLC eluting on a Chiralpak AD column with heptane/ethanol/diethylamine (70/30/0.1; flow rate: 700 mL/min) to give the title compound.

The free amine thus obtained can be used directly or can be converted to the corresponding hydrochloride salt by treatment with hydrogen chloride in dioxane (4 N). LC-MS: m/e 285 (M+H)$^+$ (2.2 min).

REFERENCE EXAMPLE 5

N-[2-(3-Bromo-5-fluorophenyl)-3-(4-chlorophenyl)-1-methylpropyl]amine_hydrochloride (Diastereomer α)

Step A (3-Bromo-5-chlorophenyl)acetone

A mixture of 3,5-dibromofluorobenzene (50 g, 0.20 mol), isopropenyl acetate (22 mL, 0.20 mmol), tris(dibenzylideneacetone)dipalladium (1.8 g, 2.0 mmol) and 1,1'-bis(diphenylphosphino)ferrocene (4.4 g, 8.0 mmol) in 100 mL of toluene was heated at 100° C. under nitrogen for 2 h. The reaction mixture was cooled to room temperature and loaded onto a silica gel column, which was eluted with 0 to 40% ethyl acetate in hexane to afford the title compound.
$^{1}$H NMR (500 MHz, CD$_{3}$OD): δ 7.23 (d, 1H), 7.22 (s, 1H), 6.96 (d, 1H), 3.81 (s, 2H), 2.20 (s, 3H).

Step B 3-(3-Bromo-5-chlorophenyl)-4-(4-chlorophenyl)-2-butanone

To a vigorously stirred solution of (3-bromo-5-chlorophenyl)acetone (4.0 g, 17 mmol) and 4-chlorobenzyl chloride (2.2 g, 14 mmol) in 60 mL of acetonitrile at 0° C. was added cesium carbonate (11 g, 35 mmol), and the reaction was allowed to warm to room temperate overnight. The reaction mixture was partitioned between ethyl acetate (200 mL) and saturated aqueous ammonium chloride (200 mL). The organic layer was separated, dried over anhydrous sodium sulfate, filtered, and concentrated to dryness to afford the title compound. $^{1}$H NMR (500 MHz, CD$_{3}$OD): δ 7.21 (s, 1H), 7.19 (d, 2H), 7.04 (d, 2H), 6.97 (d, 1H), 6.87 (d, 1H), 4.16 (dd, 1H), 3.25 (dd, 1H), 2.86 (dd, 1H), 2.03 (s, 3H).

Step C 2-Azido-3-(3-bromo-5-fluorophenyl)-4-(4-chlorophenyl)butane

The title compound was prepared from 3-(3-bromo-5-fluorophenyl)-4-(4-chlorophenyl)-2-butanone following the procedures described in Reference Example 4, Step C, E and F.
$^{1}$H NMR (500 MHz, CD$_{3}$OD): δ 7.18 (s, 1H), 7.18 (d, 1H), 7.16 (d, 2H), 6.98 (d, 2H), 6.93 (d, 1H), 3.80 (m, 1H), 3.33 (m, 1H), 2.92-2.80 (m, 2H), 1.98 (d, 3H).

Step D 2-(N-tert-Butoxycarbonyl)amino-3-(3-bromo-5-fluorophenyl)-4-(4-chlorophenyl)butane To a solution of 2-azido-3-(3-bromo-5-fluorophenyl)-4-(4-chlorophenyl)butane (2.6 g, 7.1 mmol) in ethyl acetate (20 mL) was added di(tert-butyl)dicarbonate (2.0 g, 9.2 mmol) and platinum dioxide (0.26 g). The mixture was degassed and charged with hydrogen with a balloon. After stirring for 1 day, the reaction mixture was filtered through CELITE diatomaceous earth, and the filtrate was concentrated to give the crude product. $^{1}$H NMR (500 MHz, CD$_{3}$OD): δ 7.13 (d, 2H), 7.12 (d, 1H), 7.05 (s, 1H), 6.95 (d, 2H), 6.83 (d, 1H), 3.82 (m, 1H), 3.18 (dd, 1H), 2.87 (m, 1H), 2.77 (dd, 1H), 1.45 (s, 9H), 0.97 (d, 3H).

Step E N-[2-(3-Bromo-5-fluorophenyl)-3-(4-Chlorophenyl)-1-methylpropyl]amine hydrochloride (Diastereomer α)

To a solution of 2-(N-tert-butoxycarbonyl)amino-3-(3-bromo-5-fluorophenyl)-4-(4-chlorophenyl)butane in of ethyl acetate was added hydrogen chloride in dioxane (4 M). After stirring at room temperature for 30 min, the mixture was concentrated to dryness to give the title compound. LC-MS: m/e 356 (M+H)$^{+}$ (2.9 min).

REFERENCE EXAMPLE 6

N-[3-(4-Chlorophenyl)-2-(3-cyano-5-fluorophenyl)-1-methylpropyl]amine_hydrochloride (Diastereomer α)

Step A 2-(N-tert-Butoxcarbonyl)amino-3-(3-cyano-5-fluorophenyl)-4-(4-chlorophenyl)butane The title compound was prepared from 2-(N-tert-butoxycarbonyl)amino-3-(3-bromo-5-fluorophenyl)-4-(4-chlorophenyl)butane (Reference Example 5, Step D) following the procedure described for Reference Example 4, Step D. $^{1}$H NMR (500 MHz, CD$_{3}$OD): δ 7.32 (d, 1H), 7.28 (s, 1H), 7.21 (br d, 1H), 7.12 (d, 2H), 6.96 (d, 2H), 3.87 (m, 1H), 3.19 (dd, 1H), 3.04 (m, 1H), 2.83 (dd, 1H), 1.46 (s, 9M), 0.98 (d, 3H).

Step B N-[3-(4-Chlorophenyl)-2-(3-cyano-5-fluorophenyl)-1-methylpropyl]amine hydrochloride (Diastereomer α)

To a solution of 2-(N-tert-butoxycarbonyl)amino-4-(4-chlorophenyl)-3-phenylbutane (1.2 g, 3.0 mmol) in 4 mL of ethyl acetate was added hydrogen chloride in dioxane (4 M, 2 mL, 8 mmol). After stirring at room temperature for 30 min, the mixture was concentrated to dryness to give the title compound. LC-MS: m/e 303 (M+H)$^{+}$ (2.3 min).

REFERENCE EXAMPLE 7

N-[2-(3-Cyanophenyl)-3-(4-methoxyphenyl)-1-methylpropyl]amine hydrochloride (Diastereomer α)

Step A 3-Cyanophenylacetone

The title compound was prepared following the procedure described in Reference Example 5, Step A substituting 3,5-dibromofluorobenzene with 3-bromobenzonitrile and 1,1'-bis(diphenylphosphino)ferrocene with 2-(dicyclohexylphosphino)-2'-(N,N-dimethylamino)biphenyl at Step A. $^{1}$H NMR (500 MHz, CD$_{3}$OD): δ 7.6 (m, 1H), 7.56 (br s, 1H), 7.50-7.48 (m, 2H), 3.88 (s, 2H), 2.21 (s, 3H).

Step B N-[2-(3-Cyanophenyl)-3-(4-Methoxyphenyl)-1-methylpropyl]amine_hydrochloride (Diastereomer α)

The title compound was prepared following the procedures described for Reference Example 5, Step B to E substituting 3-bromo-5-chlorophenyl)acetone with 3-cyanophenylacetone and 4-chlorobenzyl chloride with 4-methoxybenzyl chloride at Step B. LC-MS: m/e 281 (M+H)$^{+}$ (3.2 min).

REFERENCE EXAMPLE 8

N-(1S, 2S)-[2-(3-Cyanophenyl)-3-(4-hydroxyphenyl)-1-methylpropyl]amine hydrochloride Step A (2S, 3S)-2-(N-tert-Butoxcarbonyl)amino-3-(3-cyanophenyl)-4-(4-chlorophenyl)butane To a solution of N-(1S, 2S)-[3-(4-chlorophenyl)-2-(3-cyanophenyl)-1-methylpropyl]amine (Reference Example 4, 5.3 g, 19 mmol) in dichloromethane (50 mL) at 0° C. was added di(tert-butyl)dicarbonate (4.9 g, 22 mol) and diisopropylethylamine (4.3 mL, 24 mmol). After stirring at room temperature overnight, the reaction mixture was diluted with ethyl acetate (200 mL), washed with water (200 mL×2) and brine and concentrated. The residue was purified by flash column chromatography on silica gel eluting with 0 to 25% ethyl acetate in hexane to give the title compound. $^{1}$H NMR (500 MHz, CD$_{3}$OD): δ 7.52 (m, 1 H), 7.45-7.36 (m, 3H), 7.11 (d, 2H), 6.93 (d, 2H), 3.90 (m, 1H), 3.22 (dd, 1H), 2.98 (m, 1H), 2.82 (dd, 1H), 1.48 (s, 9H), 0.95 (d, 3H).

Step B (2S, 3S)-2-(N-tert-Butoxycarbonyl)amino-3-(3-cyanophenyl)-4-(4-hydroxyphenyl)butane To a mixture of (2S, 3S)-2-(N-tert-butoxycarbonyl)amino-3-(3-cyanophenyl)-4-(4-chlorophenyl)butane (2.0 g, 5.2 mmol), bis(pinacolato)diboron (2.1 g, 8.4 mmol), potassium acetate (1.3 g, 13 mmol) and tricyclohexylphosphine (0.18 g, 0.63 mmol) under nitrogen was added anhydrous dioxane (20 mL), and tris(dibenzylideneacetone)dipalladium (0.24 g, 0.26 mmol) After flushing with nitrogen for 20 min, was added. The reaction was stirred at room temperature for 30 min and was then heated at 95° C. overnight. The reaction mixture was cooled to room temperature and partitioned between saturated sodium bicarbonate (100 mL) and ethyl acetate (100 mL). The organic layer was separated, washed with water and brine and concentrated to dryness. The residue was purified by flash column chromatography on silica gel eluting with 0-30% ethyl acetate in hexane to give the boronic ester (2.5 g). The boronic ester was then dissolved in acetone (25 mL) and tetrahydrofuran (25 mL), cooled with an ethanol/ice bath, and was addded water (25 mL) and sodium hydroxide (0.32 g 7.9 mmol)), sodium bicarbonate (3.5 g, 42 mmol). Oxone (3.2 g, 5.2 mmol) in 25 mL of water was added over 0.5 h, while keeping the reaction mixture below 5° C. After stirring at 0° C. for 10 min, the reaction was quenched by the addition of sodium bisulfite (2.2 g, 21 mmol). The reaction mixture was stirred for 15 min, and was partitioned between water (200 mL) and methyl tert-butyl ether (100 mL) and heptane (100 mL). The organic layer was separated, washed with water (200 mL) and brine and concentrated to dryness to give the title compound. $^1$H NMR (500 MHz, CD$_3$OD): δ 7.50 (m, 1 H), 7.38 (m, 3H), 6.75 (d, 2H), 6.56 (d, 2H), 3.88 (m, 1H), 3.14 (dd, 1H), 2.93 (m, 1H), 2.73 (dd, 1H), 1.48 (s, 9H), 0.94 (d, 3H).

Step C N-(1S, 2S)-[2-(3-Cyanophenyl)-3-(4-hydroxyphenyl)-1-methylpropyl]amine hydrochloride The title compound was prepared from (2S, 3S)-2-(N-tert-butoxycarbonyl)amino-3-(3-cyanophenyl)-4-(4-hydroxyphenyl)butane following the procedure described in Reference Example 5, Step E. LC-MS: m/e 267 (M+H)$^+$ (2.1 min).

REFERENCE EXAMPLE 9

N-(1S, 2S)-{2-(3-Cyanophenyl)-3-[4-(2-fluoroethoxy)phenyl]-1-methylpropyl}amine hydrochloride Step A (2S, 3S)-2-(N-tert-Butoxycarbonyl)amino-3-(3-cyanophenyl)-4-[4-(2-fluroethyoxy)phenyl]butane To a solution of (2S, 3S)-2-(N-tert-butoxycarbonyl)amino-3-(3-cyanophenyl)-4-(4-hydroxyphenyl)butane (Reference Example 8, 0.97 g, 2.7 mmol) in 20 mL of dimethylformamide was added cesium carbonate (1.3 g, 4.0 mmol) and 2-fluoroethyl methanesulfonate (0.75 g, 5.3 mmol). After stirring at 65° C. for 1 h, the reaction was cooled to room temperature, diluted with ether (200 mL), washed with water (200 mL×2) and brine and concentrated. The residue was purified by flash column chromatography on silica gel eluting with 0 to 40% ethyl acetate in hexane to give the title compound.

$^1$H NMR (500 MHz, CD$_3$OD): δ 7.50 (m, 1 H), 7.39 (m, 3H), 6.87 (d, 2H), 6.79 (br d, 1H), 6.71 (d, 2H), 4.70 (m, 1H), 4.60 (m, 1H), 4.12 (m, 1H), 4.08 (m, 1H), 3.90 (m, 1H), 3.18 (dd, 1H), 2.95 (m, 1H), 2.78 (dd, 1H), 1.48 (s, 9H), 0.95(d, 3H).

Step B N-(1S, 2S)-{2-(3-Cyanophenyl)-3-[4-(2-fluoroethoxy)phenyl]-1-methylpropyl}amine hydrochloride The title compound was prepared from 2-(N-tert-butoxycarbonyl)amino-3-(3-cyanophenyl)-4-[4-(2-fluroethyoxy)phenyl]butane following the procedure described in Reference Example 5, Step E. LC-MS: m/e 313 (M+H)$^+$ (2.4 min).

REFERENCE EXAMPLE 10

N-[2-(3-Cyano-5-fluorophenyl)-3-(4-hydroxyphenyl)-1-methylpropyl]amine hydrochloride (Diastereomer α)

The title compound was prepared from 2-(N-tert-butoxycarbonyl)amino-3-(3-cyano-5-fluorophenyl)-4-(4-chlorophenyl)butane (Reference Example 6, Step A) following the procedure described in Reference Example 8, Steps B and C. LC-MS: m/e 285 (M+H)$^+$ (2.0 min).

REFERENCE EXAMPLE 11

2-Methyl-2-(5-chloro-2-pyridyloxy)propionic acid

Step A Ethyl 2-Methyl-2-(5-chloro-2-pyridyloxy)propionate

A mixture of 5-chloro-2-hydroxypyridine (5.0 g, 39 mmol), ethyl 2-bromoisobutyrate (5.7 mL, 39 mmol) and cesium carbonate (25 g, 77 mmol) in 50 mL of acetonitrile was heated at 50° C. overnight. The volatile materials were removed by concentrating on a rotary evaporator, and the residue was partitioned between water (100 mL) and EtOAc (100 mL). The organic layer was separated and the aqueous layer extracted with EtOAc (2×100 mL). The combined organic extracts were dried over anhydrous sodium sulfate, filtered and concentrated to dryness, and the residue was purified by flash column chromatography on silica gel eluted with 5% EtOAc in hexane to give the title compound. $^1$H NMR (500 MHz, CD$_3$OD): δ 7.99 (d, 1H), 7.67 (dd, 1H), 6.68 (d, 1H), 4.13 (q, 2H), 1.64 (s, 6H), 1.14 (t, 3H). LC-MS: m/e 244 (M+H)$^+$ (3.41 min).

Step B 2-Methyl-2-(5-chloro-2-pyridyloxy)propionic Acid

A mixture of ethyl 2-methyl-2-(5-chloro-2-pyridyloxy) propionate (2.6 g, 11 mmol) and sodium hydroxide (0.85 g, 21 mmol) in 15 mL acetonitrile and 15 mL water was heated at 50° C. overnight. The volatile materials were removed by concentrating on a rotary evaporator, and the residue was partitioned between 2 M hydrochloric acid (100 mL) and ether (100 mL). The organic layer was separated, washed with water (2×50 mL), dried over anhydrous MgSO$_4$, filtered and concentrated to dryness to give the title compound. $^1$H NMR (500 MHz, CD$_3$OD): δ 8.02 (d, 1H), 7.65 (dd, 1H), 6.77 (d, 1H), 1.62 (s, 6H). LC-MS: m/e 216 (M+H)$^+$ (2.33 min).

REFERENCE EXAMPLE 12

2-Methyl-2-(5-methyl-2-pyridyloxy)propionic acid

The title compound was prepared from 5-methyl-2-hydroxypyridine following the procedure described for Reference Example 11. $^1$H NMR (500 MHz, CD$_3$OD): δ 7.85 (s, 1H), 7.47 (dd, 1H), 6.65 (d, 1H), 2.22 (s, 3H), 1.62 (s, 6H). LC-MS: m/e 196 (M+H)$^+$ (2.3 min).

REFERENCE EXAMPLE 13

2-Methyl-2-(4-trifluoromethyl-2-pyridyloxy)propionic Acid

The title compound was prepared following the procedures described for Reference Example 11 substituting 5-chloro-2-hydroxypyridine with 4-trifluoromethyl-2-hydroxpyridine at Step A. $^1$H NMR (500 MHz, CD$_3$OD): δ 8.30 (d, 1H), 7.18 (d, 1H), 7.05 (s, 1H), 1.71 (s, 6H).

REFERENCE EXAMPLE 14

2-Methyl-2-(6-trifluoromethyl-4-pyrimidyloxy)propionic Acid

The title compound was prepared following the procedures described for Reference Example 11 substituting 5-chloro-2-hydroxpyridine with 6-trifluoromethyl-4-hydroxpyrimidine at Step A. ¹H NMR (500 MHz, CD₃OD): δ 8.81 (s, 1H), 7.28 (s, 1H), 1.75 (s, 6H). LC-MS: m/e 251 (M+H)⁺ (2.1 min).

REFERENCE EXAMPLE 15

2-Methyl-2-(5-trifluoromethyl-2-pyridyloxy)propionic Acid

To a solution of potassium bis(trimethylsilyl)amide in tetrahydrofuran (0.91 M, 275 mL) at −70° C. under nitrogen and was added ethyl-2-hydroxyisobutyrate (36 mL, 34.7 g, 0.263 mol) over 12 min. After stirring for additional 10 min, 2-chloro-5-trifluormethylpyridine was added in one portion. The cooling bath was removed and the reaction was allowed to warm to room temperature overnight. Sodium hydroxide (105 mL, 5N) was added, and the reaction was refluxed overnight. The reaction mixture was partially concentrated on a rotary evaporator, diluted with water (150 mL), and extracted with hexane (2×150 L). The aqueous layer was separated and acidified with 2N HCl (350 mL, 0.7 mol), and the resulting suspension was cooled to 0° C. After aging for 20 min, the precipitate was collected by filtration, which was washed with water (4×150 mL) and air-dried to afford 38.0 g of a tan solid. (85.5%). Treatment with Darco KB and recrystallization in 3:1 heptane/isopropyl acetate provided the title compound as a white crystalline material. ¹H NMR (500 MHz, CD₃OD): δ 8.38 (br s, 1H), 7.93 (dd, 1H), 7.13 (d, 1H), 1.70 (s, 6H). LC-MS: m/e 250 (M+H)⁺ (2.6 min).

REFERENCE EXAMPLE 16

2-Methyl-2-(5-cyano-2-pyridyloxy)propionic Acid

Step A Methyl 2-methyl-2-(5-cyano-2-pyridyloxy)propionate

To a solution 2-methyl-2-(5-chloro-2-pyridyloxy)propionic acid (Reference Example 11, 1.0 g, 4.6 mmol) in dichloromethane (10 mL) and methanol (10 mL) at 0° C. was added trimethylsilyldiazomethane (2 M in hexane) until a yellow color persisted. After stirring at room temperature for 15 min, the reaction mixture was concentrated to dryness to give the crude methyl ester, which was used without further purification. Thus, the crude methyl ester was dissolved in acetonitrile (5 mL), and was added potassium cyanide (0.45 g, 7.0 mmol), tributyltin chloride (0.10 mL, 0.37 mmol). The mixture was degassed and was added tris(dibenzylideneacetone) dipalladium (0.15 g, 0.16 mmol) and tri(tert-butyl)phosphine (10% weight, 2.2 mL, 0.84 mmol), and was degassed two more times. After heating at 80° C. overnight. The reaction mixture was cooled to room temperature, diluted with dimethyl sulfoxide (5 mL) and water (2 mL) and filtered. The filtrate was loaded onto a reverse phase HPLC column eluting with 20 to 100% water in acetonitrile to give the title compound. ¹H NMR (500 MHz, CD₃OD): δ 8.43 (d, 1H), 7.97 (dd, 1H), 6.91 (d, 1H), 3.63 (s, 3H), 1.66 (s, 6 H)

Step B 2-Methyl-2-(5-cyano-2-pyridyloxy)propionic Acid

To a solution of methyl 2-methyl-2-(5-cyano-2-pyridyloxy)propionate (12 mg) in tetrahydrofuran (2 mL) and water (1 mL) was added lithium hydroxide monohydrate (10 mg). After stirring at room temperature overnight, the reaction mixture was acidified with 1 N hydrochloric acid, and the resulting mixture was partitioned between water (50 mL) and ethyl acetate (50 mL). The organic layer was separated, washed with water and brine, dried over sodium sulfate, filtered and concentrated to dryness to give the title compound. ¹H NMR (500 MHz, CD₃OD): δ 8.23 (d, 1H), 7.96 (dd, 1H), 6.91 (d, 1H), 1.64 (s, 6H).

REFERENCE EXAMPLE 17

2-Methyl-2-(5-fluoro-2-pyridyloxy)propionic Acid

Step A Benzyl 2-(5-Fluoro-2-pyridyloxy)propionate

To a mixture of 5-fluoro-2-hydroxypyridine (2.0 g, 18 mmol), benzyl lactate (3.2 g, 18 mmol) and triphenylphosphine (9.3 g, 35 mmol) in 50 mL of CH₂Cl₂ was added diisopropylazodicarboxylate (7.0 mL, 35 mmol) at 0° C. The reaction was allowed to warm to room temperature overnight. The resulting mixture was loaded onto a silica gel column, which was eluted with 0 to 25% EtOAc in hexane to give the title compound. ¹H NMR (500 MHz, CD₃OD): δ 7.81 (d, 1H), 7.50 (ddd, 1H), 7.36-7.26 (m, 5H), 6.85 (dd, 1H), 5.24 (q, 1H), 5.16 (ABq, 2H) 1.55 (d, 3H). LC-MS: m/e 276 (M+H)⁺ (3.6 mm).

Step B Benzyl 2-(5-Fluoro-2-pyridyloxy)-2-methylpropionate

To a solution of benzyl 2-(5-fluoro-2-pyridyloxy)propionate (2.9 g, 10 mmol) and methyl iodide (3.3 mL, 53 mmol) in 40 mL of anhydrous THF at −78° C. was added potassium hexamethyldisilazide (0.5 M in toluene, 32 mL, 16 mmol). The reaction was allowed to warm to room temperature over 3 h and was partitioned between saturated ammonium chloride (150 mL) and EtOAc (150 mL). The organic layer was separated and the aqueous layer extracted with EtOAc (2×50 mL). The combined organic extracts were dried over anhydrous sodium sulfate, filtered, and concentrated to dryness, and the residue was purified by flash column chromatography on silica gel eluted with 0 to 20% EtOAc in hexane to give the title compound. ¹H NMR (500 MHz, CD₃OD): δ 7.63 (d, 1H), 7.44 (ddd, 1H), 7.27 (m, 3H), 7.18 (m, 2H), 6.74 (dd, 1H), 5.09 (s, 2H) 1.64 (s, 6H). LC-MS: m/e 290 (M+H)⁺ (3.7 min).

Step C 2-(5-Fluoro-2-pyridyloxy)-2-methylpropionic Acid

A mixture of benzyl 2-(5-fluoro-2-pyridyloxy)-2-methylpropionate (2.6 g, 9.2 mmol) and 10% palladium on carbon (0.26 mg) in 20 mL MeOH was degassed and filled with hydrogen using a balloon. After stirring at room temperature for 3 h, the reaction mixture was filtered through CELITE diatomaceous earth and washed with MeOH (20 mL), and the filtrate was concentrated to dryness to give the title compound. ¹H NMR (500 MHz, CD₃OD): δ 7.91 (d, 1H), 7.48 (ddd, 1H), 6.78 (dd, 1H), 1.65 (s, 6H). LC-MS: m/e 200 (M+H)⁺ (2.6 min).

REFERENCE EXAMPLE 18

2-(2-Pyridyloxy)-2-methylpropionic Acid

The title compound was prepared following the procedures described for Reference Example 17 substituting 5-fluoro-2-hydroxypyridine with 2-hydroxypyridine at Step A. ¹H NMR (500 MHz, CD₃OD): δ 8.04 (dd, 1H), 7.64 (ddd, 1H), 6.89 (dd, 1H), 6.76 (dd, 1H), 1.66 (s, 6H). LC-MS: m/e 182 (M+H)⁺ (1.5 min).

REFERENCE EXAMPLE 19

2-Methyl-2-(4-methyl-2-pyridyloxy)propionic Acid

2-Methyl-2-(4-methyl-2-pyridyloxy)propionic Acid was prepared following the procedures described for Reference Example 17 substituting 5-fluoro-2-hydroxypyridine with 4-methyl-2-hydroxypyridine at Step A. $^1$H NMR (500 MHz, CD$_3$OD): δ 7.88 (d, 1H), 6.73 (d, 1H), 6.57 (s, 1H), 2.28 (s, 3H), 1.63 (s, 6H).

REFERENCE EXAMPLE 20

2-Methyl-2-(5-difluoromethyl-2-pyridyloxy)propionic Acid

Step A 4-Chloro-3-pyridinecarboxaldehyde

To a solution of 2-chloro-5-iodopyridine (18 g, 75 mmol) in ether (100 mL) and tetrahydrofuran (100 mL) at −78° C. was added tert-butyllithium (1.7 M in pentane, 60 mL, 100 mmol). After stirring at −78° C. for 30 min, N,N-dimethylformamide (11 mL, 150 mmol) was added, and the reaction was allowed to warm up to 0° C over 30 min, and was poured into a stirred mixture of ice (200 g), concentrated hydrochloric acid (20 mL) and ether (200 mL). The organic layer was separated, washed with water and brine, dried over anhydrous magnesium sulfate, filtered and concentrated to dryness. The residue was purified by flash column chromatography on silica gel eluting with 0 to 10% ether in hexane/dichloromethane (1:1) to give the title compound. $^1$H NMR (500 MHz, CD$_3$OD): δ 10.18 (s, 1H), 8.90 (s, 1H), 8.17 (d, 1H), 7.55 (d, 1H).

Step B 4-Chloro-3-difluoromethylpyridine

To a solution of 4-chloro-3-pyridinecarboxaldehyde (3.7 g, 26 mmol) in 15 mL of dichloromethane at −78° was added (dimethylamino)sulfur trifluoride (15 mL, 0.15 mol), and the reaction was allowed to warm up to room temperature overnight. The reaction was quenched by carefully transferring into a mixture of ice (100 g) and sodium sulfite (10 g). The product was extracted with ether (100 mL×2), and the combined extracts were washed with water and brine, dried over anhydrous magnesium sulfate, filtered and concentrated to dryness. The residue was purified by flash column chromatography on silica gel eluting with 0 to 10% ether in hexane to give the title compound. $^1$H NMR (500 MHz, CD$_3$OD): δ 8.59 (s, 1H), 7.84 (d, 1H), 7.48 (d, 1H), 6.74 (t, 1H).

Step C 2-Methyl-2-(5-difluoromethyl-2-pyridyloxy)propionic Acid

The title compound (1.6 g) was prepared from 4-chloro-3-difluoromethylpyridine (3.0 g) following the procedure described for Reference Example 15 with the following modifications. The ester intermediate was purified by flash column chromatography on silica gel eluting with 0 to 10% ether in hexane. The hydrolysis of the ester to the title compound was effected with lithium hydroxide in methanol/tetrahydrofuran/water. $^1$H NMR (500 MHz, CD$_3$OD): δ 8.22 (d, 1H), 7.82 (dd, 1H), 6.88 (d, 1H), 6.77 (t, 1H), 1.64 (s, 6H).

REFERENCE EXAMPLE 21

N-[2-(3-bromo-5-cyanophenyl)-3-(4-chlorophenyl)-1-methylpropyl]amine hydrochloride
(Diastereomer α)

The title compound was prepared following the procedures described for Reference Example 5 substituting 3,5-dibromofluorobenzene with 3,5-dibromocyanobenzene and 1,1'-bis(diphenylphosphino)ferrocene with 2-(diphenylphosphino)-2'-(N,N-dimethylamino)biphenyl at Step A. $^1$H NMR (500 MHz, CD$_3$OD): δ 7.84 (s, 1H), 7.70 (s, 1H), 7.58 (s, 1H), 7.20 (d, 2H), 7.04 (d, 2H), 3.75 (m, 1H), 3.30 (m, 1H), 3.21 (m, 1H), 2.95 (m, 1H), 1.19 (d, 3H).

REFERENCE EXAMPLE 22

N-[3-(4-fluorophenyl)-2-(3-cyano-5-fluorophenyl)-1-methylpropyl]amine hydrochloride
(Diastereomer α)

The title compound was prepared following the procedure described for Reference Example 6 substituting 4-chlorobenzyl chloride with 4-fluorobenzyl chloride at Step B. LC-MS: m/e 340 (M+H)$^+$ (3.0 min).

EXAMPLE 1 (METHOD A)

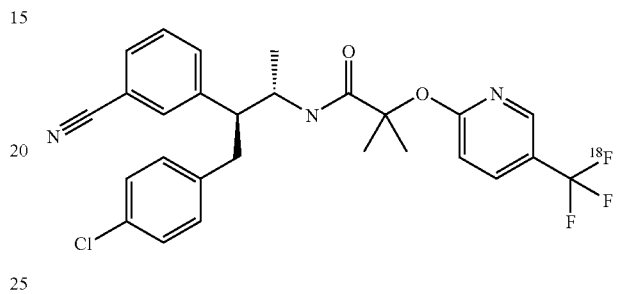

N-(1S, 2S)-[2-(3-Cyanophenyl)-3-(4-chlorophenyl)-1-methylpropyl]-2-(5-[$^{18}$F]-trifluoromethyl-2-pyridyloxy)-2-methylpropanamide Step A N-(1S, 2S)-[2-(3-Cyanophenyl)-3-(4-chlorophenyl)-1-methylpropyl]-2-(5-trifluoromethyl-2-pyridyloxy)-2-methylpropanamide To a solution of 2-methyl-2-(5-trifluoromethyl-2-pyridyloxy)propionic acid (Reference Example 15, 159 g, 0.64 mol) in toluene (1.5 L) under nitrogen was added thionyl chloride (93 mL, 1.3 mmol). After stirring for 1 h, the reaction mixture was concentrated, and the residue was suspended in acetonitrile (1.2 L). The mixture was cooled with an ice-water bath, and N-(1S, 2S)-[3-(4-chlorophenyl)-2-(3-cyanophenyl)-1-methylpropyl]amine (Reference Example 4, 151 g, 0.53 mol) in acetonitrile (127 mL) and triethylamine (89 mL, 0.64 mol) was added while maintaining the reaction temperature at 5-10° C. After stirring for 30 min, the reaction mixture was partitioned between water (1.6 L) and isopropyl acetate (2.7 L). The organic layer was separated, washed with 2N NaOH (2×1.2 L) and water (1.2 L) and filtered through a silica gel plug (4.9 kg), which was washed with ethyl acetate/hexanes (30:70, approx. 82 L). The compound containing fractions were combined and concentrated to give the crude title compound. Crystallization from isopropyl acetate/cyclohexane and recrystallization from isopropyl acetate/heptane gave the pure compound. $^1$H NMR (500 MHz, CD$_3$OD): δ 8.30 (d, 1H), 8.01 (br d, 1 H), 7.97 (dd, 1H), 7.52 (d, 1H), 7.43-7.33 (m, 3 H), 7.07 (d, 1H), 7.06 (d, 2H), 6.72 (d, 2H), 4.28 (m, 1H), 3.07 (dd, 1H), 2.88 (td, 1H), 2.65 (dd, 1H), 1.79 (s, 3H), 1.76 (s, 3H), 0.83 (d, 3H). LC -MS: m/e 516 (M +H)$^+$ (3.9 min).

Step B N-(1S, 2S)-[2-(3-Cyanophenyl)-3-(4-chlorophenyl)-1-methylpropyl]-2-(5-[$^{18}$F]-trifluoromethyl-2-pyridyloxy)-2-methylpropanamide The residue obtained after drying of the [$^{18}$F]F$^−$ (~225 mCi, Reference Example 1) was treated with a solution of N-(1S, 2S)-[3-(4-chlorophenyl)-2-(3-cyanophenyl)-1-methylpropyl]-2-(5-trifluoromethyl-2-pyridyloxy)-2-methylpropanamide (1.6 mg) in benzene (0.2 mL) and heated at 95° C.

for 45 minutes. The reaction mixture was diluted with MeCN (0.3 mL) and H₂O (0.5 mL) and injected onto the HPLC (Waters C18 XTerra, 7.8×150 mm, 3 mL/min, 10 minute linear gradient, 50% A:B to 90% A:B, hold at 90% A for 10 minutes, A=MeCN, B=95:5:0.1 H₂O:MeCN:TFA, retention time ~8 minutes). Fractions from the HPLC were collected using a fraction collector (1 min/tube) and fraction corresponding to [$^{18}$F]-N-(1S, 2S)-[2-(3-cyanophenyl)-3-(4-chlorophenyl)-1-methylpropyl]-2-(5-trifluoromethyl-2-pyridyloxy)-2-methylpropanamide contained 28 mCi of N-(1S, 2S)-[3-(4-chlorophenyl)-2-(3-cyanophenyl)-1-methylpropyl]-2-(5-[$^{18}$F]-trifluoromethyl-2-pyridyloxy)-2-methylpropanamide.

EXAMPLE 2 (METHOD B)

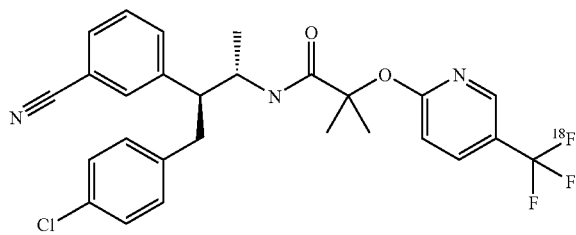

N-(1S, 2S)-[2-(3-Cyanophenyl)-3-(4-chlorophenyl)-1-methylpropyl]-2-(5-[$^{18}$F]-trifluoromethyl-2-pyridyloxy)-2-methylpropanamide Step A tert-Butyldimethylsilyl-2-methyl-2-(5-difluoromethyl-2-pyridyloxy)propionate A solution of 2-methyl-2-(5-difluoromethyl-2-pyridyloxy)propionic acid (Reference Example 20, 1.7 g, 6.6 mmol) and tert-butyldimethylsilyl chloride (2.0 g, 13 mmol) and imidazole (1.0 g, 15 mmol) in 50 mL of dimethylformamide was stirred at room temperature overnight. The reaction mixture was partitioned between water (200 mL) and ether (200 mL). The organic layer was separated, washed with water and brine, dried over magnesium sulfate, filtered and concentrated to dryness, and the residue was dried under vacuum to give the title compound. $^1$H NMR (500 MHz, CDCl₃): δ 8.20 (d, 1H), 7.75 (d, 1H), 6.85 (d, 1H), 6.65 (t, 1H), 1.72 (s, 6H), 0.77 (s, 9H), 0.24 (s, 6H).

Step B 2-(5-Bromodifluoromethyl-2-pyridyloxy)-2-methylpropionic acid

A mixture of tert-butyldimethylsilyl-2-methyl-2-(5-difluoromethyl-2-pyridyloxy)propionate (1.0 g, 2.9 mmol) and N-bromosuccinimide (1.2 g, 6.7 mmol) in 15 mL of carbon tetrachloride was degassed and irradiated with a sun lamp for 1 day. After another batch of N-bromosuccinimide (1.0 g, 5.1 mmol) was added, irradiation continued for one more day. The resulting mixture was concentrated, and the residue was taken up by tetrahydrofuran (15 mL) and was added 2 N hydrochloric acid (15 mL). After stirring at room temperature for 30 min, the product was extracted with ether (50 mL×2). The combined extracts were washed with water and brine, dried over magnesium sulfate, filtered and concentrated to dryness to give the crude 2-(5-bromodifluoromethyl-2-pyridyloxy)-2-methylpropionic acid along with 2-(5-difluoromethyl-2-pyridyloxy)-2-methylpropionic acid, which was used without further purification. LC-MS: m/e 310 (M+H)⁺ (2.3 min).

Step C N-(1S,2S)-[2-(3-Cyanophenyl)-3-(4-chlorophenyl)-1-methylpropyl]-2-(5-bromodifluoromethyl-2-pyridyloxy)-2-methylpropanamide and N-(1S,2S)-[2-(3-Cyanophenyl)-3-(4-chlorophenyl)-1-methylpropyl]-2-(5-difluoromethyl-2-pyridyloxy)-2-methylpropanamide The crude 2-(5-bromodifluoromethyl-2-pyridyloxy)-2-methylpropionic acid of Step B was converted to the corresponding acyl chloride and reacted with N-(1S, 2S)-[2-(3-cyanophenyl)-3-(4-chlorophenyl)-1-methylpropyl]amine hydrochloride (Reference Example 4) following the procedure described in Example 1 using N-methylmorpholine instead of triethylamine as the base. The product was purified by flash column chromatography on silica gel eluting with 5-50% ethyl acetate in hexane to give the two title compounds, which were further purified by HPLC on a Chiralpak™ AD-H column eluting with 10% ethanol in hexane.

N-(1S,2S)-[2-(3-Cyanophenyl)-3-(4-chlorophenyl)-1-methylpropyl]-2-(5-bromodifluoromethyl-2-pyridyloxy)-2-methylpropanamide (fasting eluting isomer on Chiralpak™ AD column): $^1$H NMR (500 MHz, CD₃OD) δ 8.27 (d, 1H), 7.99 (br d, 1H), 7.95 (dd, 1H), 7.50 (br d, 1H), 7.40-7.31 (m, 3H), 7.07-7.02 (m, 3H), 6.71 (d, 2H), 4.27 (m, 1H), 3.04 (dd, 1H), 2.86 (m, 1H), 2.63 (dd, 1H), 1.77 (s, 3H), 1.74 (s, 3H), 0.81 (d, 3H). LC-MS: m/e 576 (M+H)⁺ (4.1 min).

N-(1S,2S)-[2-(3-Cyanophenyl)-3-(4-chlorophenyl)-1-methylpropyl]-2-(5-difluoromethyl-2-pyridyloxy)-2-methylpropanamide (slower eluting isomer on Chiralpak™ AD column): $^1$H NMR (500 MHz, CDCl₃): δ 8.22 (d, 1H), 7.83 (dd, 1H), 7.50 (br d, 1H), 7.34 (t, 1H), 7.28-7.23 (m, 2H), 7.11 (d, 2H), 6.90 (d, 1H), 6.74 (d, 2H), 6.61 (t, 1H), 4.37 (m, 1H), 3.17 (dd, 1H), 2.84 (ABX, 2H), 1.78 (s, 3H), 1.73 (s, 3H), 0.90 (d, 3H). LC-MS: m/e 498 (M+H)⁺ (2.8 min).

Step C N-(1S, 2S)-[2-(3-Cyanophenyl)-3-(4-chlorophenyl)-1-methylpropyl]-2-(5-[$^{18}$F]-trifluoromethyl-2-pyridyloxy)-2-methylpropanamide Microwave heating (~45 W) was used to dry the [$^{18}$F]F⁻ (~300 mCi) in the presence of Kryptofix222. A solution of N-(1S,2S)-[2-(3-cyanophenyl)-3-(4-chlorophenyl)-1-methylpropyl]-2-(5-bromodifluoromethyl-2-pyridyloxy)-2-methylpropanamide (0.9 mg) in DMSO (0.2 mL) was transferred to the vial in the microwave cavity and pulsed with 3×10 sec cycles with 20 seconds between pulses. The reaction mixture was diluted with H₂O (0.6 mL) and injected onto the HPLC (Waters C18 XTerra, 7.8×150 mm, 3 mL/min, 10 minute linear gradient, 50% A:B to 90% A:B, hold at 90% A for 10 minutes, A=MeCN, B=95:5:0.1 H₂O:MeCN:TFA, retention time ~8 minutes). Fractions from the HPLC were collected using a fraction collector (1 min/tube) and fraction corresponding to [$^{18}$F]-N-(1S, 2S)-[3-(4-chlorophenyl)-2-(3-cyanophenyl)-1-methylpropyl]-2-(5-trifluoromethyl-2-pyridyloxy)-2-methylpropanamide contained 9.3 mCi of [$^{18}$F]-N-(1S, 2S)-[3-(4-chlorophenyl)-2-(3-cyanophenyl)-1-methylpropyl]-2-(5-trifluoromethyl-2-pyridyloxy)-2-methylpropanamide.

EXAMPLE 3

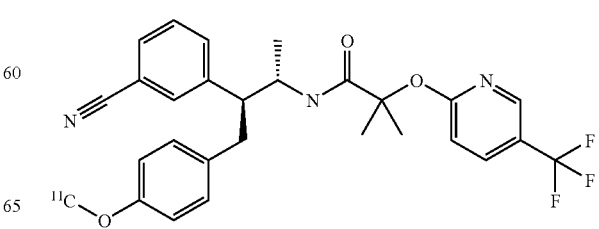

N-[2-(3-Cyano-phenyl)-3-(4-[$^{11}$C]-methoxyphenyl)-1-methylpropyl]-2-(5-trifluoromethyl-2-pyridyloxy)-2-methylpropanamide Step A N-[2-(3-Cyano-phenyl)-3-(4-hydroxyphenyl)-1-methylpropyl]-2-(5-trifluoromethyl-2-pyridyloxy)-2-methylpropanamide N-[2-(3-Cyano-phenyl)-3-(4-hydroxyphenyl)-1-methylpropyl]-2-(5-trifluoromethyl-2-pyridyloxy)-2-methylpropanamide_was prepared from N-[3-(4-chlorophenyl)-2-(3-cyanophenyl)-1-methylpropyl]-2-(5-trifluoromethyl-2-pyridyloxy)-2-methylpropanamide (Example 1) following the procedure described in Reference Example 8, Step B using tris(dibenzylideneacetone)dipalladium and 2-[di(tert-butyl)phosphino]biphenyl as the catalyst. $^1$H NMR (500 MHz, CD$_3$OD): δ 8.30 (d, 1H), 7.95 (dd, 1H), 7.50 (br d, 1H), 7.40-7.32 (m, 3H), 7.08 (d, 1H), 6.55 (d, 2H), 6.49 (d, 2H), 4.25 (m, 1H), 3.00 (dd, 1H), 2.85 (td, 1H), 2.58 (d, 1H), 1.78 (s, 3H), 1.74 (s, 1H), 0.82 (d, 3H). LC-MS: m/e 498 (M+H)$^+$ (3.5 min).

Step B N-[2-(3-Cyano-phenyl)-3-(4-[$^{11}$C]-methoxyphenyl)-1-methylpropyl]-2-(5-trifluoromethyl-2-pyridyloxy)-2-methylpropanamide

[$^{11}$C]MeI was trapped in a RT mixture of N-[2-(3-cyano-phenyl)-3-(4-hydroxyphenyl)-1-methylpropyl]-2-(5-trifluoromethyl-2-pyridyloxy)-2-methylpropanamide (0.3 mg) in DMF (0.2 mL) containing Cs$_2$CO$_3$. The reaction mixture was transferred to a 2 mL v-vial at 100° C., heated for 4 minutes, diluted with H$_2$O (0.8 mL) and injected onto the HPLC (Waters C18 XTerra, 7.8×150 mm, 3 mL/min, 10 minute linear gradient, 30% A:B to 95% A:B, hold at 95% A for 5 minutes, A=MeCN, B=95:5:0.1 H$_2$O:MeCN:TFA, retention time ~9.5 minutes). The desired peak was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 5.8 mCi of N-[2-(3-cyano-phenyl)-3-(4-[$^{11}$C]-methoxyphenyl)-1-methylpropyl]-2-(5-trifluoromethyl-2-pyridyloxy)-2-methylpropanamide.

EXAMPLE 4

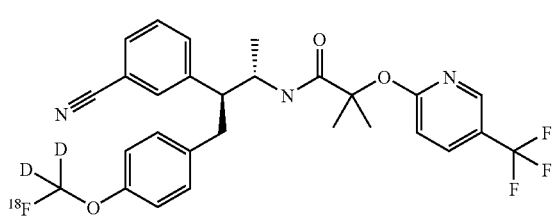

N-[2-(3-Cyano-phenyl)-3-(4[$^{18}$F]-dideuterio-fluoromethoxyphenyl)-1-methylpropyl]-2-(5-trifluoromethyl-2-pyridyloxy)-2-methylpropanamide

[$^{18}$F]FCD$_2$Br was distilled into a 0° C. mixture of N-[2-(3-cyano-phenyl)-3-(4-hydroxyphenyl)-1-methylpropyl]-2-(5-trifluoromethyl-2-pyridyloxy)-2-methylpropanamide from Example 3, Step A (0.3 mg) in DMF (0.2 mL) containing Cs$_2$CO$_3$. The reaction mixture was transferred to a 2 mL v-vial at 100° C., heated for 5 minutes, diluted with H$_2$O (0.8 mL) and injected onto the HPLC (Waters C18 XTerra, 7.8×150 mm, 3 mL/min, 10 minute linear gradient, 30% A:B to 95% A:B, hold at 95% A for 5 minutes, A=MeCN, B=95:5:0.1 H$_2$O:MeCN:TFA, retention time ~9.5 minutes). The desired peak was collected in a heated round bottom flask on a rotary evaporator. The solution was concentrated and vacuum transferred to a septum capped 5 mL v-vial. The round bottom flask is rinsed with ethanol (0.1 mL) and saline (1-2 mL) and vacuum transferred to the same v-vial to give 11.8 mCi of N-[2-(3-cyano-phenyl)-3-(4-[$^{18}$F]-dideuteriofluoromethoxyphenyl)-1-methylpropyl]-2-(5-trifluoromethyl-2-pyridyloxy)-2-methylpropanamide.

EXAMPLE 5

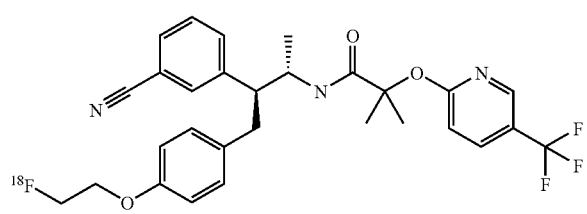

N-[2-(3-Cyano-phenyl)-3-(4-(2-[$^{18}$F]-fluoroethoxy)phenyl)-1-methylpropyl]-2-(5-trifluoromethyl-2-pyridyloxy)-2-methylpropanamide

[$^{18}$F]FCH$_2$CH$_2$Br was distilled into a room temperature mixture of N-[2-(3-cyano-phenyl)-3-(4-hydroxyphenyl)-1-methylpropyl]-2-(5-trifluoromethyl-2-pyridyloxy)-2-methylpropanamide from Example 3, Step A (0.3 mg) in DMF (0.2 mL) containing Cs$_2$CO$_3$. The reaction mixture was transferred to a 2 mL v-vial at 100° C., heated for 5 minutes, diluted with H$_2$O (0.8 mL) and injected onto the HPLC (Waters C18 XTerra, 7.8×150 mm, 3 mL/min, 10 minute linear gradient, 30% A:B to 95% A:B, hold at 95% A for 5 minutes, A=MeCN, B=95:5:0.1 H$_2$O:MeCN:TFA, retention time ~9.5 minutes). The desired peak was collected in a heated round bottom flask on a rotary evaporator. The solution was concentrated and vacuum transferred to a septum capped 5 mL v-vial. The round bottom flask is rinsed with ethanol (0.1 mL) and saline (1-2 mL) and vacuum transferred to the same v-vial to give 6.6 mCi.

EXAMPLE 6

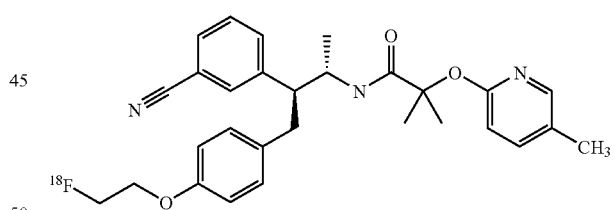

N-[2-(3-Cyano-phenyl)-3-(4-([$^{18}$F]-2-fluoroethoxy)phenyl)-1-methylpropyl]-2-(5-methyl-2-pyridyloxy)-2-methylpropanamide Step A N-[2-(3-Cyano-phenyl)-3-(4-hydroxyphenyl)-1-methylpropyl]-2-(5-methyl-2-pyridyloxy)-2-methylpropanamide To a solution of N-(1S, 2S)-[2-(3-cyanophenyl)-3-(4-hydroxyphenyl)-1-methylpropyl]amine hydrochloride (Reference Example 8, 0.17 g, 0.49 mmol), 2-methyl-2-(5-methyl-2-pyridyloxy)propionic acid (Reference Example 12, 96 mg, 0.49 mmol) and 1-ethyl-3-(3-dimethylaminopropyl)-carbodiimide hydrochloride (0.11 g, 0.59 mmol) in acetonitrile (2 mL) at 0° C. was added pyridine (91 uL, 1.1 mmol). The reaction was allowed to warm up to room temperature overnight, and was quenched with saturated with sodium bicarbonate (2 mL). The resulting mixture was partitioned between tert-butyl methyl ether (20 mL) and water (20 mL). The organic layer was separated, washed with 1 M hydrochloric acid, water and brine and concentrated to dryness. The residue was purified by flash column chromatography on silica gel eluting with 10 to 70% ethyl acetate in hexane to afford N-[2-(3-Cyano-phenyl)-3-(4-hydroxyphenyl)-1-methylpropyl]-2-(5-methyl-2-pyridyloxy)-2-methylpropanamide. $^1$H NMR (500 MHz, CD$_3$OD): δ 7.85 (br d, 1H), 7.81 (d, 1H), 7.53-7.80 (m, 2H), 7.38 (t, 1H), 7.34 (br d, 1H), 7.32 (br s, 1H), 6.80 (d, 1H), 6.51 (ABq, 4H), 4.26 (m, 1H), 3.01 (dd, 1H), 2.81 (td, 1H), 2.54 (dd, 1H), 2.12 (s, 3H), 1.73 (s, 3H), 1.67 (s, 3H), 0.83 (d, 3H). LC-MS: m/e 444 (M+H)$^+$ (3.3 min).

The title compound was recrystallized from 3 mL methyl tert-butyl ether per gram of title compound to give a crystal form that was characterized as follows:

Differential scanning calorimetry (DSC) data were collected at a heating rate of 10° C./min, under nitrogen atmosphere in a crimped pan. The DSC curve displays a melting endotherm with an extrapolated onset temperature of 162.9° C., a peak temperature of 164.2° C., and an enthalpy change of 96 J/g.

The title compound displays the following X-ray powder diffraction pattern (XRPD) (as shown in FIG. 1). The characteristic diffraction peaks corresponding to d-spacings of 12.6, 7.8, 6.5, 4.8, 4.2, 4.1 angstroms. The X-ray powder diffraction pattern was generated on a Philips Analytical X'Pert PRO X-ray Diffraction System with PW3040/60 console. A PW3373/00 ceramic Cu LEF X-ray tube K-Alpha radiation was used as the source.

Step B N-[2-(3-Cyano-phenyl)-3-(4-([$^{18}$F]-2-fluoroethoxy)phenyl)-1-methylpropyl]-2-(5-methyl-2-pyridyloxy)-2-methylpropanamide

[$^{18}$F]FCH$_2$CH$_2$Br was distilled into a room temperature mixture of N-[2-(3-cyano-phenyl)-3-(4-hydroxyphenyl)-1-methylpropyl]-2-(5-methyl-2-pyridyloxy)-2-methylpropanamide (0.3mg) in DMF (0.2 mL) containing Cs$_2$CO$_3$. The reaction mixture was transferred to a 2 mL v-vial at 100° C., heated for 5 minutes, diluted with H$_2$O (0.8 mL) and injected onto the HPLC (Waters C18 XTerra, 7.8×150 mm, 3 mL/min, 10 minute linear gradient, 30% A:B to 95% A:B, hold at 95% A for 5 minutes, A=MeCN, B=95:5:0.1 H$_2$O:MeCN:TFA, retention time ~9 minutes). The desired peak was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 25 mCi of N-[2-(3-cyano-phenyl)-3-(4-([$^{18}$F]-2-fluoroethoxy)phenyl)-1-methylpropyl]-2-(5-methyl-2-pyridyloxy)-2-methylpropanamide.

EXAMPLE 7

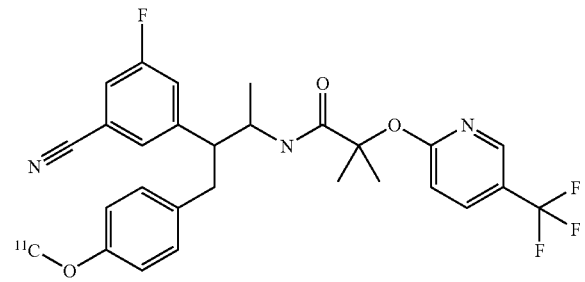

N-[2-(3-Cyano-5-fluorophenyl)-(4-[$^{11}$C]-methoxyphenyl)-1-methylpropyl]-2-(5-trifluoromethyl-2-pyridyloxy)-2-methylpropanamide Step A N-[2-(3-Cyano-5-fluorophenyl)-4-chlorophenyl)-1-methylpropyl]-2-(5-trifluoromethyl-2-pyridyloxy-2-methylpropanamide To a solution of N-[2-(3-cyano-5-fluorophenyl)-3-(4-chlorophenyl)-1-methylpropyl]amine hydrochloride salt (Reference Example 6, 1.0 g, 3.0 mol) and 2-(5-trifluoromethyl-2-pyridyloxy)-2-methylpropionic acid (Reference Example 15, 0.90 g, 3.6 mmol) in 10 mL of CH$_2$Cl$_2$ was added N-methylmorpholine (0.99 mL, 9.0 mmol) and tris(pyrrolindinyl) phosphonium hexafluorophosphate (2.4 g, 4.5 mmol). After stirring at room temperature overnight, the reaction mixture was loaded onto a silica gel column eluted with 30% EtOAc in hexane to afford N-[2-(3-cyano-5-fluorophenyl)-(4-chlorophenyl)-1-methylpropyl]-2-(5-trifluoromethyl-2-pyridyloxy)-2-methylpropanamide in racemic form. $^1$H NMR (500 MHz, CD$_3$OD): δ 8.26 (br s, 1H), 7.96 (d, 1H), 7.93 (dd, 1H), 7.30 (br d, 1H), 7.22 (s, 1H), 7.15 (br d, 1H), 7.06 (d, 2H), 7.05 (m, 1H), 6.74 (d, 2H), 4.24 (m, 1H), 3.05 (dd, 1H), 2.91 (m, 1H), 2.63 (dd, 1H), 1.74 (s, 3H), 1.72 (s, 3H), 0.83 (d, 3H). LC-MS: m/e 534 (M+H)$^+$ (4.2 min).

The racemic mixture obtained above was separated into Enantiomer A and Enantiomer B by preparative HPLC eluting on a Chiralpak AD column (2 cm×25 cm), with 8% ethanol in hexane (flow rate 9 mL/min, 500 μL per injection).

Faster eluting enantiomer (Enantiomer A): Analytical HPLC: retention time=8.2 min (Chiralpak AD column, flow rate=0.75 mL/min, 8% ethanol/hexane). LC-MS: mnle 534 (M+H)$^+$ (4.2 min).

Slower eluting enantiomer (Enantiomer B): Analytical HPLC: retention time=11.0 min (Chiralpak AD column, flow rate=0.75 mL/min, 8% ethanol/hexane). LC-MS: m/e 534 (M+H)$^+$ (4.2 min).

Step B N-[2-(3-Cyano-5-fluorophenyl)-(4-hydroxyphenyl)-1-methylpropyl]-2-(5-trifluoromethyl-2-pyridyloxy)-2-methylpropanamide N-[2-(3-Cyano-5-fluorophenyl)-4-hydroxyphenyl)-1-methylpropyl]-2-(5-trifluoromethyl-2-pyridyloxy)-2-methylpropanamide was prepared from N-[2-(3-cyano-5-fluorophenyl)-(4-chlorophenyl)-1-methylpropyl]-2-(5-trifluoromethyl-2-pyridyloxy)-2-methylpropanamide (Step A, slower eluting isomer) following the procedure described in Reference Example 8, Step B using tris(dibenzylideneacetone) dipalladium and tri(tert-butyl)phosphine as the catalyst. $^1$H NMR (500 MHz, CD$_3$OD): δ 8.27 (d, 1H), 7.96 (br s, 1H), 7.94 (d, 1H), 7.93 (d, 1H), 7.30 (m, 1H), 7.18 (br s, 1H), 7.14 (m, 1H), 7.04 (d, 1H), 6.65 (ABq, 4H), 4.24 (m, 1H), 3.03 (dd, 1H), 2.88 (m, 1H), 2.57 (dd, 1H), 1.75 (s, 3H), 1.73 (s, 3H), 0.82 (d, 3H). LC-MS: m/e 530 (M+H)$^+$ (3.8 min).

Step C N-[2-(3-Cyano-5-fluorophenyl)-(4-[$^{11}$C]-methoxyphenyl)-1-methylpropyl]-2-(5-trifluoromethyl-2-pyridyloxy)-2-methylpropanamide

[11C]MeI was trapped in a 0° C. mixture of N-[2-(3-Cyano-5-fluorophenyl)-(4-hydroxyphenyl)-1-methylpropyl]-2-(5-trifluoromethyl-2-pyridyloxy)-2-methylpropanamide (0.3 mg) in DMF (0.2 mL) containing Cs2CO3. The reaction mixture was transferred to a.2 mL v-vial at 100° C., heated for 4 minutes, diluted with H2O (0.8 mL) and injected onto the HPLC (Waters C18 XTerra™, 7.8×150 mm, 3 mL/min, 10 minute linear gradient, 30% A:B to 95% A:B, hold at 95% A for 5 minutes, A=MeCN, B=95:5:0.1 H2O:MeCN:TFA, retention time ~10 minutes). The desired peak was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 11.7 mCi of N-[2-(3-cyano-5-fluorophenyl)-(4-[11C]-methoxyphenyl)-1-methylpropyl]-2-(5-trifluoromethyl-2-pyridyloxy)-2-methylpropanamide.

EXAMPLE 8

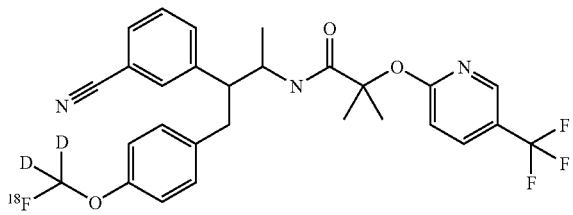

N-[2-(3-Cyano-5-fluorophenyl)-(4-[$^{18}$F]-dideuterio-fluoromethoxyphenyl)-1-methylpropyl]-2-(5-trifluoromethyl-2-pyridyloxy)-2-methylpropanamide

[$^{18}$F]FCD$_2$Br was distilled into a 0° C. mixture of N-[2-(3-cyano-5-fluorophenyl)-(4-hydroxyphenyl)-1-methylpropyl]-2-(5-trifluoromethyl-2-pyridyloxy)-2-methylpropanamide (0.3 mg) in DMF (0.2 mL) containing Cs$_2$CO$_3$. The reaction mixture was transferred to a 2 mL v-vial at 100° C., heated for 4 minutes, diluted with H$_2$O (0.8 mL) and injected onto the HPLC (Waters C18 XTerra™, 7.8×150 mm, 3 mL/min, 10 minute linear gradient, 30% A:B to 95% A:B, hold at 95% A for 5 minutes, A=MeCN, B=95:5:0.1 H$_2$O:MeCN:TFA, retention time ~10 minutes). The desired peak was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 6.5 mCi of N-[2-(3-cyano-5-fluorophenyl)-(4-[$^{18}$F]-dideuterio-fluoromethoxyphenyl)-1-methylpropyl]-2-(5-trifluoromethyl-2-pyridyloxy)-2-methylpropanamide.

EXAMPLE 9

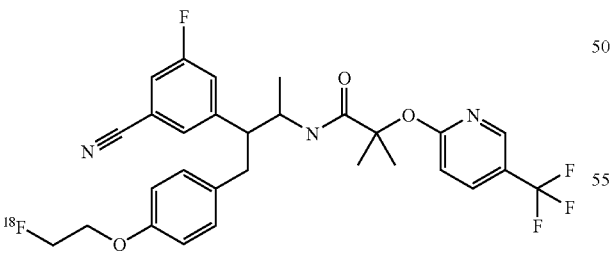

N-[2-(3-Cyano-5-fluorophenyl)-(4-(2-[$^{18}$F]-fluoroethoxy)phenyl)-1-methylpropyl]-2-(5-trifluoromethyl-2-pyridyloxy)-2-methylpropanamide

[$^{18}$F]FCH$_2$CH$_2$Br was distilled into a room temperature mixture of N-[2-(3-cyano-5-fluorophenyl)-(4-hydroxyphenyl)-1-methylpropyl]-2-(5-trifluoromethyl-2-pyridyloxy)-2-methylpropanamide (0.3 mg) in DMF (0.2 mL) containing Cs$_2$CO$_3$. The reaction mixture was transferred to a 2 mL v-vial at 100° C., heated for 5 minutes, diluted with H$_2$O (0.8 mL) and injected onto the HPLC (Waters C18 XTerra™, 7.8×150 mm, 3 mL/min, 10 minute linear gradient, 30% A:B to 95% A:B, hold at 95% A for 5 minutes, A=MeCN, B=95:5:0.1 H$_2$O:MeCN:TFA, retention time ~10 minutes). The desired peak was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 6.2 mCi of N-[2-(3-cyano-5-fluorophenyl)-(4-(2-[$^{18}$F]-fluoroethoxy)phenyl)-1-methylpropyl]-2-(5-trifluoromethyl-2-pyridyloxy)-2-methylpropanamide.

EXAMPLE 10

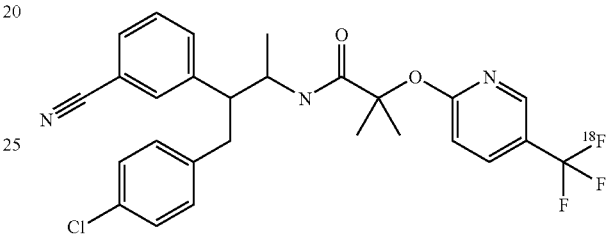

N-(1S, 2S)-[3-(4-chlorophenyl)-2-(3-cyano-5-fluorophenyl)-1-methylpropyl]-2-5-[$^{18}$F]-(trifluoromethyl-2-pyridyloxy)-2-methylpropanamide The residue obtained after drying of the [$^{18}$F]F$^-$ was treated with a solution of N-[2-(3-cyano-5-fluorophenyl)-4-chlorophenyl)-1-methylpropyl]-2-(5-trifluoromethyl-2-pyridyloxy)-2-methylpropanamide from Example 7, Step A (0.6 mg) in DMSO (0.2 mL) and the solution was heated with 3×15 second microwave pulses with a 30 second pause between microwave cycles. The reaction was diluted with H$_2$O (0.6 mL) and injected onto the HPLC (Waters C18 Bondapak™, 7.8×300 mm, 3 mL/min, 7 minute linear gradient, 50% A:B to 95% A:B, hold at 95% A for 8 minutes, A=MeCN, B=95:5:0.1 H$_2$O:MeCN:TFA, retention time ~10.5 minutes). The desired peak was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 7.3 mCi.

EXAMPLE 11

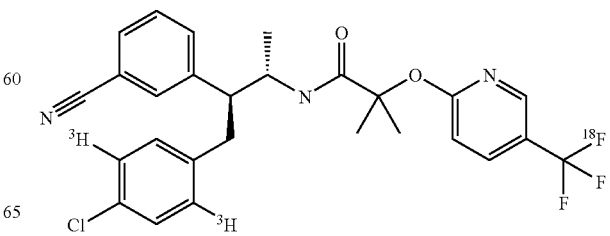

N-(1S, 2S)-[3-(4-Chloro-2,5-ditritiophenyl)-2-(3-cyanophenyl)-1-methylpropyl]-2-(5-trifluoromethyl-2-pyridyloxy)-2-methylpropanamide Step A N-(1S, 2S)-[3-(4-Chloro-2,5-ditritiophenyl)-2-(3-cyanophenyl)-1-methylpropyl]-2-(5-trifluoromethyl-2-pyridyloxy)-2-methylpropanamide The procedure of Barluenga (*J Org Chem* 1990, 55, 3104) was used. Thus, to a solution of N-[3-(4-chlorophenyl)-2-(5-chloro-3-pyridyl)-1-methylpropyl]-2-(5-trifluoromethyl-2-pyridyloxy)-2-methylpropanamide (Example 1, 40 mg, 0.078 mmol) and bis(pyridine)iodonium tetrafluoroborate (100 mg, 0.27 mmol) in 0.5 mL anhydrous $CH_2Cl_2$ was added triflic acid (50 μL, 0.56 mmol). After stirring at room temperature for 30 min, the reaction mixture was poured into a mixture of ice (20 g) and sodium bisulfite (1 g) and the product was extracted with EtOAc. The organic extracts were dried over anhydrous sodium sulfate, filtered and concentrated to dryness to give the crude product, which was purified by preparative HPLC eluting on a reverse-phase HPLC column with 75 to 100% acetonitrile in water to give the title compound. $^1$H NMR (500 MHz, $CD_3OD$): δ 8.29 (d, 1H), 7.99 (d, 1H), 7.94 (dd, 1H), 7.76 (s, 1H), 7.55 (d, 1H), 7.45-7.39 (m, 2H), 7.34 (d, 1H), 7.18 (s, 1H), 7.05 (d, 1H), 4.38 (m, 1H), 3.10 (dd, 1H), 2.98 (td, 1H), 2.83 (dd, 3H) 1.78 (s, 3H), 1.76 (s, 3H), 0.96 (d, 3H). LC-MS: m/e 768 (M+H)$^+$ (2.9 min).

Step B N-(1S, 2S)-[3-(4-Chloro-2,5-ditritiophenyl)-2-(3-cyanophenyl)-1-methylpropyl]-2-(5-trifluoromethyl-2-pyridyloxy)-2-methylpropanamide A solution of N-(1S, 2S)-[3-(4-chloro-2,5-diiodophenyl)-2-(3-cyanophenyl)-1-methylpropyl]-2-(5-trifluoromethyl-2-pyridyloxy)-2-methylpropanamide in ethyl acetate/ethanol is treated with palladium on charcoal and tritium gas to afford [$^3$H]—N-(1S, 2S)-[3-(4-chloro-2,5-ditritiophenyl)-2-(3-cyanophenyl) -1-methylpropyl]-2-(5-trifluoromethyl-2-pyridyloxy)-2-methylpropanamide.

The following examples were prepared with non-radiolabeled isotopes and were used to characterize the products described in Examples 1-11. The corresponding radiolabeled analogues may be prepared according to the methods described in Examples 1-11.

EXAMPLE 12

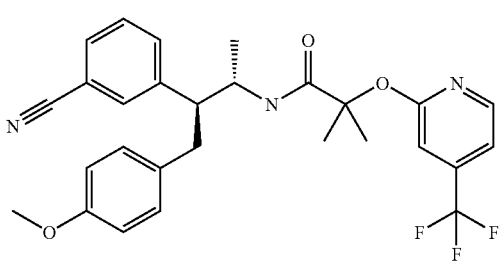

N-(1S,2S)-[2-(3-Cyanophenyl)-3-(4-methoxyphenyl)-1-methylpropyl]-2-(4-trifluoromethyl-2-pyridyloxy)-2-methylpropanamide Step A N-(1S, 2S)-[3-(4-Chlorophenyl)-2-(3-cyanophenyl)-1-methylpropyl]-2-(4-trifluoromethyl-2-pyridyloxy-2-methylpropanamide To a solution of N-(1S, 2S)-[3-(4-chlorophenyl)-2-(3-cyanophenyl)-1-methylpropyl]amine (Reference Example 4, 0.60 g, 2.1 mol) and 2-(4-trifluoromethyl-2-pyridyloxy)-2-methylpropionic acid (Reference Example 13, 0.58 g, 2.4 mmol) in 10 mL of $CH_2Cl_2$ was added N-methylmorpholine (0.46 mL, 4.2 mmol) and tris(pyrrolindinyl)phosphonium hexafluorophosphate (1.6 g, 3.2 mmol). After stirring at room temperature overnight, the reaction mixture was loaded onto a silica gel column eluted with 30% EtOAc in hexane to give the title compound. $^1$H NMR (500 MHz, $CD_3OD$): δ 8.19 (d, 1H), 7.48 (d, 1H), 7.38-7.35 (m, 2H), 7.31 (d, 1H), 7.18 (s, 1H), 7.11 (d, 1H), 7.03 (d, 2H), 6.67 (d, 2H), 4.23 (m, 1H), 3.01 (dd, 1H), 2.83 (m, 1H), 2.61 (dd, 1H), 1.76 (s, 3H), 1.72 (s, 3H), 0.79 (d, 3H).

Step B N-[2-(3-Cyanophenyl)-3-(4-hydroxyphenyl)-1-methylpropyl]-2-(4-trifluoromethyl-2-pyridyloxy)-2-methylpropanamide The title compound was prepared from N-[3-(4-chlorophenyl)-2-(3-cyanophenyl)-1-methylpropyl]-2-(5-trifluoromethyl-2-pyridyloxy)-2-methylpropanamide following the procedure described in Reference Example 8, Step B using tris(dibenzylideneacetone)dipalladium and tri(tert-butyl)phosphine as the catalyst. $^1$H NMR (500 MHz, $CD_3OD$): δ 8.19 (d, 1H), 7.94 (d, 1H), 7.27 (d, 1H), 7.38 (d, 1H), 7.33 (s, 1H), 7.18 (s, 1H), 7.11 (d, 1H), 7.48 (ABq, 4H), 4.23 (m, 1H), 2.94 (dd, 1H), 2.81 (m, 1H), 2.52 (dd, 1H), 1.76 (s, 3H), 1.74 (s, 3H), 0.79 (d, 3H). LC-MS: m/e 498 (M+H)$^+$ (3.6 min).

Step C N-(1S,2S)-[2-(3-Cyanophenyl)-3-(4-methoxyphenyl)-1-methylpropyl]-2-(4-trifluoromethyl-2-pyridyloxy)-2-methylpropanamide N-(1S,2S)-[2-(3-Cyanophenyl)-3-(4-methoxyphenyl)-1-methylpropyl]-2-(4-trifluoromethyl-2-pyridyloxy)-2-methylpropanamide was prepared from N-(1S,2S)-[2-(3-cyanophenyl)-3-(4-hydroxyphenyl)-1-methylpropyl]-2-(4-trifluoromethyl-2-pyridyloxy)-2-methylpropanamide following the procedure described in Example 3. $^1$H NMR (500 MHz, $CD_3OD$): δ 8.19 (d, 1H), 7.48 (br d, 1H), 7.37-7.31 (m, 3H), 7.17 (s, 1H), 7.10 (br d, 1H), 6.60 (s, 4H), 4.24 (m, 1H), 3.66 (s, 3H), 2.99 (dd, 1H), 2.84 (m, 1H), 2.56 (dd, 1H), 1.75 (s, 3H), 1.73 (s, 3H), 0.79 (d, 3H). LC-MS: m/e 512 (M+H)$^+$ (3.9 min).

EXAMPLE 13

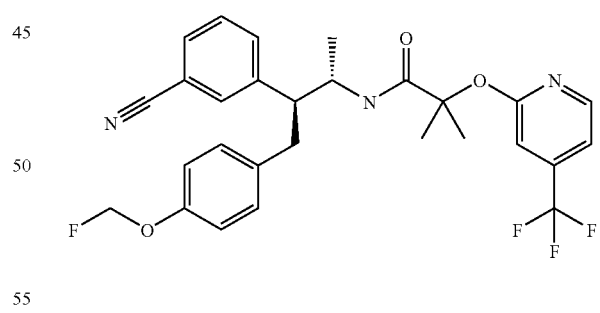

N-(1S,2S)-[2-(3-Cyanophenyl)-3-(4-fluoromethoxyphenyl)-1-methylpropyl]-2-(4-trifluoromethyl-2-pyridyloxy)-2-methylpropanamide N-(1S,2S)-[2-(3-Cyanophenyl)-3-(4-fluoromethoxyphenyl)-1-methylpropyl]-2-(4-trifluoromethyl-2-pyridyloxy)-2-methylpropanamide was prepared from N(1S,2S)-[2-(3-cyanophenyl)-3-(4-hydroxyphenyl)-1-methylpropyl]-2-(4-trifluoromethyl-2-pyridyloxy)-2-methylpropanamide (Example 12, Step B) and fluoromethyliodide following the procedure described in Example 4.

¹H NMR (500 MHz, CD₃OD): δ 8.19 (d, 1H), 7.97 (br d, 1H), 7.47 (d, 1H), 7.40-7.36 (m, 3H), 7.19 (s, 1H), 7.12 (m, 1H), 6.78 (d ,2H), 6.68 (d, 2H), 5.61 (d, 2 H), 4.22 (m, 1H), 3.00 (dd, 1H), 2.83 (m, 1H), 2.60 (dd, 1H), 1.78 (s, 3H), 1.74 (s, 3H), 0.79 (d, 3H). LC-MS: m/e 530 (M+H)⁺ (3.9 min).

EXAMPLE 14

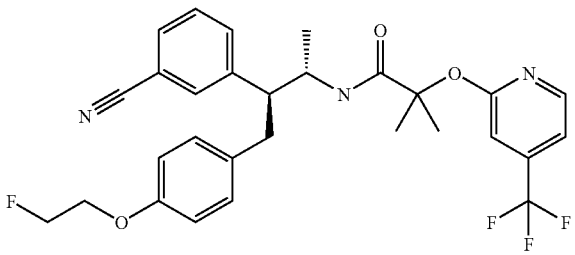

N-(1S,2S)-{2-(3-Cyanophenyl)-3-[4-(2-fluoroethoxy)phenyl]-1-methylpropyl}-2-(4-trifluoromethyl-2-pyridyloxy)-2-methylpropanamide N-(1S,2S)-{2-(3-Cyanophenyl)-3-[4-(2-fluoroethoxy)phenyl]-1-methylpropyl}-2-(4-trifluoromethyl-2-pyridyloxy)-2-methylpropanamide was prepared from N-(1S,2S)-[2-(3-cyanophenyl)-3-(4-hydroxyphenyl)-1-methylpropyl]-2-(4-trifluoromethyl-2-pyridyloxy)-2-methylpropanamide (Example 12, Step B) following the procedure described in Example 5.

¹H NMR (500 MHz, CD₃OD): δ 8.19 (d, 1H), 7.48 (br d, 1H), 7.37-7.31 (m, 3H), 7.16 (s, 1H), 7.11 (d, 1H), 7.65 (ABq, 4H), 4.68 (m, 1H), 4.59 (m, 1H), 4.25 (m, 1H), 4.09 (m, 1H), 4.04 (m, 1H), 2.99 (dd, 1H), 2.84 (m, 1H), 2.56 (dd, 1H), 1.75 (s, 3H), 1.73 (s, 3H), 0.79 (d, 3H). LC-MS: m/e 544 (M+H)⁺ (3.8 min).

EXAMPLE 15

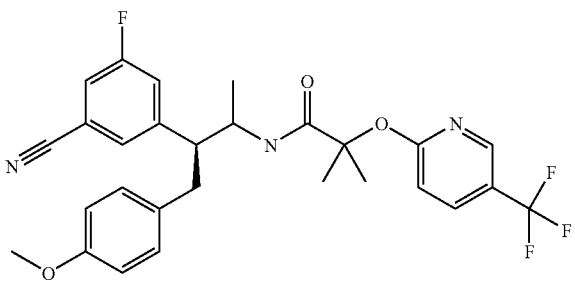

N-[2-(3-Cyano-5-fluorophenyl)-3-(4-methoxyphenyl)-1-methylpropyl]-2-(5-trifluoromethyl-2-pyridyloxy)-2-methylpropanamide To a solution of N-[2-(3-cyano-5-fluorophenyl)-3-(4-hydroxyphenyl)-1-methylpropyl]-2-(5-trifluoromethyl-2-pyridyloxy)-2-methylpropanamide from Example 7, Step B (14 mg, 0.028 mmol) in 1.5 mL of dimethylformamide at 0° C. was added cesium carbonate (14 mg, 0.042 mmol) and methyl iodide (5 uL, 0.084 mmol), and the reaction was allowed to warm up to room temperature over 2 h. The resulting mixture was diluted with ether (20 mL), washed with water and brine and concentrated to dryness. The residue was purified by flash column chromatography eluting with 10 to 40% ethyl acetate in hexane to give the title compound. ¹H NMR (500 MHz, CD₃OD): δ 8.27 (d, 1H), 7.96 (s, 1H), 7.94 (d, 1H), 7.93 (d, 1H), 7.29 (m, 1H), 7.18 (br s, 1H), 7.13 (m, 1H), 7.03 (d, 1H), 6.45 (ABq, 4H), 4.24 (m, 1H), 3.67 (s, 3H), 3.03 (dd, 1H), 2.88 (m, 1H), 2.57 (dd, 1H), 1.75 (s, 3H), 1.73 (s, 3H), 0.82 (d, 3H). LC-MS: m/e 530 (M+H)⁺ (3.9 min).

EXAMPLE 16

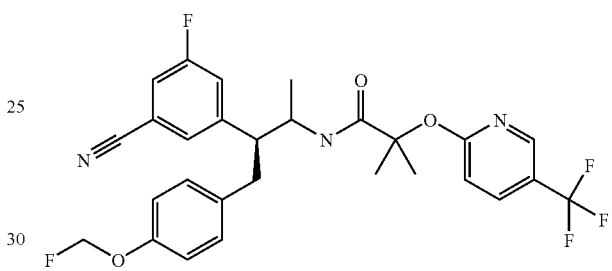

N-[2-(3-Cyano-5-fluorophenyl)-3-(4-fluoromethoxyphenyl)-1-methylpropyl]-2-(5-trifluoromethyl-2-pyridyloxy)-2-methylpropanamide To a solution of N-[2-(3-cyano-5-fluorophenyl)-3-(4hydroxyphenyl)-1-methylpropyl]-2-(5-trifluoromethyl-2-pyridyloxy)-2-methylpropanamide from Example 7, Step B (26 mg, 0.050 mmol) in 2 mL of dimethylformamide was added cesium carbonate (25 mg, 0.076 mmol) and chloromethyl methyl sulfide (6.4 uL, 0.076 mmol), and the reaction was stirred at room temperature for 4 h. The resulting mixture was diluted with ether (20 mL), washed with 0.5 M aqueous sodium bisulfate, water and brine and concentrated to dryness to give the crude methyl thioether, which was used without further purification. Thus, the methyl thioether in 2 mL of 1,2-dichloroethane was added to a solution of xenon difluoride (8.5 mg, 0.050 mmol) in 1.5 mL of 1,2-dichloroethane at 0° C. After stirring at room temperature for 1 h, the reaction was quenched by the addition of triethylamine (0.25 mL), and the resulting mixture was loaded onto a silica gel column eluting with 10 to 40% ethyl acetate in hexane to give N-[2-(3-cyano-5-fluorophenyl)-3-(4-fluoromethoxyphenyl)-1-methylpropyl]-2-(5-trifluoromethyl-2-pyridyloxy)-2-methylpropanamide. ¹H NMR (500 MHz, CD₃OD): δ 8.27 (d, 1H), 7.98 (s, 1H), 7.95 (dd, 1H), 7.31 (m, 1H), 7.21 (s, 1H0, 7.15 (m, 1H), 7.04 (d, 1H), 6.79 (d, 2H), 6.73 (d, 2H), 5.61 (d, 2H), 4.24 (m, 1H), 3.04 (m, 1H), 2.89 (m, 1H), 2.61 (dd, 1H), 1.75 (s, 3H), 1.73 (s, 3H), 0.83 (d, 3H). LC-MS: m/e 548 (M+H)⁺ (3.8 min).

EXAMPLE 17

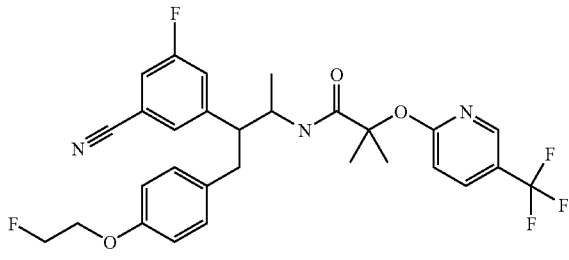

N-{2-(3-Cyano-5-fluorophenyl)-3-[4-(2-fluoroethoxy)phenyl]-1-methylpropyl}-2-(5-trifluoromethyl-2-pyridyloxy)-2-methylpropanamide To a solution of N-[2-(3-cyano-5-fluorophenyl)-3-(4-hydroxyphenyl)-1-methylpropyl]-2-(5-trifluoromethyl-2-pyridyloxy)-2-methylpropanamide from Example 7, Step B (15 mg, 0.039 mmol) in 2 mL of dimethylformamide was added cesium carbonate (15 mg, 0.046 mmol) and 2-fluoroethyl methanesulfonate (20 uL, 0.16 mmol), and the reaction was stirred at 70° C. for 0.5 h. The resulting mixture was diluted with ether (20 mL), washed with water and brine and concentrated to dryness, and the residue was purified by flash column chromatography on silica gel eluted with 10 to 40% ethyl acetate in hexane to give N-{2-(3-cyano-5-fluorophenyl)-3-[4-(2-fluoroethoxy)phenyl]-1-methylpropyl}-2-(5-trifluoromethyl-2-pyridyloxy)-2-methylpropanamide. $^1$H NMR (500 MHz, CD$_3$OD): PL 87 δ 8.27 (br s, 1H), 7.94 (dd, 1H), 7.48 (d, 1H), 7.73-7.32 (m, 3H), 7.04 (s, 1H), 6.64 (s, 4H) 4.68 (m, 1H), 4.59 (m, 1H), 4.25 (m, 1H), 4.11 (m, 1H), 4.04 (m, 1H), 3.02 (dd, 1H), 2.84 (m, 1H), 2.57 (dd, 1H), 1.75 (s, 3H), 1.73 (s, 3H), 0.80 (d, 3H). LC-MS: m/e 544 (M+H)$^+$ (3.8 min).

EXAMPLE 18

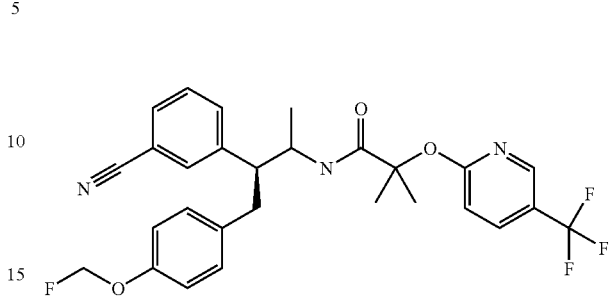

N-(1S,2S)-[2-(3-Cyanophenyl)-3-(4-fluoromethoxyphenyl)-1-methylpropyl]-2-(5-trifluoromethyl-2-pyridyloxy)-2-methylpropanamide N-(1S,2S)-[2-(3-Cyanophenyl)-3-(4-fluoromethoxyphenyl)-1-methylpropyl]-2-(5-trifluoromethyl-2-pyridyloxy)-2-methylpropanamide was prepared from N(1S,2S)-[2-(3-cyanophenyl)-3-(4-hydroxyphenyl)-1-methylpropyl]-2-(5-trifluoromethyl-2-pyridyloxy)-2-methylpropanamide (Example 3, Step A) following the procedure described in Example 16. $^1$H NMR (500 MHz, CD$_3$OD): δ 8.27 (br s, 1H), 7.97 (br d, 1H), 7.94 (dd, 1H), 7.48 (br d, 1H), 7.38-7.34 (m, 3H), 7.04 (br d, 1H), 6.78 (d, 2H), 6.67 (d, 2H), 5.60 (d, 2H), 4.26 (m, 1H), 3.03 (dd, 1H), 2.86 (m, 1H), 2.61 (dd, 1H), 1.75 (s, 3H), 1.73 (s, 3H), 0.81 (d, 3H). LC-MS: m/e 530 (M+H)$^+$ (3.8 min).

Examples 19-26 (Table 1) were prepared from N-(1S, 2S)-[3-(4-chlorophenyl)-2-(3-cyanophenyl)-1-methylpropyl] amine hydrochloride (Reference Example 4) and the appropriate carboxylic acid of Reference Examples following the procedures described in Example 14.

TABLE 1

| Ex. No. | Name | Structure | retention time (min) | HPLC-mass spectrum m/e |
|---|---|---|---|---|
| 19. | N-(1S,2S)-{2-(3-Cyanophenyl)-3-[4-(2-fluoroethoxy)phenyl]-1-methylpropyl}-2-(6-trifluoromethyl-4-pyrimidyloxy)-2-methylpropanamide | 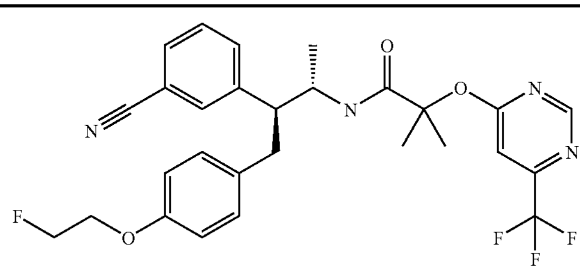 | 3.6 | 545 |
| 20. | N-(1S,2S)-{2-(3-Cyanophenyl)-3-[4-(2-fluoroethoxy)phenyl]-1-methylpropyl}-2-(5-trifluoromethyl-2-pyridyloxy)-2-methylpropanamide | 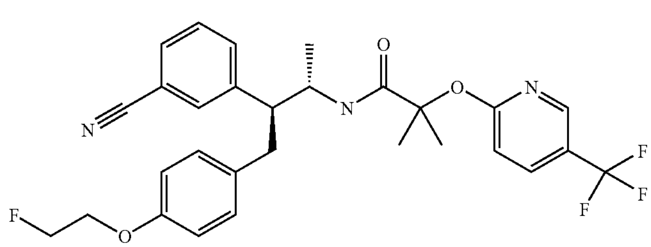 | 3.8 | 544 |

TABLE 1-continued

| Ex. No. | Name | Structure | retention time (min) | HPLC-mass spectrum m/e |
|---|---|---|---|---|
| 21. | N-(1S,2S)-{2-(3-Cyanophenyl)-3-[4-(2-fluoroethoxy)phenyl]-1-methylpropyl}-2-(5-chloromethyl-2-pyridyloxy)-2-methylpropanamide | 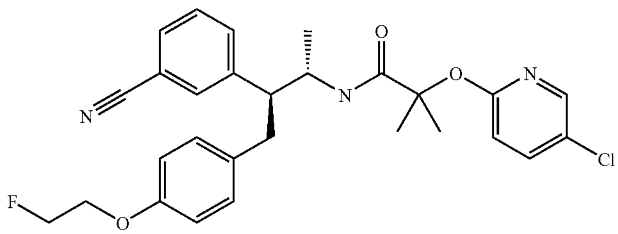 | 3.7 | 510 |
| 22. | N-(1S,2S)-{2-(3-Cyanophenyl)-3-[4-(2-fluoroethoxy)phenyl]-1-methylpropyl}-2-(2-pyridyloxy)-2-methylpropanamide | 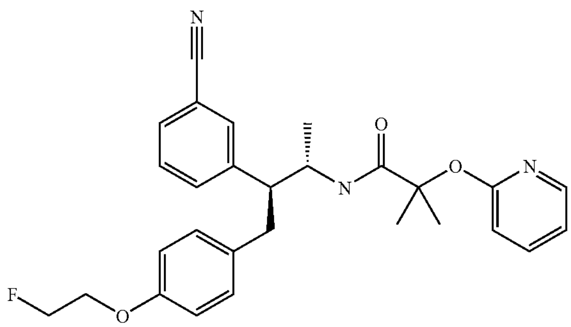 | 3.5 | 476 |
| 23. | N-(1S,2S)-{2-(3-Cyanophenyl)-3-[4-(2-fluoroethoxy)phenyl]-1-methylpropyl}-2-(5-methyl-2-pyridyloxy)-2-methylpropanamide | 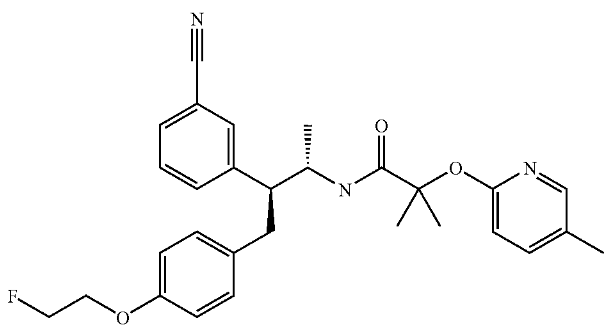 | 3.6 | 490 |
| 24. | N-(1S,2S)-{2-(3-Cyanophenyl)-3-[4-(2-fluoroethoxy)phenyl]-1-methylpropyl}-2-(4-methyl-2-pyridyloxy)-2-methylpropanamide | 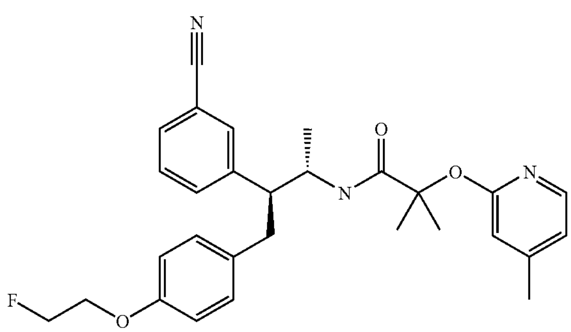 | 3.5 | 490 |
| 25. | N-(1S,2S)-{2-(3-Cyanophenyl)-3-[4-(2-fluoroethoxy)phenyl]-1-methylpropyl}-2-(5-cyano-2-pyridyloxy)-2-methylpropanamide | 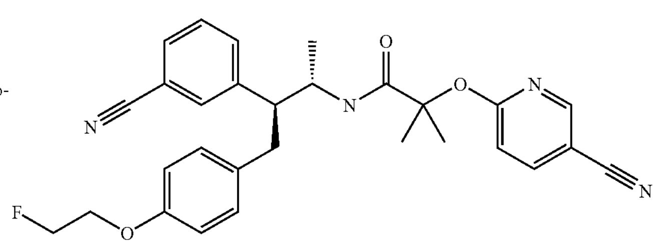 | 3.5 | 501 |

TABLE 1-continued

| Ex. No. | Name | Structure | retention time (min) | HPLC-mass spectrum m/e |
|---|---|---|---|---|
| 26. | N-(1S,2S)-{2-(3-Cyanophenyl)-3-[4-(2-fluoroethoxy)phenyl]-1-methylpropyl}-2-(5-fluoro-2-pyridyloxy)-2-methylpropanamide | 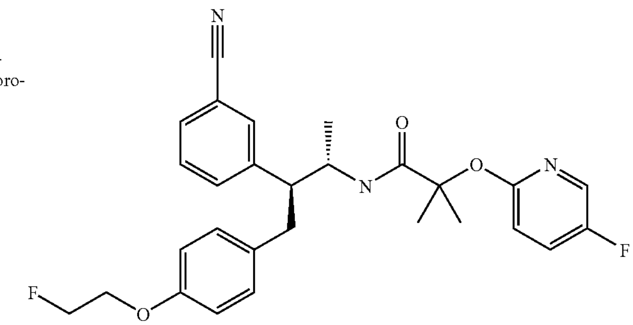 | 3.7 | 494 |

The title compound of Example 23 was recrystallized from a mixture of 5 mL hexane and 3 mL ethyl acetate per gram of title compound to give a crystal form that was characterized as follows:

Differential scanning calorimetry (DSC) data were collected at a heating rate of 10° C./min, under nitrogen atmosphere in a crimped pan. The DSC curve displays a melting endotherm with an extrapolated onset temperature of 87.7° C., a peak temperature of 91.4° C., and an enthalpy change of 77 J/g.

Figure 2:
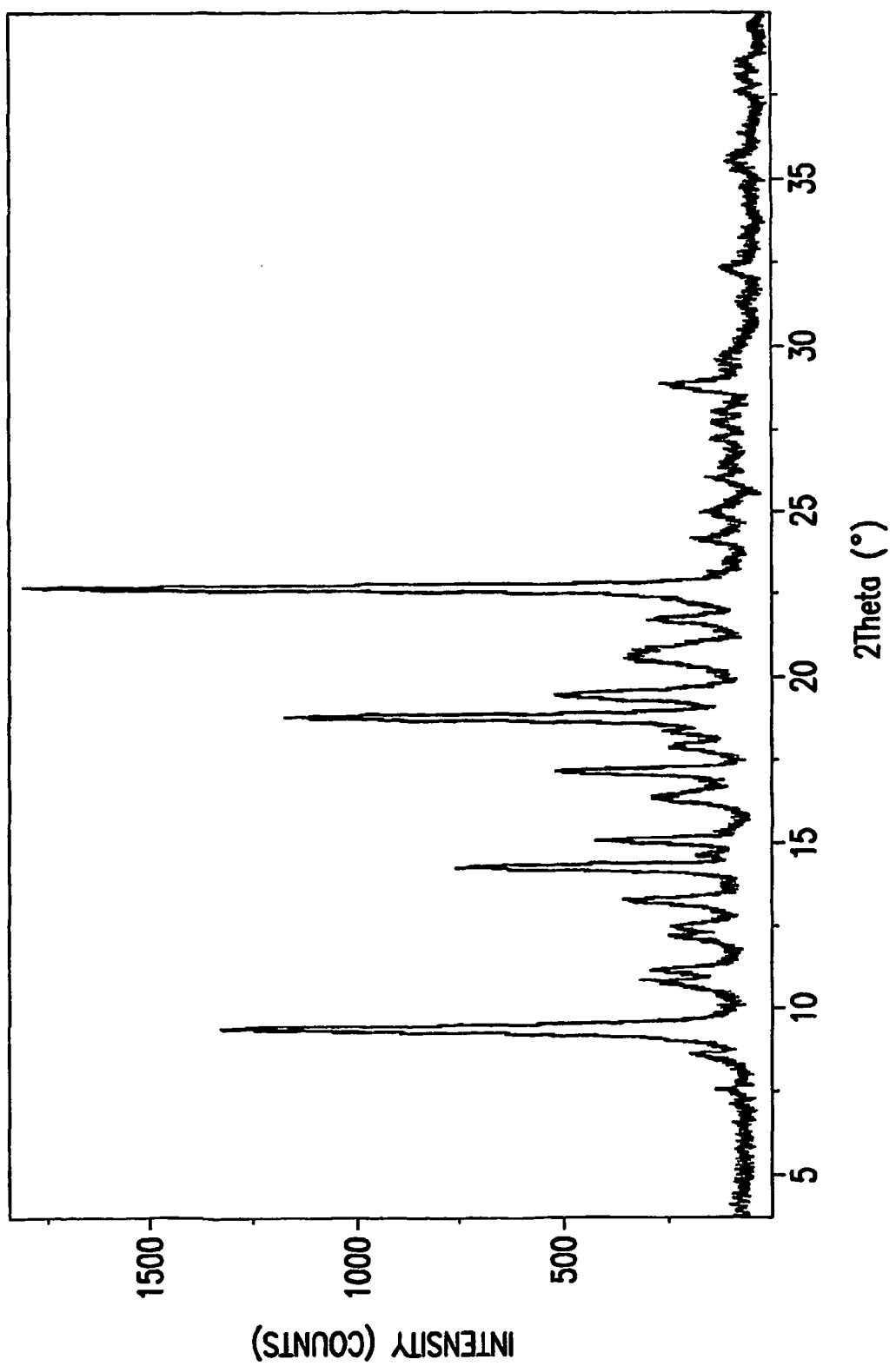
FIG. 2 represents the XRPD of (N-(1S,2S)-{2-(3-Cyanophenyl)-3-[4-(2-fluoroethoxy)phenyl]-1-methylpropyl}-2-(5-methyl-2-pyridyloxy)-2-methylpropanamide). The X axis represents 2-theta in degrees and the Y axis represents Intensity in counts.

The title compound displays the X-ray powder diffraction pattern (XRPD) as shown in FIG. 2. The characteristic diffraction peaks corresponding to d-spacings of 9.4, 6.7, 6.2, 5.2, 4.7, 3.9 angstroms. The X-ray powder diffraction pattern was generated on a Philips Analytical X'Pert PRO X-ray Diffraction System with PW3040/60 console. A PW3373/00 ceramic Cu LEF X-ray tube K-Alpha radiation was used as the source.

EXAMPLES 27-42

The following compounds are made by the methods of Examples 1-11 with the compounds of Examples 12-26.

(27) N-[2-(3-cyano-phenyl)-3-(4-[$^{18}$F]-fluoromethoxyphenyl)-1-methylpropyl]-2-(5-trifluoromethyl-2-pyridyloxy)-2-methylpropanamide;

(28) N-[2-(3-cyano-5-fluorophenyl)-3-(4-[$^{18}$F]-fluoromethoxyphenyl)-1-methylpropyl]-2-(5-trifluoromethyl-2-pyridyloxy)-2-methylpropanamide;

(29) N-(1S,2S)-[2-(3-cyanophenyl)-3-(4-[$^{18}$F]-fluoromethoxyphenyl)-1-methylpropyl]-2-(4-trifluoromethyl-2-pyridyloxy)-2-methylpropanamide;

(30) N-(1S,2S)-{2-(3-cyanophenyl)-3-[4-(2-[$^{18}$F]-fluoroethoxy)phenyl]-1-methylpropyl}-2-(4-trifluoromethyl-2-pyridyloxy)-2-methylpropanamide;

(31) N-[2-(3-cyano-5-[$^{18}$F]-fluorophenyl)-3-(4-methoxyphenyl)-1-methylpropyl]-2-(5-trifluoromethyl-2-pyridyloxy)-2-methylpropanamide;

(32) N-[2-(3-cyano-5-fluorophenyl)-3-(4-[$^{18}$F]-fluoromethoxyphenyl)-1-methylpropyl]-2-(5-trifluoromethyl-2-pyridyloxy)-2-methylpropanamide;

(33) N-(1S,2S)-[2-(3-cyanophenyl)-3-(4-[$^{18}$F]-fluoromethoxyphenyl)-1-methylpropyl]-2-(5-trifluoromethyl-2-pyridyloxy)-2-methylpropanamide;

(34) N-(1S,2S)-{2-(3-cyanophenyl)-3-[4-(2-[$^{18}$F]-fluoroethoxy)phenyl]-1-methylpropyl}-2-(6-trifluoromethyl-4-pyrimidyloxy)-2-methylpropanamide;

(35) N-(1S,2S)-{2-(3-cyanophenyl)-3-[4-(2-[$^{18}$F]-fluoroethoxy)phenyl]-1-methylpropyl}-2-(5-trifluoromethyl-2-pyridyloxy)-2-methylpropanamide;

(36) N-(1S,2S)-{2-(3-cyanophenyl)-3-[4-(2-[$^{18}$F]-fluoroethoxy)phenyl]-1-methylpropyl}-2-(5-chloromethyl-2-pyridyloxy)-2-methylpropanamide;

(37) N-(1S,2S)-{2-(3-cyanophenyl)-3-[4-(2-[$^{18}$F]-fluoroethoxy)phenyl]-1-methylpropyl}-2-(2-pyridyloxy)-2-methylpropanamide;

(38) N-(1S,2S)-{2-(3-cyanophenyl)-3-[4-(2-[$^{18}$F]-fluoroethoxy)phenyl]-1-methylpropyl}-2-(5-methyl-2-pyridyloxy)-2-methylpropanamide;

(39) N-(1S,2S)-{2-(3-cyanophenyl)-3-[4-(2-[$^{18}$F]-fluoroethoxy)phenyl]-1-methylpropyl}-2-(4-methyl-2-pyridyloxy)-2-methylpropanamide;

(40) N-(1S,2S)-{2-(3-cyanophenyl)-3-[4-(2-[$^{18}$F]-fluoroethoxy)phenyl]-1-methylpropyl}-2-(5-cyano-2-pyridyloxy)-2-methylpropanamide;

(41) N-(1S,2S)-{2-(3-cyanophenyl)-3-[4-(2-[$^{18}$F]-fluoroethoxy)phenyl]-1-methylpropyl}-2-(5-fluoro-2-pyridyloxy)-2-methylpropanamide;

(42) N-(1S,2S)-[2-(3-cyanophenyl)-3-(4-methoxyphenyl)-1-methylpropyl]-2-(4-[$^{18}$F]-trifluoromethyl-2-pyridyloxy)-2-methylpropanamide.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

The invention claimed is:
1. A compound selected from:
(1) N-(1S, 2S)-[2-(3-cyanophenyl)-3-(4-chlorophenyl)-1-methylpropyl]-2-(5-[$^{18}$F]-trifluoromethyl-2-pyridyloxy)-2-methylpropanamide;
(2) N-[2-(3-cyano-phenyl)-3-(4-[$^{11}$C]-methoxyphenyl)-1-methylpropyl]-2-(5-trifluoromethyl-2-pyridyloxy)-2-methylpropanamide;
(3) N-[2-(3-cyano-phenyl)-3-(4-[$^{18}$F]-fluoromethoxyphenyl)-1-methylpropyl]-2-(5-trifluoromethyl-2-pyridyloxy)-2-methylpropanamide;
(4) N-[2-(3-cyano-phenyl)-3-(4-[$^{18}$F]-dideuterio-fluoromethoxyphenyl)-1-methylpropyl]-2-(5-trifluoromethyl-2-pyridyloxy)-2-methylpropanamide;
(5) N-[2-(3-cyano-phenyl)-3-(4-(2-[$^{18}$F]-fluoroethoxy)phenyl)-1-methylpropyl]-2-(5-trifluoromethyl-2-pyridyloxy)-2-methylpropanamide;
(6) N-[2-(3-cyano-phenyl)-3-(4-([$^{18}$F]-2-fluoroethoxy)phenyl)-1-methylpropyl]-2-(5-methyl-2-pyridyloxy)-2-methylpropanamide;
(7) N-[2-(3-cyano-5-fluorophenyl)-(4-[$^{11}$C]-methoxyphenyl)-1-methylpropyl]-2-(5-trifluoromethyl-2-pyridyloxy)-2-methylpropanamide;
(8) N-[2-(3-cyano-5-fluorophenyl)-(4-[$^{18}$F]-fluoromethoxyphenyl)-1-methylpropyl]-2-(5-trifluoromethyl-2-pyridyloxy)-2-methylpropanamide;
(9) N-[2-(3-cyano-5-fluorophenyl)-(4-[$^{18}$F]-dideuteriofluoromethoxyphenyl)-1-methylpropyl]-2-(5-trifluoromethyl-2-pyridyloxy)-2-methylpropanamide;
(10) N-[2-(3-cyano-5-fluorophenyl)-(4-(2-[$^{18}$F]-fluoroethoxy)phenyl)-1-methylpropyl]-2-(5-trifluoromethyl-2-pyridyloxy)-2-methylpropanamide;
(11) N-(1S, 2S)-[3-(4-chlorophenyl)-2-(3-cyano-5-fluorophenyl)-1-methylpropyl]-2-5-[$^{18}$F]-(trifluoromethyl-2-pyridyloxy)-2-methylpropanamide;
(12) N-(1S, 2S)-[3-(4-chloro-2,5-ditritiophenyl)-2-(3-cyanophenyl)-1-methylpropyl]-2-(5-trifluoromethyl-2-pyridyloxy)-2-methylpropanamide;
(13) N-(1S,2S)-[2-(3-cyanophenyl)-3-(4-methoxyphenyl)-1-methylpropyl]-2-(4-[$^{18}$F]-trifluoromethyl-2-pyridyloxy)-2-methylpropanamide;
(14) N-(1S,2S)-[2-(3-cyanophenyl)-3-(4-[$^{18}$F]-fluoromethoxyphenyl)-1-methylpropyl]-2-(4-trifluoromethyl-2-pyridyloxy)-2-methylpropanamide;
(15) N-(1S,2S)-{2-(3-cyanophenyl)-3-[4-(2-[$^{18}$F]-fluoroethoxy)phenyl]-1-methylpropyl}-2-(4-trifluoromethyl-2-pyridyloxy)-2-methylpropanamide;
(16) N-[2-(3-cyano-5-[$^{18}$F]-fluorophenyl)-3-(4-methoxyphenyl)-1-methylpropyl]-2-(5-trifluoromethyl-2-pyridyloxy)-2-methylpropanamide;
(17) N-[2-(3-cyano-5-fluorophenyl)-3-(4-[$^{18}$F]-fluoromethoxyphenyl)-1-methylpropyl]-2-(5-trifluoromethyl-2-pyridyloxy)-2-methylpropanamide;
(18) N-(1S,2S)-[2-(3-cyanophenyl)-3-(4-[$^{18}$F]-fluoromethoxyphenyl)-1-methylpropyl]-2-(5-trifluoromethyl-2-pyridyloxy)-2-methylpropanamide;
(19) N-(1S,2S)-{2-(3-cyanophenyl)-3-[4-(2-[$^{18}$F]-fluoroethoxy)phenyl]-1-methylpropyl}-2-(6-trifluoromethyl-4-pyrimidyloxy)-2-methylpropanamide;
(20) N-(1S,2S)-{2-(3-cyanophenyl)-3-[4-(2-[$^{18}$F]-fluoroethoxy)phenyl]-1-methylpropyl}-2-(5-trifluoromethyl-2-pyridyloxy)-2-methylpropanamide;
(21) N-(1S,2S)-{2-(3-cyanophenyl)-3-[4-(2-[$^{18}$F]-fluoroethoxy)phenyl]-1-methylpropyl}-2-(5-chloromethyl-2-pyridyloxy)-2-methylpropanamide;
(22) N-(1S,2S)-{2-(3-cyanophenyl)-3-[4-(2-[$^{18}$F]-fluoroethoxy)phenyl]-1-methylpropyl}-2-(2-pyridyloxy)-2-methylpropanamide;
(23) N-(1S,2S)-{2-(3-cyanophenyl)-3-[4-(2-[$^{18}$F]-fluoroethoxy)phenyl]-1-methylpropyl}-2-(5-methyl-2-pyridyloxy)-2-methylpropanamide;
(24) N-(1S,2S)-{2-(3-cyanophenyl)-3-[4-(2-[$^{18}$F]-fluoroethoxy)phenyl]-1-methylpropyl}-2-(4-methyl-2-pyridyloxy)-2-methylpropanamide;
(25) N-(1S,2S)-{2-(3-cyanophenyl)-3-[4-(2-[$^{18}$F]-fluoroethoxy)phenyl]-1-methylpropyl}-2-(5-cyano-2-pyridyloxy)-2-methylpropanamide;
(26) N-(1S,2S)-{2-(3-cyanophenyl)-3-[4-(2-[$^{18}$F]-fluoroethoxy)phenyl]-1-methylpropyl}-2-(5-fluoro-2-pyridyloxy)-2-methylpropanamide;
and pharmaceutically acceptable salts thereof.

2. The compound according to claim 1 selected from:
N-{[2-(3-cyanophenyl)-3-[4-([$^{18}$F]-2-fluoroethoxy)phenyl]-1-methylpropyl}-2-(5-trifluoromethyl-2-pyridyloxy)-2-methylpropanamide, and
N-{[2-(3-cyanophenyl)-3-[4-([$^{18}$F]-2-fluoroethoxy)phenyl]-1-methylpropyl}-2-(5-methyl-2-pyridyloxy)-2-methylpropanamide,
and pharmaceutically acceptable salts thereof.

3. A radiopharmaceutical composition which comprises the compound according to claim 1 and at least one pharmaceutically acceptable carrier or excipient.

4. A method for the diagnostic imaging of cannabinoid-1 receptors in a mammal which comprises administering to a mammal in need of such diagnostic imaging an effective amount of the compound according to claim 1.

5. The method according to claim 4, wherein the mammal is human.

6. A method for the diagnostic imaging of the brain in a human which comprises administering to a human in need of such diagnostic imaging an effective amount of the compound of claim 1.

7. A method for the diagnostic imaging of tissues bearing cannabinoid-1 receptors in a mammal which comprises administering to a mammal in need of such diagnostic imaging an effective amount of the compound of claim 1.

8. The method according to claim 7, wherein the mammal is human.

9. A method for the detection or quantification of cannabinoid-1 receptors in mammalian tissue which comprises contacting such mammal tissue in which such detection or quantification is desired with an effective amount of the compound of claim 1.

10. The method according to claim 9 wherein the mammalian tissue is human tissue.

11. A process for the preparation of the compounds of claim 2, N-{[2-(3-cyanophenyl)-3-[4-([$^{18}$F]-2-fluoroethoxy)phenyl]-1-methylpropyl}-2-(5-trifluoromethyl-2-pyridyloxy)-2-methylpropanamide, and
N-{[2-(3-cyanophenyl)-3-[4-([$^{18}$F]-2-fluoroethoxy)phenyl]-1-methylpropyl}-2-(5-methyl-2-pyridyloxy)-2-methylpropanamide, comprising: contacting N-[2-(3-cyanophenyl)-3-(4-hydroxyphenyl)-1-methylpropyl]-2-(5-trifluoromethyl-2-pyridyloxy)-2-methylpropanamide and N-[2-(3-cyanophenyl)-3-(4-hydroxyphenyl)-1-methylpropyl]-2-(5-methyl-2-pyridyloxy)-2-methylpropanamide with an alkylating agent selected from [$^{18}$F]fluoroethyl bromide and [$^{18}$F] fluoroethyl tosylate in the presence of a weak base, such as cesium carbonate, in an inert solvent, such as dimethylformamide, at a temperature between room temperature and solvent reflux temperature, preferably about 100° C.

* * * * *